United States Patent
Guzman et al.

(10) Patent No.: US 9,901,920 B1
(45) Date of Patent: Feb. 27, 2018

(54) PIPETTING DEVICE, PIPETTE TIP COUPLER, AND PIPETTE TIP: DEVICES AND METHODS

(71) Applicant: Hamilton Company, Reno, NV (US)

(72) Inventors: Jose Eduardo Guzman, Sparks, NV (US); Thomas Barresi, Reno, NV (US); Dana A. Belton, Sparks, NV (US)

(73) Assignee: Hamilton Company, Reno, NV (US)

(*) Notice: Subject to any disclaimer, the term of this patent is extended or adjusted under 35 U.S.C. 154(b) by 0 days.

(21) Appl. No.: 15/793,750

(22) Filed: Oct. 25, 2017

Related U.S. Application Data

(63) Continuation of application No. 15/420,568, filed on Jan. 31, 2017.

(60) Provisional application No. 62/350,302, filed on Jun. 15, 2016, provisional application No. 62/350,291, filed on Jun. 15, 2016.

(51) Int. Cl.
*B01L 3/02* (2006.01)

(52) U.S. Cl.
CPC ....... *B01L 3/0279* (2013.01); *B01L 2200/023* (2013.01); *B01L 2200/04* (2013.01); *B01L 2200/0689* (2013.01); *B01L 2300/0832* (2013.01); *B01L 2300/123* (2013.01)

(58) Field of Classification Search
CPC combination set(s) only.
See application file for complete search history.

(56) References Cited

U.S. PATENT DOCUMENTS

| | | | |
|---|---|---|---|
| 4,023,716 A | 5/1977 | Shapiro | |
| 4,187,724 A | 2/1980 | Citrin | |
| 4,284,604 A * | 8/1981 | Tervamaki | B01L 3/0224 422/517 |
| 4,830,832 A | 5/1989 | Arpagaus | |
| 4,863,695 A | 9/1989 | Fullemann | |
| 4,967,604 A | 11/1990 | Arpagaus | |

(Continued)

FOREIGN PATENT DOCUMENTS

| | | |
|---|---|---|
| DE | 102015213005 | 12/2017 |
| EP | 2311566 | 4/2011 |

(Continued)

*Primary Examiner* — Brian R Gordon
(74) *Attorney, Agent, or Firm* — Dennis A. DeBoo; Audrey A. Millemann; Weintraub Tobin

(57) ABSTRACT

Pipette tip coupler and a disposable pipette tip for a pipette device comprises a stepped coupler shoulder complementary to an axially stepped pipette tip shoulder; a plurality of circumferentially disposed elements or segments carried by the coupler at a location superior to the coupler shoulder; and a distal elastomeric element carried by the coupler at a location distal to the coupler shoulder wherein the plurality of elements or segments have a circumferential, radially translated state that provides an abutment with a first working surface formed in the interior surface of the tip while compressing the distal elastomeric element into sealing abutment with a second working surface formed in the interior surface of the tip and while abutting the proximally facing axial stop surface of the tip with the distally facing axial stop surface of the coupler to define an axial coupling position of the pipette tip on the pipette device.

30 Claims, 67 Drawing Sheets

(56) References Cited

U.S. PATENT DOCUMENTS

| | | | | |
|---|---|---|---|---|
| 5,121,642 A | * | 6/1992 | Davidowicz | B01L 3/02 422/919 |
| 5,200,151 A | | 4/1993 | Long | |
| 5,232,669 A | * | 8/1993 | Pardinas | B01L 3/0275 206/562 |
| 5,525,302 A | * | 6/1996 | Astle | B01L 3/0279 422/511 |
| 5,620,660 A | | 4/1997 | Belgardt | |
| 5,948,359 A | * | 9/1999 | Kalra | G01N 1/312 422/510 |
| 6,168,761 B1 | | 1/2001 | Kelly | |
| 6,171,553 B1 | | 1/2001 | Petrek | |
| 6,248,295 B1 | | 6/2001 | Petrek | |
| 6,399,024 B1 | | 6/2002 | Bevirt | |
| 6,495,106 B1 | | 12/2002 | Kalra | |
| 6,499,363 B1 | * | 12/2002 | Morimoto | B01L 3/0231 73/864.01 |
| 6,568,288 B2 | | 5/2003 | Rainin | |
| 6,596,240 B2 | * | 7/2003 | Taggart | B01L 3/0275 422/525 |
| 6,673,318 B1 | * | 1/2004 | Nishimura | B01L 3/0279 222/542 |
| 6,737,023 B1 | | 5/2004 | Kelly | |
| 6,745,636 B2 | | 6/2004 | Rainin | |
| 6,780,381 B2 | | 8/2004 | Yiu | |
| 6,955,077 B2 | | 10/2005 | Blaszcak | |
| 6,967,004 B2 | | 11/2005 | Rainin | |
| 6,973,845 B2 | | 12/2005 | Bell | |
| 7,033,543 B1 | | 4/2006 | Panzer | |
| 7,047,828 B2 | | 5/2006 | Blaszcak | |
| 7,320,259 B2 | | 1/2008 | Jessop | |
| 7,335,337 B1 | * | 2/2008 | Smith | B01L 3/0275 422/513 |
| 7,344,680 B2 | | 3/2008 | Mahler | |
| 7,641,859 B2 | | 1/2010 | Cote | |
| 7,662,343 B2 | | 2/2010 | Mathus | |
| 7,662,344 B2 | | 2/2010 | Mathus | |
| 7,690,293 B2 | | 4/2010 | Bensley | |
| 7,785,466 B1 | * | 8/2010 | Smith | B01L 3/0275 210/321.75 |
| 8,163,256 B2 | | 4/2012 | Cote | |
| 8,202,495 B1 | * | 6/2012 | Smith | B01L 3/0275 422/500 |
| 8,277,757 B2 | | 10/2012 | Kelly | |
| 8,337,782 B2 | | 12/2012 | Bensley | |
| 8,398,934 B2 | | 3/2013 | Bensley | |
| 8,501,118 B2 | | 8/2013 | Mathus | |
| 8,512,650 B2 | | 8/2013 | Jungheim | |
| 8,524,170 B2 | | 9/2013 | Petrek | |
| 8,557,197 B2 | | 10/2013 | Leckebusch | |
| 8,703,071 B2 | | 4/2014 | Cerra | |
| 8,877,513 B2 | | 11/2014 | Mathus | |
| 9,079,178 B2 | | 7/2015 | Sheldon | |
| 9,333,500 B2 | | 5/2016 | Mathus | |
| 9,346,045 B2 | | 5/2016 | Blumentritt | |
| 9,415,388 B2 | | 8/2016 | Panzer | |
| 2002/0001545 A1 | * | 1/2002 | Cronenberg | B01L 3/0279 422/525 |
| 2003/0082078 A1 | * | 5/2003 | Rainin | B01L 3/0279 422/522 |
| 2003/0177849 A1 | * | 9/2003 | Matsuda | B01L 3/0279 73/864.14 |
| 2005/0175511 A1 | | 8/2005 | Cote | |
| 2005/0184516 A1 | | 8/2005 | Seguin | |
| 2005/0204832 A1 | | 9/2005 | Jessop | |
| 2005/0255005 A1 | | 11/2005 | Motadel | |
| 2006/0233669 A1 | | 10/2006 | Panzer | |
| 2008/0078258 A1 | | 4/2008 | Price | |
| 2010/0196210 A1 | * | 8/2010 | Jungheim | B01L 3/0275 422/526 |
| 2011/0076205 A1 | | 3/2011 | Kelly | |
| 2013/0136672 A1 | | 5/2013 | Blumentritt | |
| 2013/0216705 A1 | | 8/2013 | Sprung | |
| 2014/0056781 A1 | | 2/2014 | Jaaskelainen | |
| 2014/0219887 A1 | * | 8/2014 | Sheldon | B01L 3/0279 422/509 |
| 2015/0037227 A1 | * | 2/2015 | Ding | B01L 3/0293 422/509 |
| 2015/0086447 A1 | | 3/2015 | Mathus | |
| 2015/0239129 A1 | | 8/2015 | Buchloh | |
| 2015/0276107 A1 | | 10/2015 | Stadler | |
| 2016/0051979 A1 | | 2/2016 | Herbst | |
| 2017/0361323 A1 | * | 12/2017 | Guzman | B01L 3/563 |

FOREIGN PATENT DOCUMENTS

| | | |
|---|---|---|
| JP | 3748231 | 2/2006 |
| KR | 20120008943 | 12/2012 |

* cited by examiner

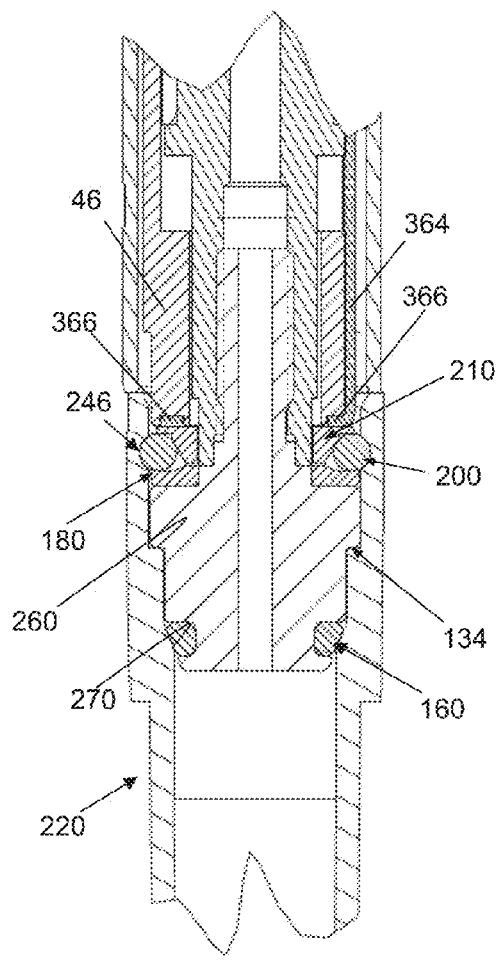
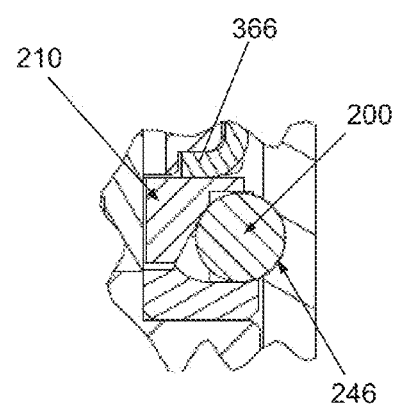
FIG. 24
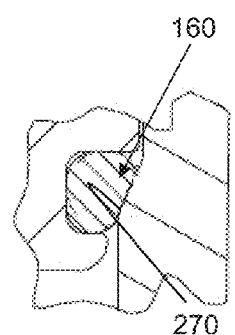
FIG. 23    FIG. 25

3001

3002

3003

3004

3005

3006

PIPETTING DEVICE, PIPETTE TIP COUPLER, AND PIPETTE TIP: DEVICES AND METHODS

CROSS-REFERENCE TO RELATED APPLICATIONS

This application is a continuation of and claims the benefit of priority from U.S. patent application Ser. No. 15/420,568, which is entitled "Pipetting Device, Pipette Tip Coupler, and Pipette Tip: Devices and Methods" and filed on Jan. 31, 2017, which claims the benefit of priority from two (2) U.S. Provisional Patent Application Nos. 62/350,291 filed Jun. 15, 2016, and 62/350,302 filed Jun. 15, 2016, all of which are fully incorporated herein by reference.

FIELD

This disclosure pertains generally to pipetting devices, and more particularly to pipette tip couplers, disposable pipette tips, tip and coupler combinations, and coupling and decoupling methods of at least one disposable pipette tip to or from at least one pipette tip coupler carried by a pipette device.

BACKGROUND

Pipette devices are used in a multitude of industries for the transfer of liquids to conduct experimental analysis. As such, to provide control within the experiments being performed, disposable tips are used and intended for one-time use. Disposable tips are employed with both manual pipette devices and automated pipette devices having a large number of pipette units arranged in a row or in a matrix for aspirating samples simultaneously from a large number of vessels and dispensing them elsewhere.

Disposable pipette tips have been constructed historically to interface to either a conical or stepped coupling stud. In the cases where a conical coupling stud is used, the disposable tip is constructed in a manner that it must be pre-stressed onto the coupling stud to provide an air tight seal. Due to the tolerances of the two interfacing components, the distance to the end of the tip that comes in contact with liquid is not well controlled. In addition, high press forces are required to pre-stress the tip to create the air tight seal. As a result, microfissures may be formed in the pipette tip which are a cause of leakage. Moreover, the high press forces upon placement of the pipette tip have the disadvantage that for the release of the pipette tip correspondingly high forces have to be applied.

The assignee of the present application, HAMILTON Company, teaches in U.S. Pat. No. 7,033,543, issued Apr. 25, 2006, a stepped coupling stud in conjunction with an O-ring that provides a solution for reducing the high press force required to create an air tight seal as well as providing well defined axial positioning of the end of the tip that comes in contact with liquid. As the O-ring is compressed, it provides axially directed force to not only provide the air-tight seal, but also to engage the axial coupling feature on the coupling stud with the counter axial coupling feature on the tip.

Nevertheless, current systems utilizing a stepped coupling stud and a solitary O-ring configuration are problematic when the O-ring becomes compromised because the result is an impairment in the air-tight seal and the performance of the pipette device.

Additionally, the compression of the O-ring results in the deformation of the O ring that in turn provides the axially directed force and air-tight seal against the working surface of the pipette tip. Counter to this operation, when the compression of the O-ring is removed, the O-ring must disengage from the working surface of the pipette tip to allow the pipette tip to be removed from the coupling stud and the pipette device for disposal. If the O-ring does not fully decompress, some residual force will remain resulting in keeping the tip engaged to the coupling stud and thus requiring an automated external axial counterforce to remove the tip for disposal.

Moreover, as the size of the holes to and/or from which liquid is transferred decreases, the need for precision positioning of all of the tips in a controlled manner increases in order to allow successful targeting.

Hence, there is a need to ameliorate or overcome one or more of the significant shortcomings delineated hereinabove.

SUMMARY

Accordingly, and in one aspect, an embodiment of the present disclosure ameliorates or overcomes one or more of the shortcomings of the known prior art by providing a pipette tip coupler and disposable pipette tip combination that comprises a plurality of circumferentially disposed elements or segments engaging a circumferential interior working surface defining a first working surface of an interior circumscribing surface of a sidewall of the pipette tip in an area superior to a proximally facing axial stop surface of the pipette tip for providing a resultant pre-stress force that pre-stresses the pipette tip axially upward causing a distal elastomeric element of the coupler to be pre-stressed against a second working surface of the pipette tip forming a seal configuration that eliminates the seal deterioration or failure of the known prior art.

In addition, and in one aspect, the distal elastomeric element, when compressed against the second working surface, provides a counter axial force to the plurality of elements or segments wherein at least one benefit of this counter axial force is that additional force is applied to the first working surface by the plurality of individual elements or segments when the plurality of individual elements or segments are in a radially and axially interfacing state for providing a stronger distal seal.

A further benefit of the counter axial force is that when the plurality of individual elements or segments are disengaged to a radially and axially retracted state, the counter axial force of the distal elastomeric element defines a counter axially directed disengaging force that aids in the removal of the pipette tip from the pipette tip coupler for disposal.

In another aspect, an embodiment of the present disclosure provides a pipette tip coupler and disposable pipette tip combination, the coupler comprising a plurality of circumferentially disposed elements or segments and a distal elastomeric element in the form of, but not limited to, an O-ring and the pipette tip comprising dual complemental working surfaces in the pipette tip to provide a resultant axial force achieved from an engagement of the plurality of elements or segments and the distal elastomeric element with the dual complemental working surfaces for pre-stressing the disposable pipette tip into an axial coupling position that is provided by a distally facing axial stop surface of the pipette tip coupler and a proximally facing complimentary counter axial stop surface of the disposable pipette tip such that a perpendicular datum is established to a longitudinal axis of a channel of a pipette device carrying the pipette tip coupler and disposable pipette tip combination that provides for tip straightness and controlled concentricity.

One benefit of the resultant axial force coupling position over the known prior art is the establishment of this perpendicular datum that provides for tip straightness and controlled concentricity. Concentricity becomes worse as an angle defined herein as "ø" between a transverse axis and the longitudinal axis perpendicular to the transverse axis is allowed to increase. Thus, controlled concentricity becomes especially important in a multi-channel system and when targeting multiple wells. Accordingly, the pipette tip coupler and disposable tip combination provides tighter concentricity to allow for tighter precision of all the tips in a controlled manner allowing successful targeting of multiple wells and/or smaller holes to and/or from which liquid is transferred.

In yet another aspect, an embodiment of the present disclosure provides a pipette tip coupler and disposable pipette tip combination, the coupler comprising a plurality of circumferentially disposed elements or segments and a distal elastomeric element in the form of, but not limited to, an O-ring and the pipette tip comprising dual complemental working surfaces in the pipette tip to provide precise control of an axial coupled position defined as an axial distance from a distally facing axial stop surface of the pipette tip coupler to the end of the pipette tip that contacts liquid when the pipette tip coupler and disposable pipette tip are in a coupled configuration. This, combined with tip straightness, allows for a pipette device carrying the pipette tip coupler and disposable tip combination to target smaller holes. Additionally, smaller volumes of liquid can be transferred resulting from the known fixed distance of the disposable pipette tip allowing for a controlled touch of the pipette tip/liquid to a working surface onto or from which liquid is to be transferred.

In a further aspect, an embodiment of the present disclosure provides a pipette tip coupler and disposable pipette tip combination comprising an angled squeeze mechanism, such as an annular wedge or squeeze ring, that directs the motion of the plurality of individual elements into contact with the first working surface of the pipette tip. The result is more axial force to pre-stress the pipette tip into the axial coupling position.

In yet a further aspect, an embodiment of the present disclosure provides a pipette tip coupler device for coupling a pipette tip to a pipette device, the pipette tip coupler device comprising: a pipette tip coupler body having an upper seating surface and a distally facing axial stop surface that is complementary to a proximally facing axial stop surface of an axially stepped shoulder of an interior circumscribing surface of a sidewall of a pipette tip; a distal stem portion distally extending from a distal surface of the pipette tip coupler body along a central longitudinal axis of the pipette tip coupler body and terminating to a distal end; a distal elastomeric element circumscribing the distal stem portion, the distal elastomeric element comprising a relaxed state, and a compressed state configured for sealing and abutting the distal elastomeric element with a circumferential radially inwardly angled and distally extending distal sealing surface of the interior circumscribing surface of the sidewall of the pipette tip located in an area inferior to the axially stepped shoulder of the pipette tip; and a plurality of individual elements or segments circumferentially spaced apart and mounted on the upper seating surface of the pipette tip coupler body and configured to extend between circumferentially spaced apart radially retracted positions and circumferentially spaced apart radially advanced positions configured for providing an abutment of the plurality of individual elements or segments with a first interior working surface of the interior circumscribing surface of the sidewall of the pipette tip in an area superior to the axially stepped shoulder of the pipette tip while the distal elastomeric element is concurrently in the compressed state and the upwardly facing axial stop surface of the pipette tip is in abutment with the downwardly facing axial stop surface of the pipette tip coupler body to define an axial coupling position of the pipette tip on the pipette tip coupler device.

Further aspects of the embodiments of the present disclosure will become apparent from the detailed description provided below, when taken together with the attached drawings and claims. It should be understood, however, that numerous modifications and adaptations may be resorted to without departing from the scope and fair meaning of the claims as set forth below following the detailed description of preferred embodiments of the present disclosure.

BRIEF DESCRIPTION OF THE SEVERAL VIEWS OF THE DRAWINGS

The foregoing summary, as well as the following detailed description of the disclosure, will be more fully understood by reference to the following drawings that are for illustrative purposes only, and are not intended to limit the scope of the present disclosure. Also, it is appreciable that the drawings are not necessarily in scale as some components may be shown to be enlarged or to be out of proportion relative to the size in actual implementation in order to more clearly illustrate one or more concepts of the present disclosure. In the drawings:

FIG. 23 is a fragmentary, longitudinal sectional, side elevational view of an example embodiment of the pipette tip coupler device moved a final distance into the tip with the tip being lifted up to its final seated state to engage the coupler by the method of moving the annular wedge into its final position thereby defining a final state of coupling with the distal elastomeric element or O-ring in a final compressed and seated sealing state.

FIG. 24 is a longitudinal sectional, side elevational, fragmented detailed view of one of the plurality of segments or balls in the final extended or lift state as is illustrated in FIG. 23.

FIG. 25 is a longitudinal sectional, side elevational, fragmented detailed view of the distal elastomeric element or O-ring in a final compressed state against the tip sealing seat or surface as is illustrated in FIG. 23.

Figure 1:
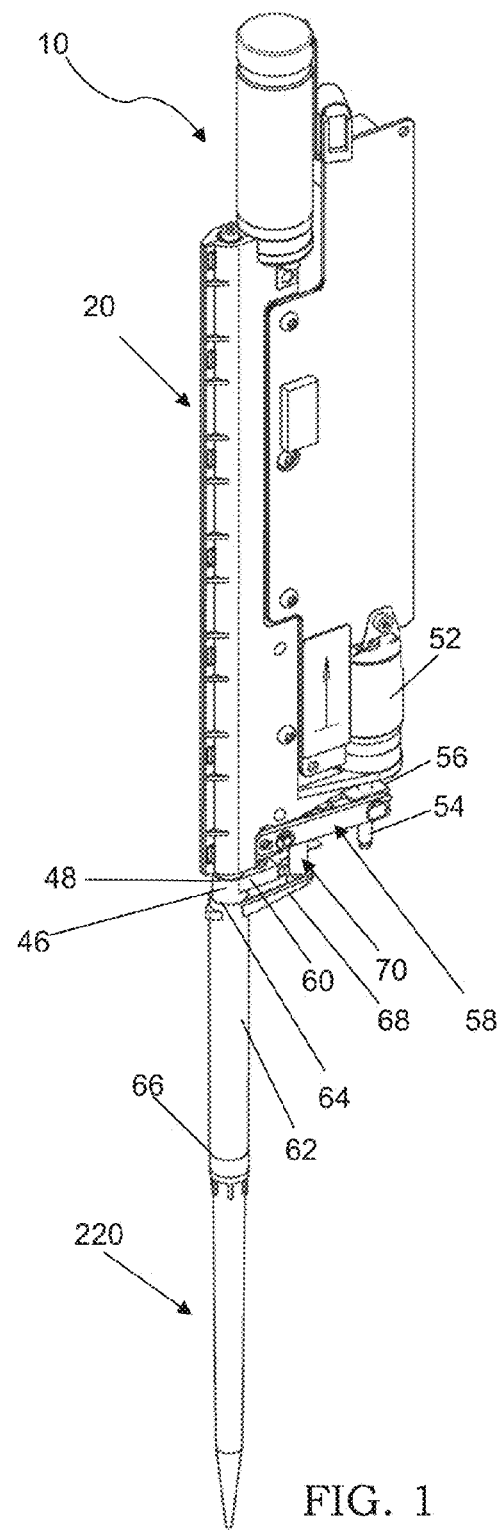
FIG. 1 is a perspective view of an example embodiment of an air displacement pipette device assembly of an automated liquid handling system.

Although various example embodiments may be numbered herein, these embodiments should not be limited by these terms. These terms are only used to distinguish one embodiment from another. Additionally, these terms do not imply a sequence or order.

DETAILED DESCRIPTION

For the purpose of illustrating the disclosure, there are shown in the drawings embodiments that are presently preferred. These example embodiments will now be described more fully with reference to the accompanying drawings wherein like reference numerals are used to denote like parts or portions throughout the description of the several views of the drawings.

Pipette Assembly with Pipette Tip Coupler and Disposable Pipette Tip

Figure 2:
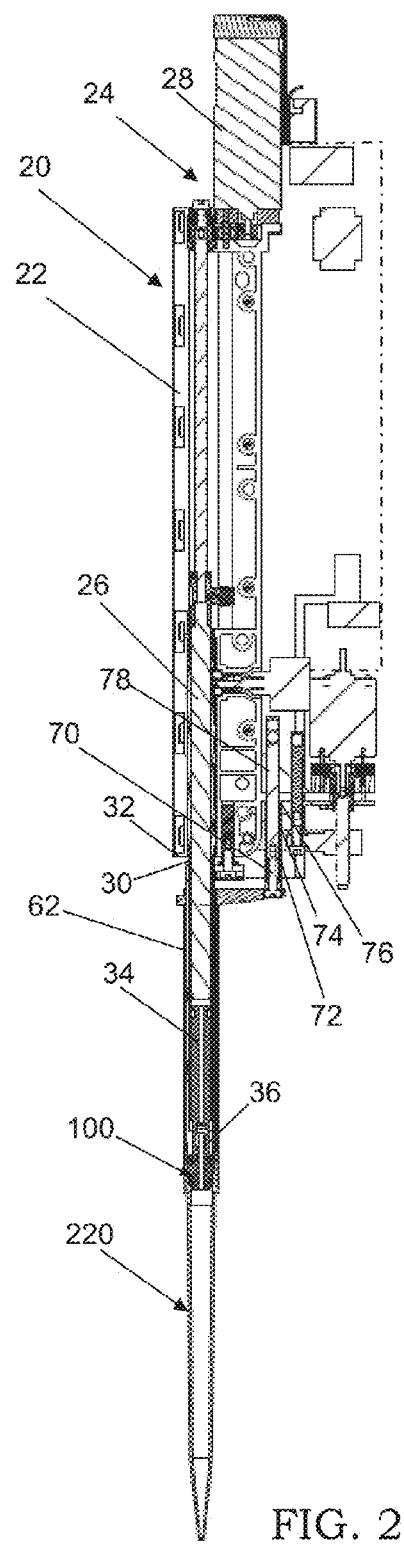
FIG. 2 is a longitudinal sectional, side elevational view of an example embodiment of the pipette device assembly.

FIGS. 1 and 2 illustrate an example embodiment of a pipette device assembly 10 comprising an example embodiment of a pipette device 20, an example embodiment of a pipette tip coupler device 100, and an example embodiment of a disposable pipette tip 220 removably coupled to the pipette device 20 by way of the pipette tip coupler device 100.

Pipette Device 20

Referring to FIG. 2, the pipette device 20 comprises a body 22 supporting an aspirating and dispensing device 24 comprising a plunger 26 operatively coupled to and driven by a motor 28. The plunger 26 resides within a plunger cylinder 30 extending from a distal or lower end 32 of the body 22 of the pipette device 20. Pipette device 20 further comprises an aspirating and dispensing cylinder 34 that is at least partially disposed within plunger cylinder 30 at a location axially aligned with and distally below the plunger 26. The aspirating and dispensing cylinder 34 distally transitions into a distal mounting flange 36 for attaching with the segment and seal pipette tip coupler device 100 that, in turn, removably couples with the disposable pipette tip 220.

Figure 3:
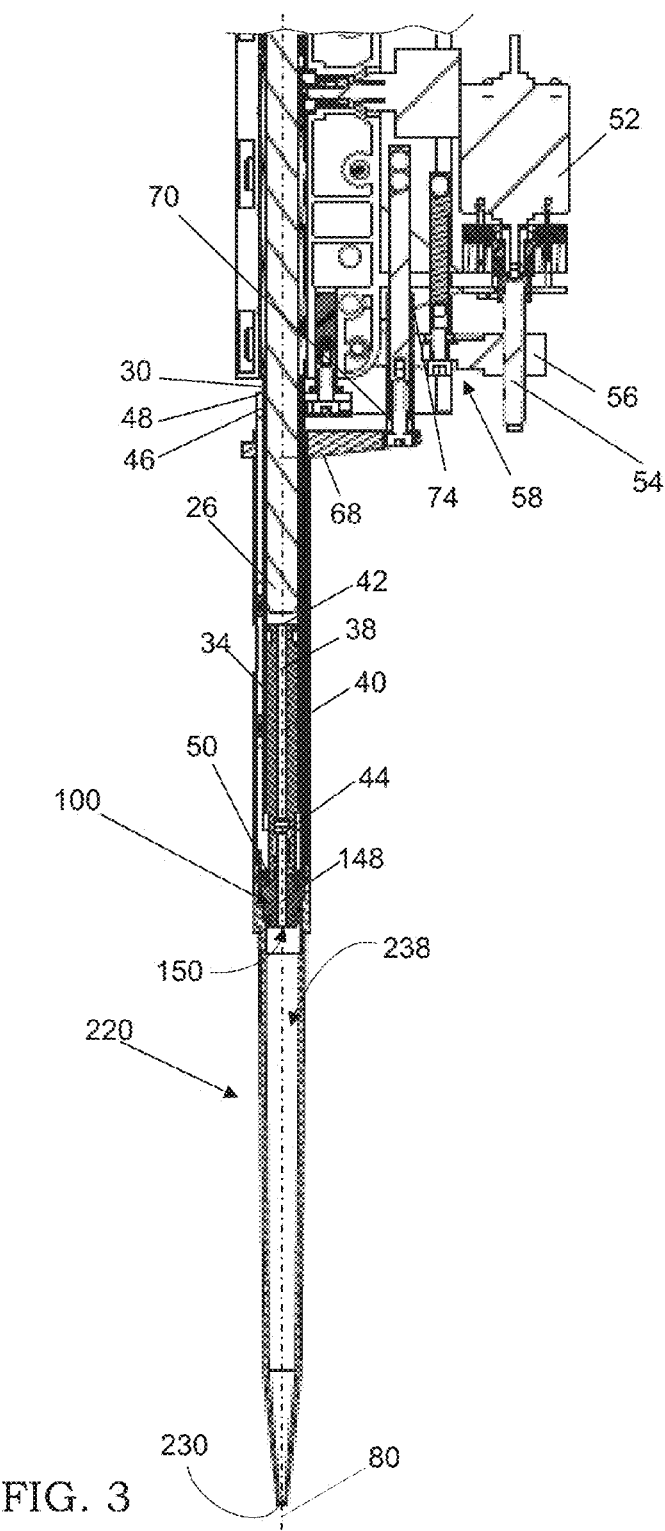
FIG. 3 is a fragmentary longitudinal sectional, side elevational view of an example embodiment of the pipette device assembly comprising a pipette device operatively coupled to an example embodiment of a pipette tip coupler device that is operatively coupled to an example embodiment of a disposable pipette tip.

Referring to FIG. 3, the aspirating and dispensing cylinder 34 further comprises an interior circumscribing side wall 38 that defines an open-ended pipette channel 40 extending therethrough. The open ended pipette channel 40 longitudinally extends along a longitudinal channel axis 80 of the pipette device assembly 10 between an open upper end portion 42 and open lower end portion 44 of the aspirating and dispensing cylinder 34 for providing open communication between plunger 26 and an exterior area adjacent distal mounting flange 36 (FIG. 2) wherein the distal mounting flange 36 is operatively connected to the pipette tip coupler 100 comprising an open ended cylindrically shaped central channel 150 extending therethrough to provide open commination between the passage opening 238 of the tip 220 and the aspirating and dispensing cylinder 34 via the pipette tip coupler 100.

Piston or Squeeze Sleeve 46

Figure 4:
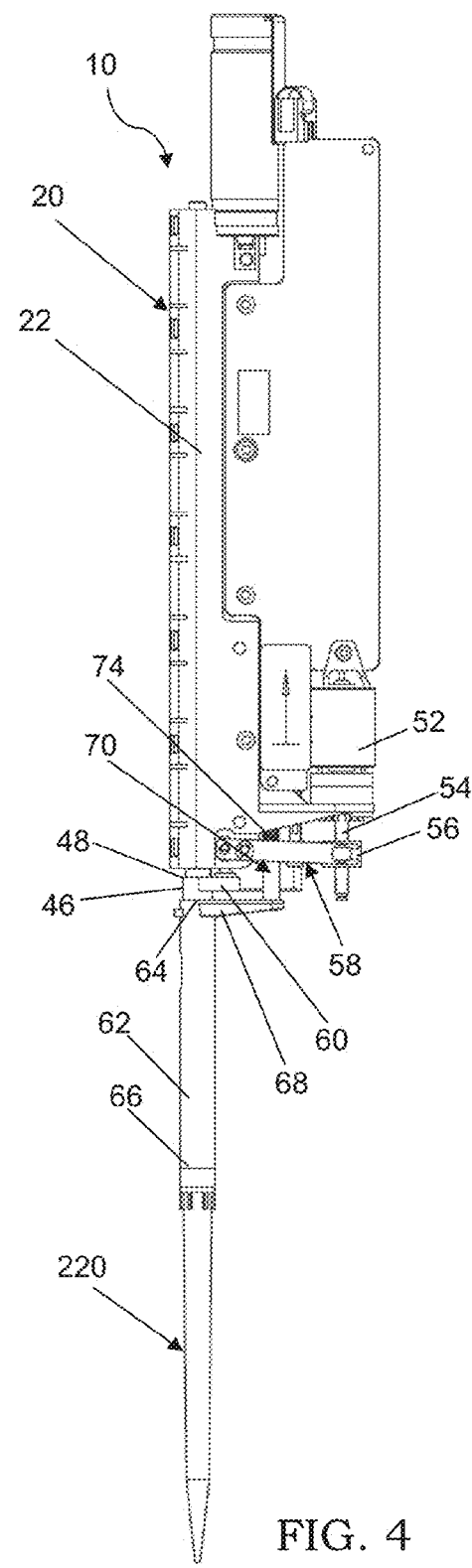
FIG. 4 is a side elevational view of an example embodiment of the pipette device assembly.

Referring to FIGS. 3 and 4, the pipette device 20 further comprises a hollow piston or squeeze sleeve 46 having a proximal or upper end 48 and a distal or lower end 50. The squeeze sleeve 46 circumscribes both the plunger cylinder 30 and the aspirating and dispensing cylinder 34 and is operatively coupled to a squeeze motor 52.

As illustrated in FIG. 4, the squeeze motor 52 of pipette device assembly 10 is supported on the body 22 of the device 20 and is operatively coupled to and drives a lead screw 54 that couples to an axially translating lead nut 56 that is operatively coupled to a squeeze linkage 58. Additionally, the squeeze linkage 58 is operatively coupled to the proximal or upper end 48 of squeeze sleeve 46 via squeeze linkage arm 60 such that rotation of the squeeze motor 52 in a first direction results in linear axial translation of squeeze sleeve 46 in a distal or vertically downward direction along longitudinal channel axis 80 to abut an annular wedge or squeeze ring 210 (FIG. 5) of the coupler 100 as described below. Subsequent rotation of the squeeze motor 52 in a second or opposite direction results in linear counter axial translation of the squeeze sleeve 46 in a proximal or vertically upward direction opposite the distal or vertically downward direction along longitudinal channel axis 80.

Ejection Sleeve 62

Referring to FIG. 4, the pipette device 20 further comprises an ejection sleeve 62 used to eject the disposable pipette tip 220 from the pipette device 20 wherein the ejection sleeve 62 is axially movable relative to the aspirating and dispensing cylinder 34 (FIG. 2) and comprises a proximal or upper end 64, a distal or lower end 66, and an ejection sleeve arm 68 attached at a first end to the ejection sleeve 62 adjacent upper end 64 and having an opposing second end attached to a first end of a plunger device 70.

Figure 5:
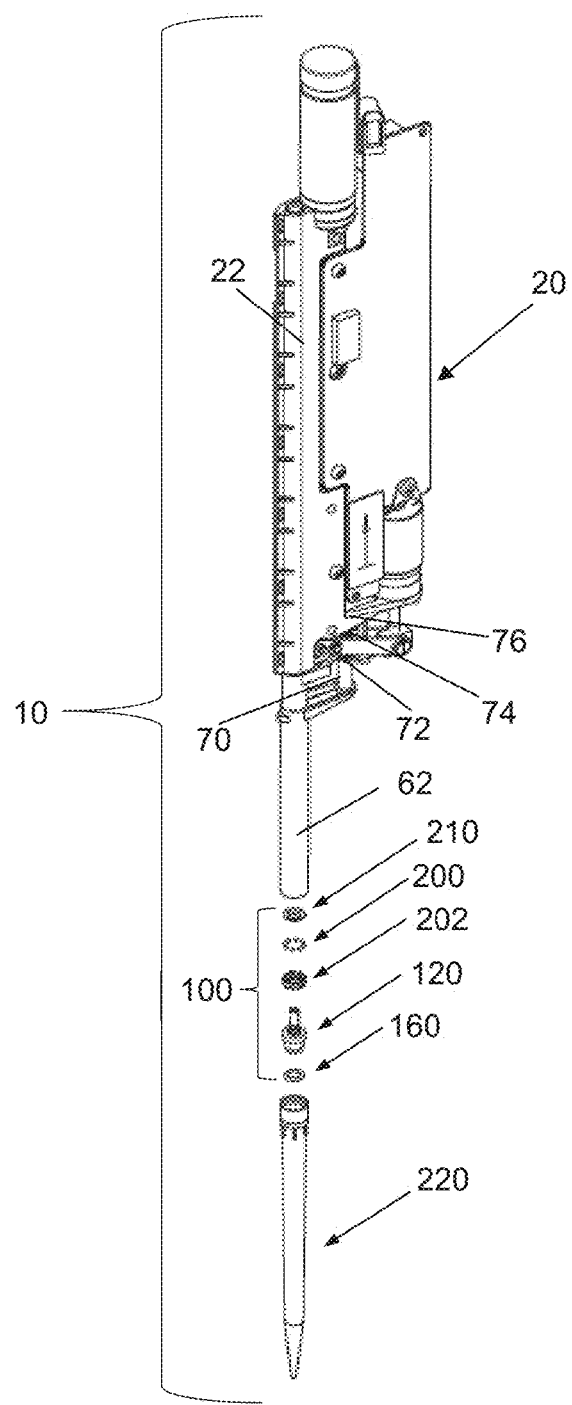
FIG. 5 is a partial exploded parts perspective view of an example embodiment of the pipette device assembly detailing parts of an example embodiment of the pipette tip coupler device.

As illustrated in FIG. 5, the plunger device 70 comprises an opposing end surface 72 abutting one end of an ejection sleeve spring 74 having an opposing spring end abutting against an upper surface portion 76 of the body 22 of device 20 wherein the ejection sleeve spring 74 is captured between the surfaces 72, 76 to be spring loaded to bias the plunger device 70 and attached sleeve 62 in a typical pipette tip ejected state.

FIG. 2 illustrates the retracted state of the ejection sleeve 62. The typical pipette tip ejected state is configured to require a force, such as coupling to pipette tip 220, to overcome the ejection sleeve spring force in order to axially push the ejection sleeve 62 to a retracted state as illustrated in FIG. 2. Additionally, FIG. 2 illustrates that the spring 74 circumscribes a central spring guide member 78 for retaining the shape of the spring 74 and for preclude the spring 74 from buckling.

Furthermore, the spring 74 is dimensioned in such a way that the force exerted on the pipette tip 220 by sleeve 62 in the course of its relaxation is sufficient to assist in ejecting the tip 220 from the pipette tip coupler 100.

It should be appreciated that the pipette tip coupler 100 (and coupler 1100 detailed below) and the disposable pipette tip 220 can be practiced on other embodiments of pipette devices wherein the embodiment of pipette device 20 is provided by way of example only and not limitation.

Pipette Tip Coupler 100

FIG. 5 illustrates an example embodiment of the segment and seal pipette tip coupler device 100 interposed between the disposable pipette tip 220 and the air displacement pipette device 20 of the air displacement pipette device assembly 10.

Figure 6:
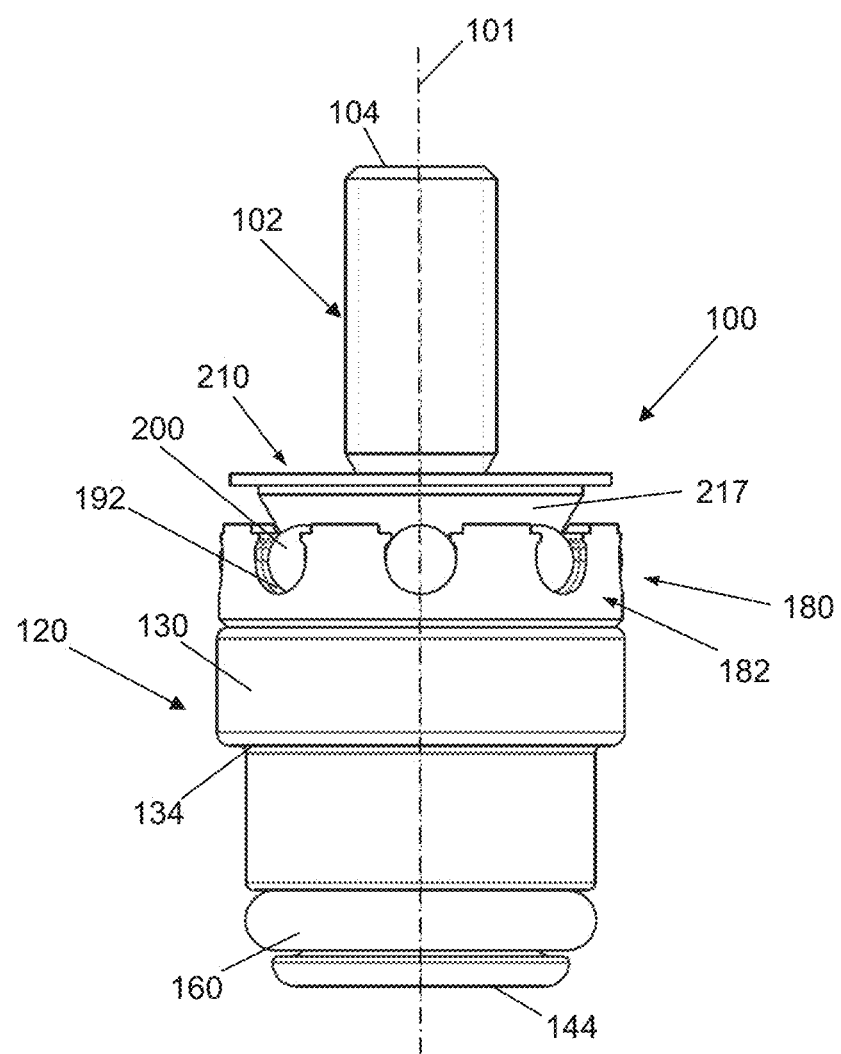
FIG. 6 is a side elevational view of an example embodiment of the pipette tip coupler device.
Figure 7:
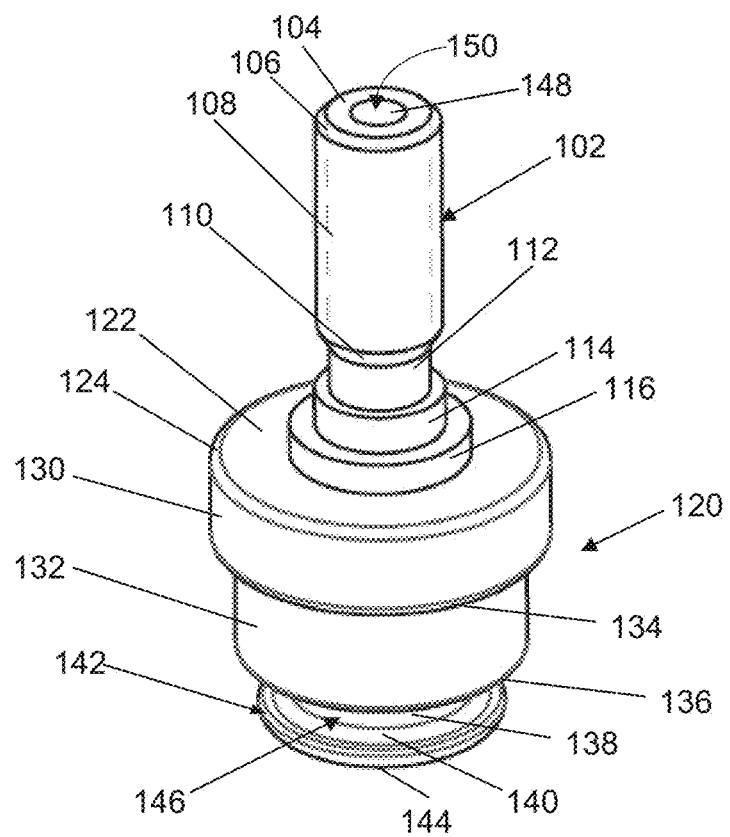
FIG. 7 is a top and side perspective view of an example embodiment of a pipette tip coupler body of an example embodiment of the pipette tip coupler device.

As illustrated in FIGS. 5 through 7, the example embodiment of the segment and seal pipette tip coupler device 100 is in the form of a ball pipette tip coupler device 100. In particular, the pipette tip coupler 100 comprises a pipette tip coupler body 120 and a distal stem portion 138, a distal elastomeric element 160 carried on the distal stem portion 138, a segment or ball coupling system 180 carried at a proximate or upper end portion of the pipette tip coupler body 120 and comprising a plurality of circumferentially spaced apart spherical balls 200 and a segment or ball retainer 182 for retaining and allowing movement of the plurality of spaced apart spherical balls 200, and annular wedge or squeeze ring 210 surmounting the plurality of spherical balls 200.

Referring to FIGS. 6 and 7, and in one example embodiment, the pipette tip coupler 100 also comprises an elongated head or shank member 102 surmounting the pipette tip coupler body member 120. The pipette tip coupler 100 further comprises the plurality of spherical balls 200 carried spaced apart circumferentially at a proximate or upper end portion of the pipette tip coupler body 120 by the segment or ball retainer 182 and the lower or distal elastomeric element 160 carried at a distal or lower end portion of the pipette tip coupler body 120. Moreover, the pipette tip coupler 100 comprises an annular wedge or squeeze ring 210 surmounting the plurality of spherical balls 200 carried by the segment or ball retainer 182 such that the plurality of spherical balls 200 are interposed between the pipette tip coupler body 120 and the annular wedge squeeze ring 210 and radially moveable within the segment or ball retainer 182 between a radially retracted position and a radially extended position as a function of the axial location of the annular wedge or squeeze ring 210.

Shank Member 102

Referring to FIGS. 6 and 7, and in one example embodiment, shank member 102 comprises an annular proximal end face 104 defining a proximal or upper end face of the pipette tip coupler 100. End face 104 comprises an outer periphery 106 that can be chamfered and that transitions into elongated tubular body 108.

Distal from proximal end face 104, the elongated tubular body 108 transitions into an annular tapered portion 110 that decreases in diameter and transitions into a cylindrical neck portion 112. The cylindrical neck portion 112 distally transitions into a cylindrical collar 114 that has a diameter greater than a diameter of the cylindrical neck portion 112. The cylindrical collar 114 is distally followed by a second cylindrical collar 116 that has a diameter greater than a diameter of the cylindrical collar 114 and that surmounts an inner portion of an upper circular body end surface 122 of the pipette tip coupler body 120. The second cylindrical collar 116 is an annular spacer, which may be integrated with shank member 102. Alternatively, the second cylindrical collar 116 may be replaced with a separate, removable annular spacer.

Pipette Tip Coupler Body 120 and Distal Stem Portion 138

As illustrated in FIG. 7, the pipette tip coupler body 120 comprises the superior or upper end surface 122 that radially and outwardly extends from the distal end of the second cylindrical collar 116 and transitions into an outer peripheral edge 124 that is rounded. In one example embodiment, the upper circular body end surface 122 is a substantially planar surface that radially outwardly extends from the distal end of the second cylindrical collar 116 to the outer peripheral edge 124.

Additionally, coupler body 120 comprises a multi-cylindrical section comprising a first cylindrical or stop disk portion 130 that distally extends axially away from upper end surface 122 and that is distally followed by a second cylindrical portion 132 that is reduced in diameter for forming a distally or downwardly facing axial shoulder surface or stop shoulder surface 134 between the adjoining first and second cylindrical portions 130, 132.

As illustrated in FIG. 7, the second cylindrical portion 132 distally extends from the stop shoulder surface 134 to a distally lower surface 136 that radially inwardly transitions into a reduced diameter distal cylindrical stem portion 138 that terminates to a radially outwardly extending upper surface 140 of an end plate 142 that is generally round. The end plate 142 comprises a rounded peripheral edge that provides a circumferential rounded transition between the upper surface 140 of the end plate 142 and a lower generally planar surface 144 of end plate 142 defining the distal end face of the pipette tip coupler body 120 of pipette tip coupler 100.

As illustrated in FIGS. 6 and 7, and as noted above, the second cylindrical portion 132 is reduced in diameter relative to the first cylindrical portion 130. Thus, the first cylindrical portion 130 has a first diameter that is greater than a second diameter of the second cylindrical portion 132 for forming the distally facing axial shoulder surface or stop shoulder surface 134 between the first and second cylindrical portions 130, 132.

Furthermore, the second diameter of the second cylindrical portion 132 is greater than a diameter of the end plate 142. In turn, a diameter of the distal cylindrical stem portion 138 is less than both the second diameter of the second cylindrical portion 132 and the diameter of the end plate 142 for defining a lower, distal groove 146 between the second cylindrical portion 132 and the end plate 142. In one example embodiment, the first and second cylindrical head portions 130 and 132 respectively comprise generally smooth exterior cylindrical surfaces and the distal cylindrical stem portion comprises a generally smooth exterior cylindrical or groove surface.

Figure 13:
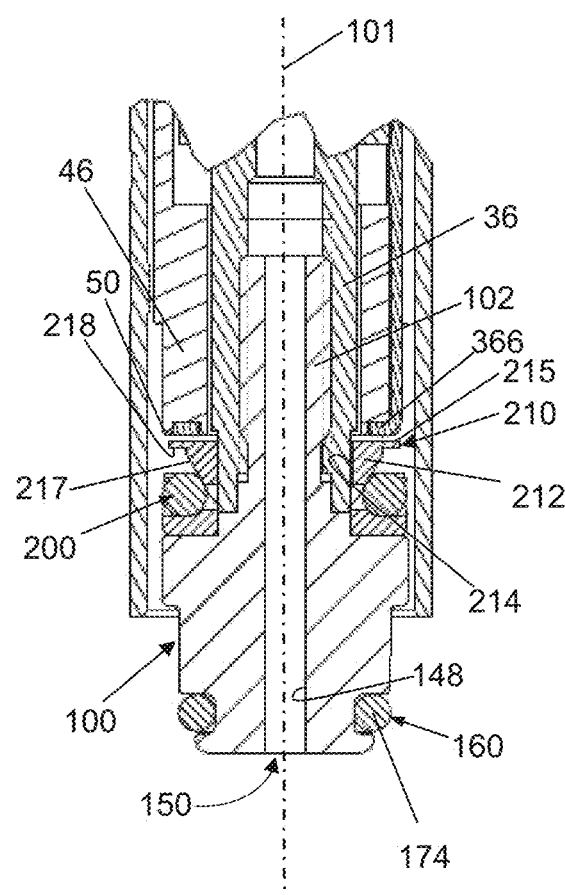
FIG. 13 is a fragmentary, longitudinal sectional, side elevational view of an example embodiment of the pipette device operatively coupled to the example embodiment of the pipette tip coupler device.

Referring to FIGS. 7 and 13, the pipette tip coupler 100 further comprises an open ended, interior cylindrical channel surface 148 that defines an open ended cylindrically shaped central channel 150 that runs along the longitudinal central axis 101 of the pipette tip coupler 100 from the annular proximal or upper end face 104 defining the proximal end face of the pipette tip coupler 100 to the lower generally planar surface 144 defining the distal end face of the pipette tip coupler 100. The open ended cylindrically shaped central channel 150 provides open communication between the aspirating and dispensing cylinder 34 (FIG. 3) and the pipette tip 220 wherein the aspirating and dispensing cylinder 34 is also in open communication with the aspirating and dispensing plunger 26 (FIG. 3).

Distal or Lower Elastomeric Element 160

Referring to FIGS. 6 and 7, and as noted above, the pipette tip coupler 100 comprises the ball coupling system 180 carried at the upper end portion of coupler body 120 and the lower or distal elastomeric element 160 carried at the lower end portion of coupler body 120 axially distally spaced from the ball coupling system 180 by way of the distal cylindrical stem portion 138.

Figure 8:
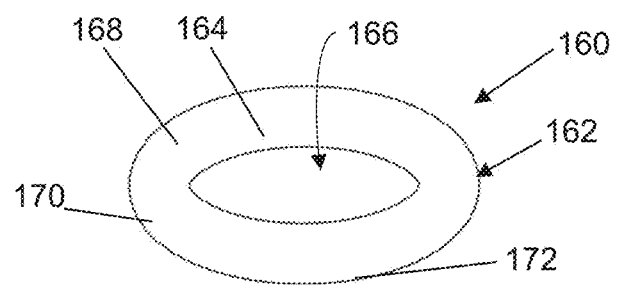
FIG. 8 is a top and side perspective view of an example embodiment of a distal elastomeric element or O-ring of an example embodiment of the pipette tip coupler device.

Referring to FIG. 8, and in one example embodiment, the lower elastomeric element 160 comprises an annular body 162 having an interior surface 164 defining a central opening 166. The lower elastomeric element 160 further comprises a top surface 168, a peripheral exterior surface 170, and a bottom surface 172. In a relaxed or unsqueezed state, the lower elastomeric element 160 comprises a circumferentially continuous, generally circular cross section area 174 as is illustrated in FIG. 13. Alternatively, the elastomeric element may have a rectangular, X-shaped, square-shaped, or other cross sectional area.

Referring to FIGS. 7 and 8, the central opening 166 of the lower elastomeric element 160 is dimensioned to tightly circumscribe the distal cylindrical stem portion 138 of the pipette tip coupler 100 between the distally lower surface 136 of the second cylindrical portion 132 and the upper surface 140 of the end plate 142 of the pipette tip coupler body member 120 wherein the surfaces 136,140 are in the form of, but not limited to, a planar, conical or concave configuration.

Segment or Ball Coupling System 180

Referring to FIG. 6, and in one example embodiment, the segment or ball coupling system 180 comprises an annular crown shaped raceway 182 comprising a plurality of circumferentially spaced apart guide sockets or surfaces 192 each carrying one of a plurality of segments or spherical balls 200.

Figure 9:
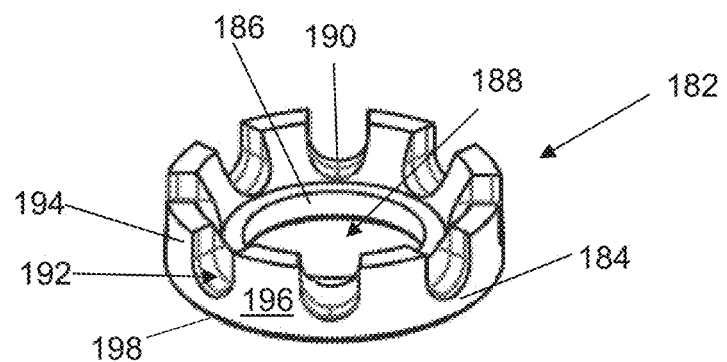
FIG. 9 is a top and side perspective view of a crowned shaped ball raceway of an example embodiment of the pipette tip coupler device, the raceway comprising a plurality of circumferentially spaced apart guide sockets each configured to receive a spherical ball or discrete coupling element or segment.

Referring to FIG. 9, the annular crown shaped raceway 182 comprises an annular base 184 having an interior surface 186 defining a central opening 188, an upper surface 190 configured with the plurality of circumferentially spaced apart guide sockets 192 with each adjacent pair of guide sockets 192 separated by one of a plurality of intervening fingers 194. The annular crown shaped raceway 182 further comprises a peripheral exterior surface 196 and a bottom surface 198.

Figure 10:
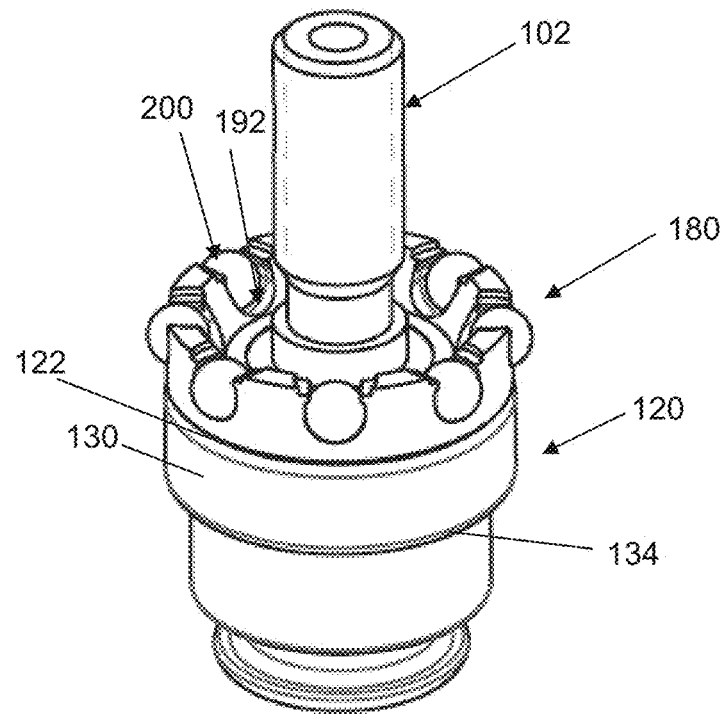
FIG. 10 is a top and side perspective view of the crowned shaped ball raceway with a spherical ball or discrete coupling element or segment received within each of the plurality of circumferentially spaced apart guide sockets.

Referring to FIG. 10, the segment or ball retainer 182 surmounts body 120 by having a seating abutment of at least the bottom surface 198 of the annular crown shaped raceway 182 with the upper end surface 122 (FIG. 7) of the stop disk portion 130 of the pipette tip coupler body 120 wherein each of the plurality of segments or spherical balls 200 is disposed in a different one of the plurality of the circumferentially spaced apart guide sockets 192.

Figure 11:
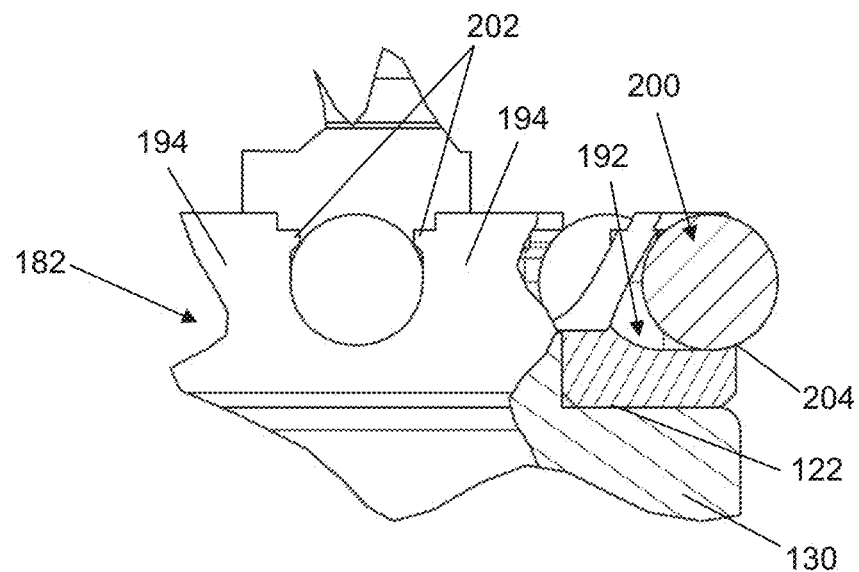
FIG. 11 is a fragmented and cutaway, longitudinal sectional, side elevational view of a portion of the crowned shaped ball raceway and a segment or ball received within the raceway.

As illustrated in FIG. 11, the spherical balls 200 are captured vertically by a pair of opposed inwardly projecting stakes 202 disposed at the upper most portion of a plurality of adjacent pairs of the plurality of intervening fingers 194 of the annular crown shaped raceway body 182. Additionally, each of the spaced apart guide sockets 192 comprises a grooved or concaved socket seat having an outer sidewall radius 204 that capture the balls horizontally along with width dimensions of the U-shaped ball openings defined by the spaced apart guide sockets 192 and intervening fingers 194. The spaced apart guide sockets 192 are configured for carrying radially advancing and retracting balls on the guide sockets 192 for attachment and detachment of the tip 220.

Accordingly, and with reference to FIGS. 10 and 11, the segment or ball coupling system 180, comprising the raceway 182 and the plurality of spherical balls 200, disposed on the upper end surface 122 of the stop disk portion 130 of the pipette tip coupler body 120 retains the plurality of spherical balls or segments and allows movement of the spherical balls or segments between extended and retracted position. The segment or ball coupling system 180 may be operatively fitted on or integrally formed operatively with upper end surface 122 of the stop disk portion 130 of the pipette tip coupler body 120.

Annular Wedge or Squeeze Ring 210

Figure 12:
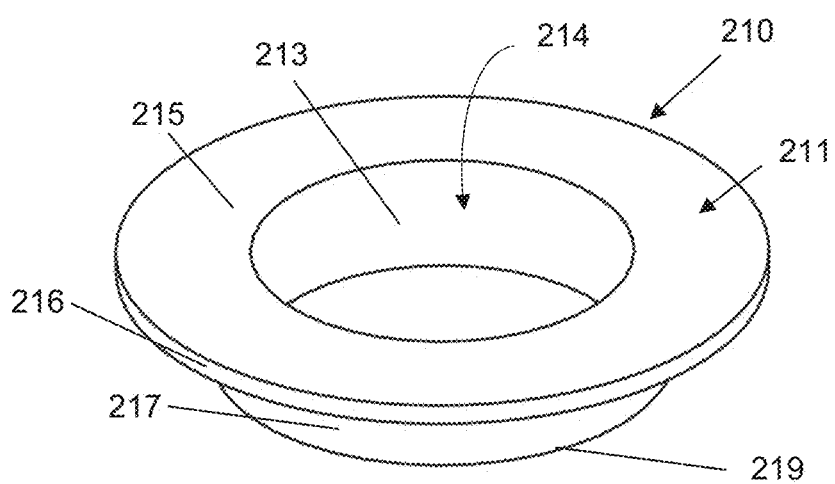
FIG. 12 is a top and side perspective view of the annular wedge or squeeze ring of an example embodiment of the pipette tip coupler device.

Referring to FIGS. 12 and 13, an embodiment of the pipette tip coupler 100 comprises the annular wedge or squeeze ring 210. Squeeze ring 210 comprises a resilient wedge shaped annular body 211 having a circumferentially continuous, generally wedge shaped or triangular shaped cross section 212 with a radially extending annular lip 218 as illustrated in FIG. 13. As illustrated in FIG. 12, annular body 211 comprises a central interior annular surface 213 defining a central annular opening 214 extending through the annular body 211. Furthermore, wedge shaped annular body 211 comprises a top planar circular surface 215 radially outwardly extending from the central interior annular surface 213 to a circumscribing outer edge surface 216. Moreover, wedge shaped annular body 211 comprises a radially outwardly proximally inclined side surface 217 radially upwardly tapering from a bottom annular end 219 to an underside of annular peripheral lip 218 (FIG. 13) that radially extends outwardly and terminates to circumscribing outer edge surface 216.

As illustrated in FIG. 13, the central annular opening 214 of the annular wedge or squeeze ring 210 is dimensioned to allow passage of the shank member 102 so as to allow a seating abutment of radially outwardly proximally inclined side surface 217 of the annular wedge or squeeze ring 210 with, as illustrated in FIG. 6, the plurality of segments or spherical balls 200 of the segment or ball coupling system 180 carried on the upper end surface 122 (FIG. 7) of the stop disk portion 130 of the pipette tip coupler 100.

Referring to FIG. 13, the shank member 102 of the pipette tip coupler 100 is configured to fit within the distal mounting flange 36 of the aspirating and dispensing cylinder 34 (FIG. 2) for operatively coupling the pipette tip coupler 100 to the pipette device 20 of the pipette device assembly 10 and aligning axis 101 (FIG. 6) of the coupler 100 with axis 98 (FIG. 14) of the pipette device 20. In one embodiment, the elongated tubular body 108 of the shank member 102 is externally threaded to mount, or screw, into distal mounting flange 36 that has mating internal threads.

Actuation of Squeeze Motor

With the pipette tip coupler 100 fitted within the distal mounting flange 36 as illustrated in FIG. 13, the top planar circular surface 215 of the annular wedge or squeeze ring 210 is adjacent the distal end 50 of the squeeze sleeve 46. Accordingly, actuation of the squeeze motor 52 (FIG. 1) in the first direction results in linear axial translation of the squeeze sleeve 46 in a distal or vertically downward direction for applying a force axially on the top surface 215 of the annular wedge squeeze ring 210 via a liquid level detection (LLD) circuit ring end 366 detailed below for forcing the wedge shaped bottom 217 to push uniformly against the inner surfaces of plurality of spherical balls 200 for pushing them radially out and into a groove 246 (FIG. 16) of the disposable pipette tip 220 and into contact with surface 244 (FIG. 16) as exemplified in FIG. 23 described below.

Figure 16:
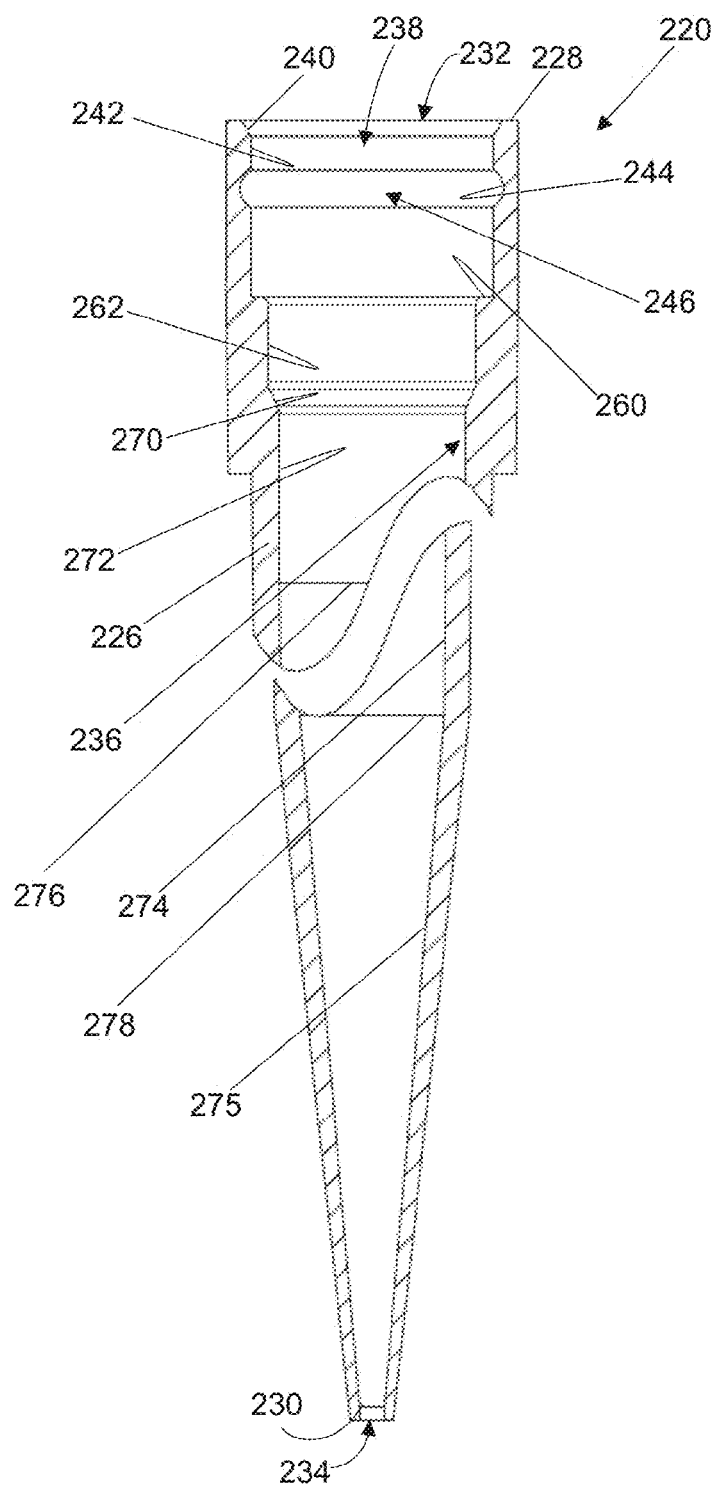
FIG. 16 is a fragmentary, longitudinal sectional, side elevational view detailing the interior of an example embodiment of the disposable pipette tip.

Subsequent actuation of the squeeze motor 52 (FIG. 1) in a second direction, opposite the distal or vertically downward direction, returns the distal end 50 of the squeeze sleeve 46 to a home position as illustrated in FIG. 13 such that the annular wedge or squeeze ring 210 axially slides up thereby allowing the plurality of segments or spherical balls 200 to freely radially retract on respective spaced apart grooved or concave guide sockets 192 (FIG. 11) from the groove 246 (FIG. 16) of the disposable pipette tip 220 (FIG. 16). Thus, when the eject sleeve 62 (FIG. 13) pushes on the tip 220 (FIG. 16), the surface 244 (FIG. 16) of the groove 246 and the interior circumferential surface axially above the groove 246 push upon contact of the segments or spherical balls 200 thereby causing the segments or spherical balls 200 to retract.

Pipette Tip 220

Figure 14:
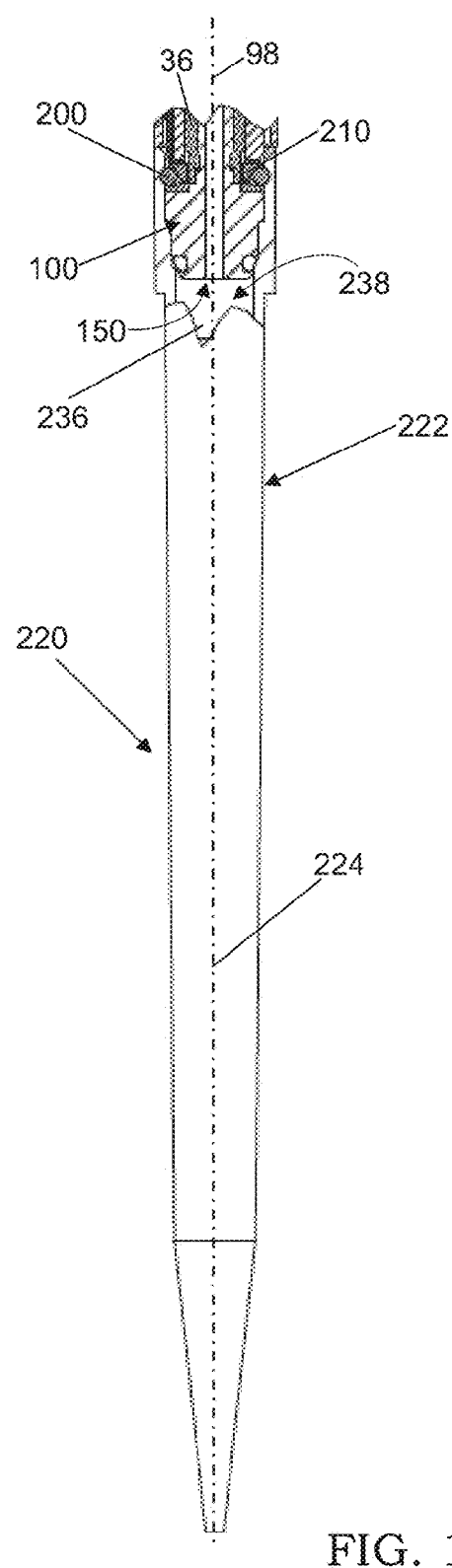
FIG. 14 is a fragmentary, partially sectional, side elevational view of an example embodiment of the pipette device operatively coupled to an example embodiments of the pipette tip coupler device and tip.

As illustrated in FIGS. 2 and 14, and as noted above, the pipette tip coupler 100 provides an open communication coupling between the disposable pipette tip 220 and the pipette device 20 of the pipette device assembly 10.

Figure 15:
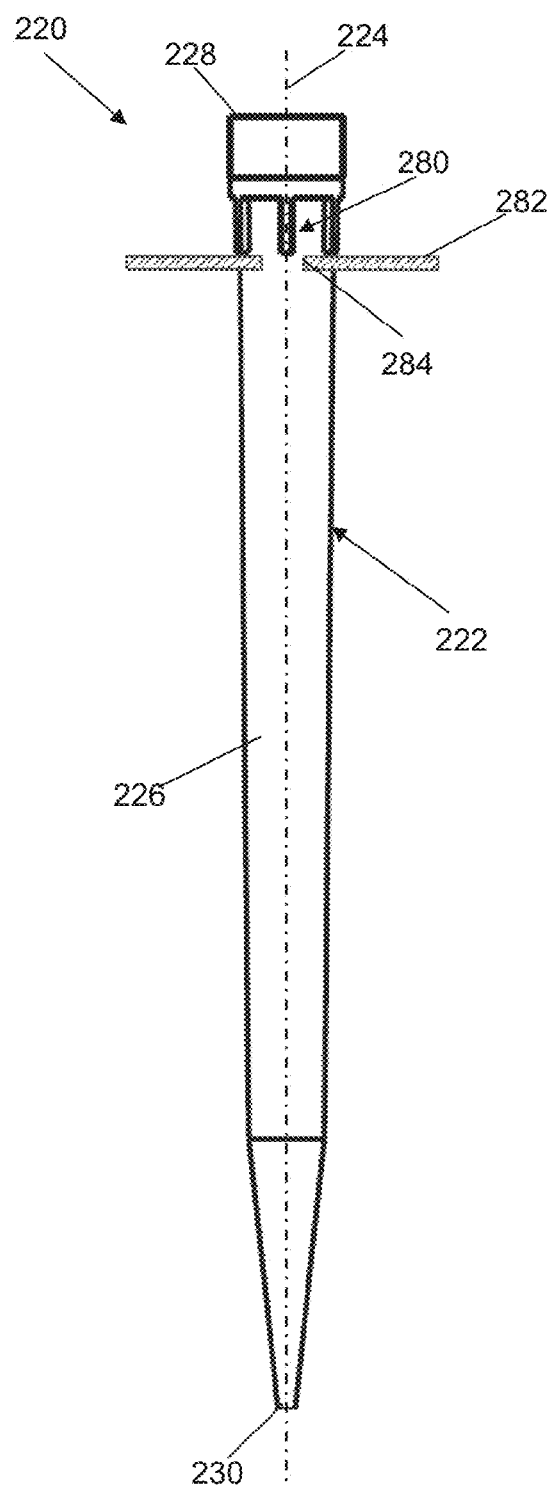
FIG. 15 is a side elevational view of an example embodiment of the disposable pipette tip illustrated in a supported position.

Referring to FIGS. 14 through 16, and in one example embodiment, the disposable pipette tip 220 comprises an elongated tubular pipette tip body 222 having a central longitudinal axis 224. Pipette tip body 222 comprises an elongated circumscribing sidewall 226 longitudinally extending along the central longitudinal axis 224 between a proximal or upper annular end face 228 and a distal or lower annular end face 230 defining circumscribing open proximal and distal annular ends 232 and 234 respectively. The elongated circumscribing sidewall 226 comprises an interior surface 236 defining a pipette tip passage opening 238 extending longitudinally along the central longitudinal axis 224 of the pipette tip body 222 between the open upper annular end 232 and the open lower annular end 234.

Accordingly, the pipette tip passage opening 238 provides open communication from an area exterior to the open distal annular end 234 (FIG. 16), through the pipette tip 220, and to the pipette device channel 40 by way of the central channel 150 of the pipette tip coupler 100 (FIG. 3) when the pipette tip coupler 100 is coupled between the pipette device 20 and the pipette tip 220. In this coupling configuration, the central longitudinal axis 224 of the pipette tip body 222 is coextensive with the longitudinal channel axis 80 of the pipette device 20.

First Interior Surface Section

Referring to FIG. 16, and in one example embodiment, the interior surface 236 of the elongated circumscribing sidewall 226 comprises an uppermost annular chamfered interior surface 240 that distally extends radially inward from the proximal annular end face 228 of the pipette tip 220 and terminates by transitioning into a first substantially cylindrical interior surface section 242 having a first diameter.

Axially Arcuate Circumferential Surface Defining a Groove

As illustrated in FIG. 16, and in one example embodiment, the first substantially cylindrical interior surface section 242 comprises an axially arcuate circumferential interior surface 244 formed into the elongated circumscribing sidewall 226 defining a circumferential annular groove 246. Annular groove 246 divides the first substantially cylindrical interior surface section 242 into an upper first substantially cylindrical interior surface portion and a lower first substantially cylindrical interior surface portion of substantially equal diameter. Accordingly, the annular groove 246 provides a circumferential radially outwardly extending concavity shaped interior surface interruption of the first substantially cylindrical interior surface section 242 with an arcuate surface longitudinal cross section. The arcuate circumferential interior surface 244 is also configured in alternative surface cross sections as discussed below. And in one embodiment, the first substantially cylindrical interior surface section 242 is devoid of arcuate circumferential interior surface 244 defining the circumferential annular groove 246 as discussed below.

Figure 17:
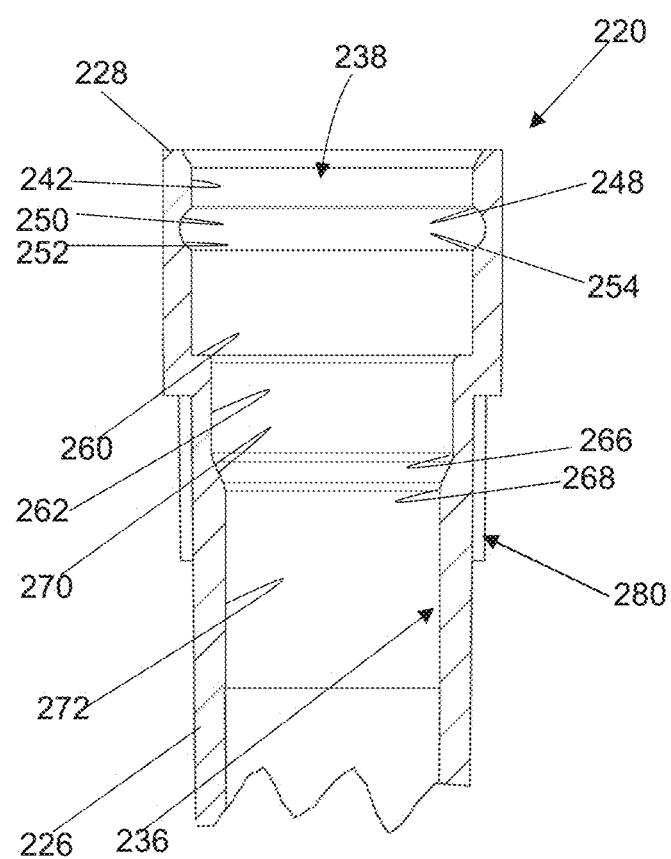
FIG. 17 is an upper detail fragmentary, longitudinal sectional, side elevational view detailing the upper interior of an example embodiment of the disposable pipette tip.

Referring to FIGS. 16 and 17, the axially arcuate circumferential interior surface 244 defining the annular groove 246 comprises an upper annular transition edge 248 distally transitioning into an upper axially arcuate circumferential surface sector portion 250 of the axially arcuate circumferential interior surface 244. In succession, the upper axially arcuate circumferential surface sector portion 250 distally transitions into a lower axially arcuate circumferential surface sector portion 252 of the axially arcuate circumferential surface 244. Then, lower axially arcuate circumferential surface sector portion 252 terminates to a lower annular transition edge 254.

The upper axially arcuate circumferential surface sector portion or upper portion 250 provides the annular groove 246 with an increasing radius relative to the central longitudinal axis 224 of the pipette tip 220 from the upper annular transition edge 248 to a maximum radius of the annular groove 246 relative to the central longitudinal axis 224 that defines a circumferential annular center of the annular groove 246.

The lower axially arcuate circumferential surface sector portion or lower portion 252 provides the annular groove 246 with a decreasing radius relative to the central longitudinal axis 224 of the pipette tip 220 from the maximum radius defining the circumferential annular center of the of the annular groove 246 to the lower annular transition edge 254.

Second Interior Surface Section and Annular Shoulder Stop Surface

As illustrated in FIG. 16, the first substantially cylindrical interior surface section 242 is axially distally proceeded by a second substantially cylindrical interior surface section 262 having a second diameter less than the first diameter of the first substantially cylindrical interior surface section 242 for forming a proximally facing, radially inwardly extending annular shoulder seat surface or axial stop surface 260 interposed between the first and second substantially cylindrical interior surface sections 242, 262.

In one example embodiment, the proximally facing axial stop surface 260 is substantially planar and generally perpendicular to the central longitudinal axis 224 of the pipette tip body 222.

Third Interior Surface Section and Sealing Seat

As illustrated in FIG. 17, the second substantially cylindrical interior surface section 262 is axially distally proceeded by a third substantially cylindrical interior surface section 272 having a third diameter less than the second diameter of section 262.

Interposed between the second section 262 and the third section 272 is a frustoconical annular sealing seat or stop surface 270 defining a circumferential radially inwardly angled and distally extending distal working surface 270 as illustrated in FIG. 17. The frustoconical annular sealing seat surface 270 comprises an upper annular sealing seat edge 266 defining an annular border between the second substantially cylindrical interior surface section 262 and the frustoconical annular sealing seat surface 270.

In addition, the frustoconical annular sealing seat surface 270 comprises a lower annular sealing seat edge 268 defining an annular boarder between the frustoconical annular sealing seat surface 270 and the third interior surface section 272 wherein a diameter of the upper annular sealing seat edge 266 is greater than a diameter of the lower annular sealing seat edge 268.

Accordingly, the frustoconical annular sealing seat surface 270 defines the circumferential radially inwardly angled and distally extending distal working surface, abutment, or sealing seat surface 270 interposed between the second substantially cylindrical interior surface section 262 and the third substantially cylindrical interior surface section 272.

As illustrated, the sealing seat surface 270 is disposed at an acute angle relative to the central longitudinal axis 224 wherein the acute angle defines an acute sealing seat surface angle relative to the central longitudinal axis 224. In one embodiment, the preferred acute sealing seat surface angle relative to the central longitudinal axis 224 is about 15 degrees to about 35 degrees with a preferred angle of about twenty-five degrees.

Figure 76:
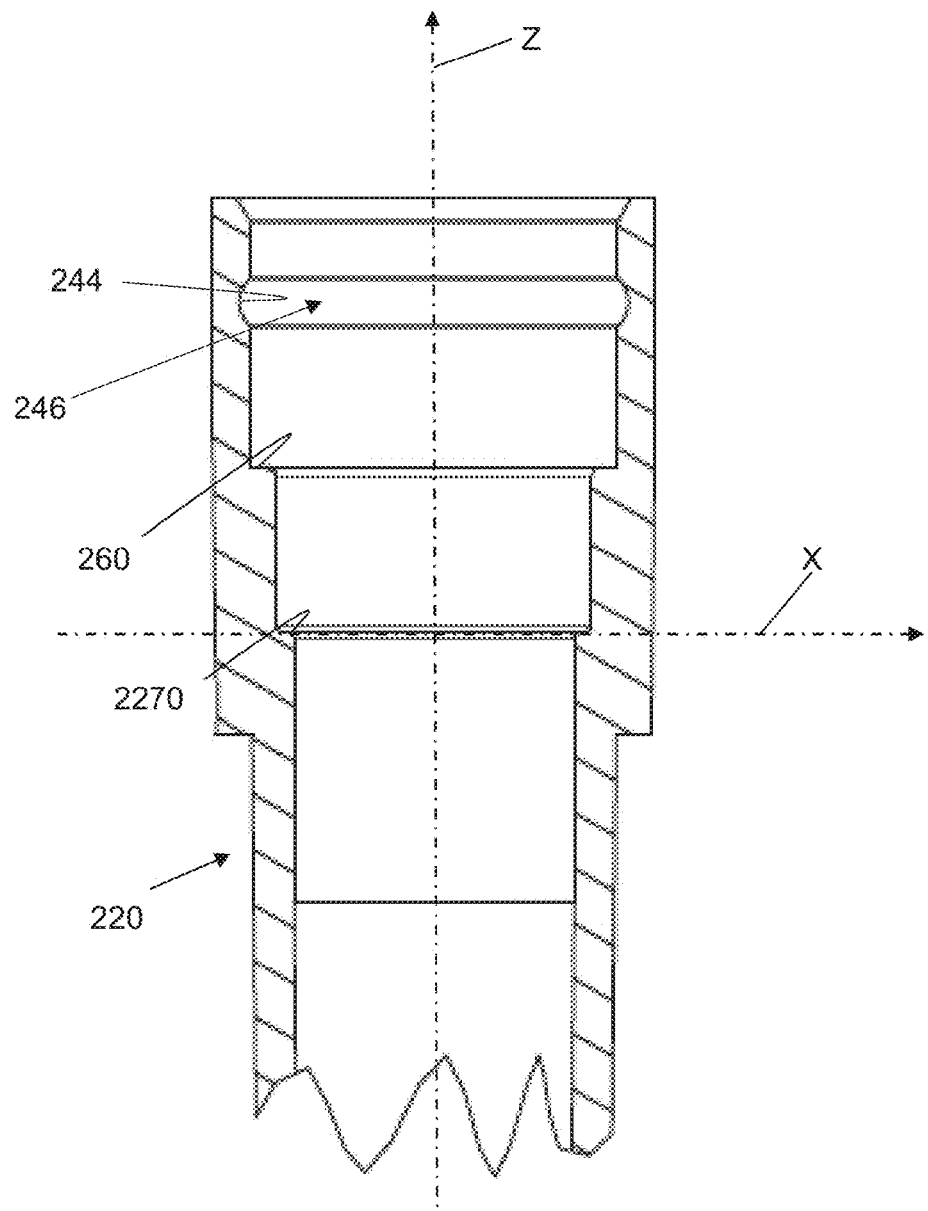
FIG. 76 is a fragmentary, longitudinal sectional, side elevational view of an example embodiment of the disposable pipette tip comprising an alternative sealing seat surface angle of substantially ninety degrees relative to the central longitudinal axis of the pipette tip.

In one alternative embodiment, the sealing seat surface 270 is provided with an alternative sealing seat surface angle of substantially ninety degrees relative to the central longitudinal axis of the pipette tip. This embodiment is illustrated in FIG. 76 wherein the sealing seat surface angle of an alternative sealing seat surface 2270 relative to the central longitudinal Z-axis is substantially 90 degrees.

Lower Interior Surface Portion

FIG. 16 further illustrates that in succession to the third substantially cylindrical interior surface section 272 is a fourth interior surface section 274 that is distally followed by a fifth interior surface section 275.

In one example embodiment, the fourth interior surface section 274 distally tapers or decreases in diameter from a distal annular end 276 of the third substantially cylindrical interior surface section 272 to a proximal annular end 278 of the fifth interior surface section 275. In turn, the fifth interior surface section 275 distally tapers or decreases in diameter from the proximal annular end 278 of the fifth interior surface section 275 to the open distal annular end 234 of the pipette tip 220 that is intended for immersion. Additionally, and in one example embodiment, the fifth interior surface section 275 has a greater taper than the fourth interior surface section 274.

External Longitudinal Ribs

Referring to FIG. 15, and in one example embodiment, of the pipette tip 220 comprises a plurality of circumferential spaced apart longitudinally extending external ribs 280 disposed on the tubular pipette tip body 222 adjacent to the periphery of the proximal annular end face 228 and longitudinally extending externally therefrom to an exterior area of the circumscribing sidewall 226 that is adjacent to the third substantially cylindrical interior surface section 272 as illustrated in FIG. 16.

In one example embodiment, and as illustrated in FIG. 15, the plurality of circumferential spaced apart longitudinally extending external ribs 280 may be utilized to provide support for the pipette tip 220 on or in a support surface 282 that the pipette body 222 has passed through via, for example, a support surface aperture opening 284. One example embodiment of the support surface 282 can be in the form of, but not limited to, lab ware in the form of a tip rack as is known in the art, and informed by the present disclosure.

Automated Pipetting Workstation or System

Figure 18:
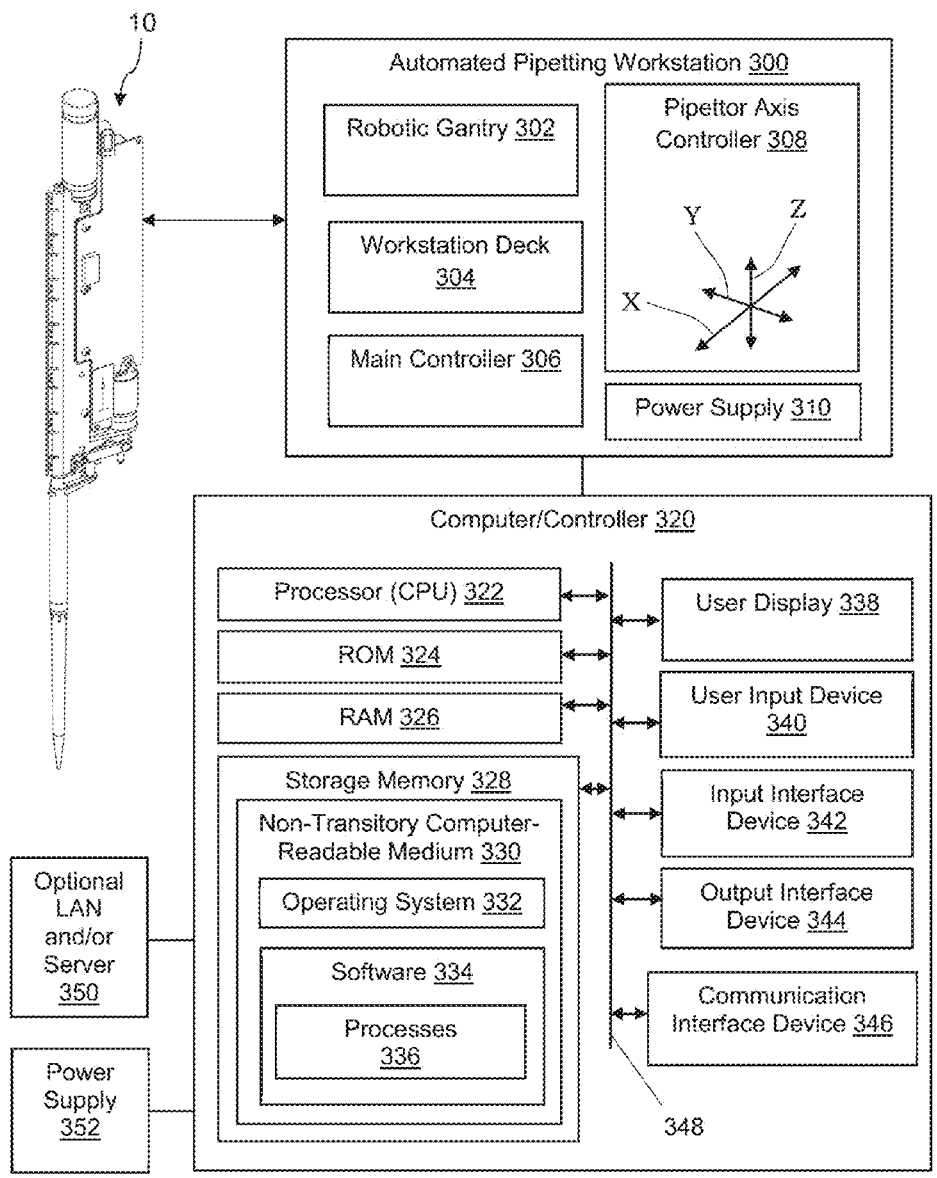
FIG. 18 is a diagrammatical block diagram view of an example embodiment of an automated pipetting workstation or system.

Referring to FIGS. 1 and 18, and in one example of use and operation, one or more of the pipette device assemblies 10 is employed in an automated pipetting workstation or system 300 that generally provides, but is not limited to, programmed transfers of liquid between containers that comprises mounting and ejection processes of one or more disposable pipette tips 220 to the pipette tip coupler 100 operatively carried by the pipette device 20 for carrying out, for example, the programmed transfers of liquid between containers.

In one example embodiment, the automated pipetting workstation 300 generally comprises a robotic gantry 302 that carries at least one pipette device assembly 10 vertically above a horizontally disposed workstation deck 304. The pipette device assembly 10 can comprise a single channel pipetting head or a multi-channel pipetting head.

Additionally, the robotic gantry 302 typically provides two or three degrees of freedom wherein three degrees of freedom comprises longitudinal translation along an axis defining an X-axis, latitudinal translation along an axis defining a Y-axis, and vertical (up and down) translation along an axis defining a Z-axis so that the pipette device assembly 10 can move along the length (X-axis) and width (Y-axis) of the deck and vertically up and down (Z-axis) relative thereto. With two degrees of freedom, the robotic gantry is typically provided with the ability to translate the pipette device assembly 10 vertically and either longitudinally or laterally.

In one example embodiment, the automated pipetting workstation 300 further comprises a main controller 306, a pipette axis controller 308, and a power supply 310 that provides power for the main controller 306, the pipette axis controller 308, and the pipette device assembly 10.

Additionally, and in one example embodiment, a computer/controller 320 can also be employed with the workstation 300 and communicate with the main controller 306 and the pipette axis controller 308 for controlling the robotic gantry 302 and pipette device assembly 10 including the associated process protocols of the pipette device assembly 10 such as the disposable pipette tip 220 attaching and ejection (coupling and decoupling) processes detailed below.

In one example embodiment, the computer/controller 320 typically comprises a processor device or central processing unit (CPU) 322, a hardware read only memory device (ROM) 324, a hardware main memory device (RAM) 326, a hardware storage memory 328 comprising a non-transitory computer readable medium or memory 330 having an operating system 332 and software 334 such as user defined processes 336 for the pipette device assembly 10 stored thereby, a user display 338, a user input device 340, an input interface 342, an output interface 344, a communication interface device 346, and a system bus 348 that comprises one or more conductor or communication paths that permit communication among the devices of the computer/controller 320. Computer/controller 320 may also be operatively couple to LAN and/or server 350. A power supply 352 provides power for the computer/controller 320.

Examples of the above delineated automated pipetting workstation 300 including software are presently manufactured and sold by Hamilton Company, the assignee of the present patent application, located at 4970 Energy Way, Reno, Nev. 89502, United States of America.

Pipette Tip Pickup Process with Pipette Tip Coupler 100

FIGS. 19 through 25 illustrate details of an example embodiment of successive stages of a pipette tip pickup process and, in particular, a method of securing attachment of the pipette tip 220 to the pipette tip coupler 100 operatively carried by the pipette device 20. As noted above, and in one example embodiment, the pipette tip 220 may be supported by the support surface 282.

Figure 19:
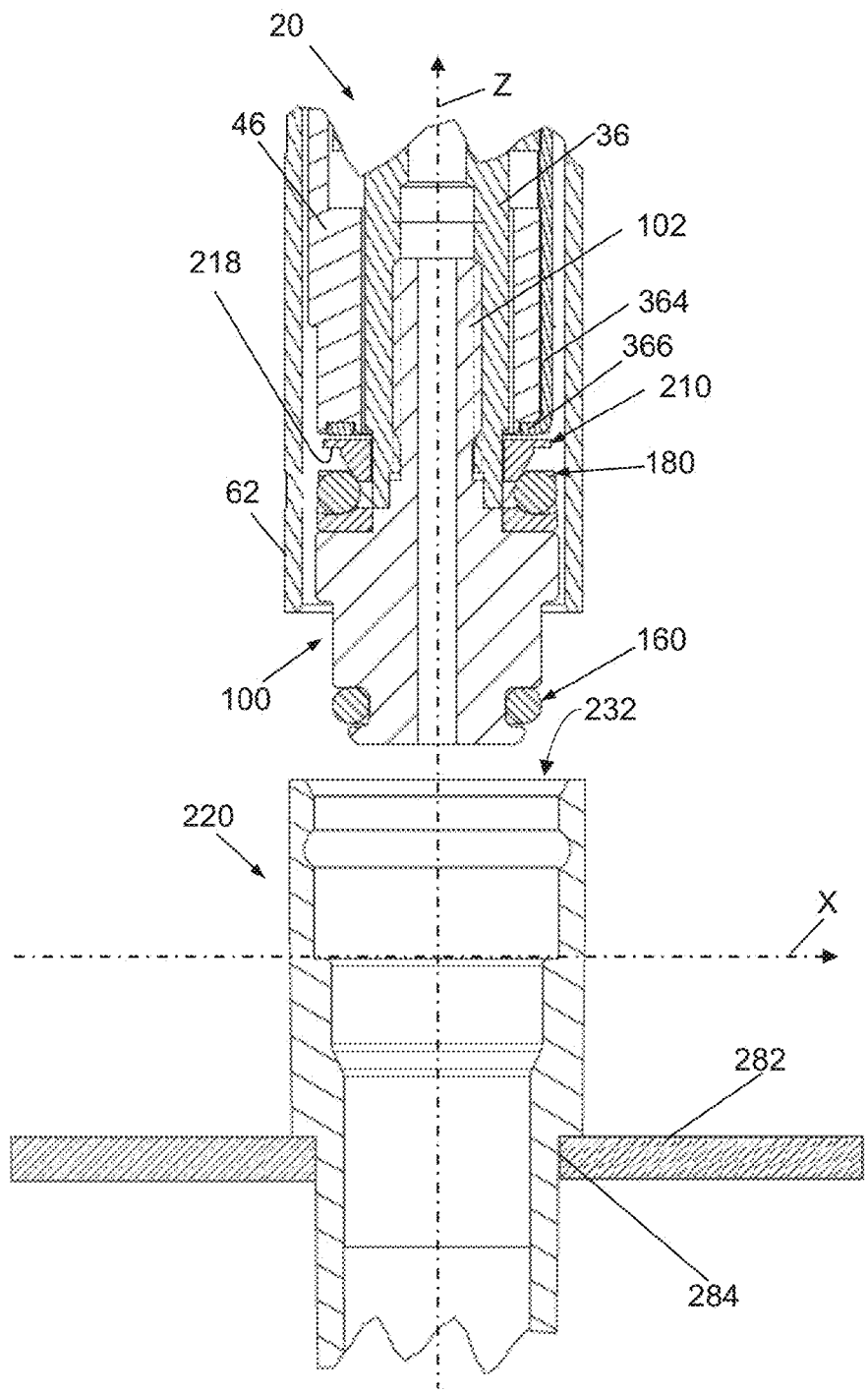
FIG. 19 is a fragmentary, longitudinal sectional, side elevational view of an example embodiment of the pipette device supporting an example embodiment of the pipette tip coupler device over an example embodiment of the disposable pipette tip.

As illustrated in FIG. 19, the pipette tip coupler 100 is connected to the pipette device 20, and upon command, the pipette tip coupler 100 is positioned over the open proximal end 232 of the pipette tip 220 wherein each of their respective central longitudinal axes is aligned along the Z-axis. The eject sleeve 62 is in the eject position, the squeeze sleeve 46 is in the unsqueezed position, the segment or ball coupling system 180 is in the relaxed state, and the distal O-ring 160 is in the unsqueezed state.

Figure 20:
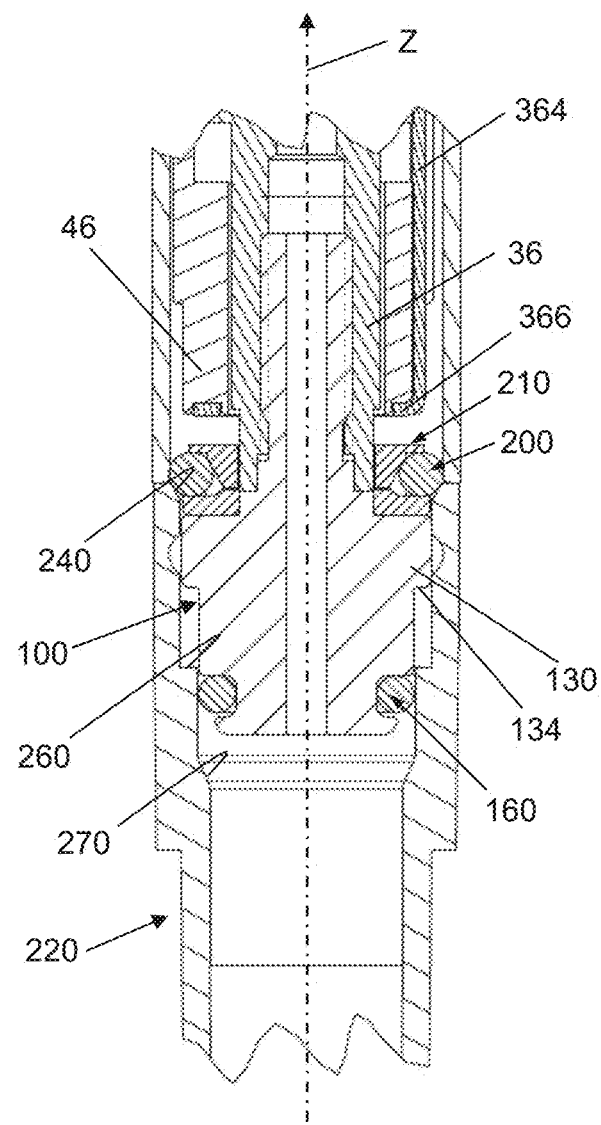
FIG. 20 is a fragmentary, longitudinal sectional, side elevational view of an example embodiment of the pipette tip coupler device positioned over and into an example embodiment of the disposable pipette tip for bringing the plurality of circumferentially spaced apart segments or balls into contact with the proximal open end of the pipette tip.

Next, FIG. 20 illustrates the pipette tip coupler 100 being moved down along the Z-axis into the pipette tip 220 for lowering the distal, elastomeric carrying portion of the pipette tip coupler 100 to pass into the interior cylindrical proximal end portions of the pipette tip 220 to bring the plurality of segments or spherical balls 200 into contact with the chamfered interior surface 240 of the tip 220 tip while maintaining the distal O-ring 160 in the unsqueezed state and before the annular shoulder seat or stop surface 260 of the pipette tip 220 and the axial stop shoulder surface 134 of the stop disk 130 are mated.

Figure 21:
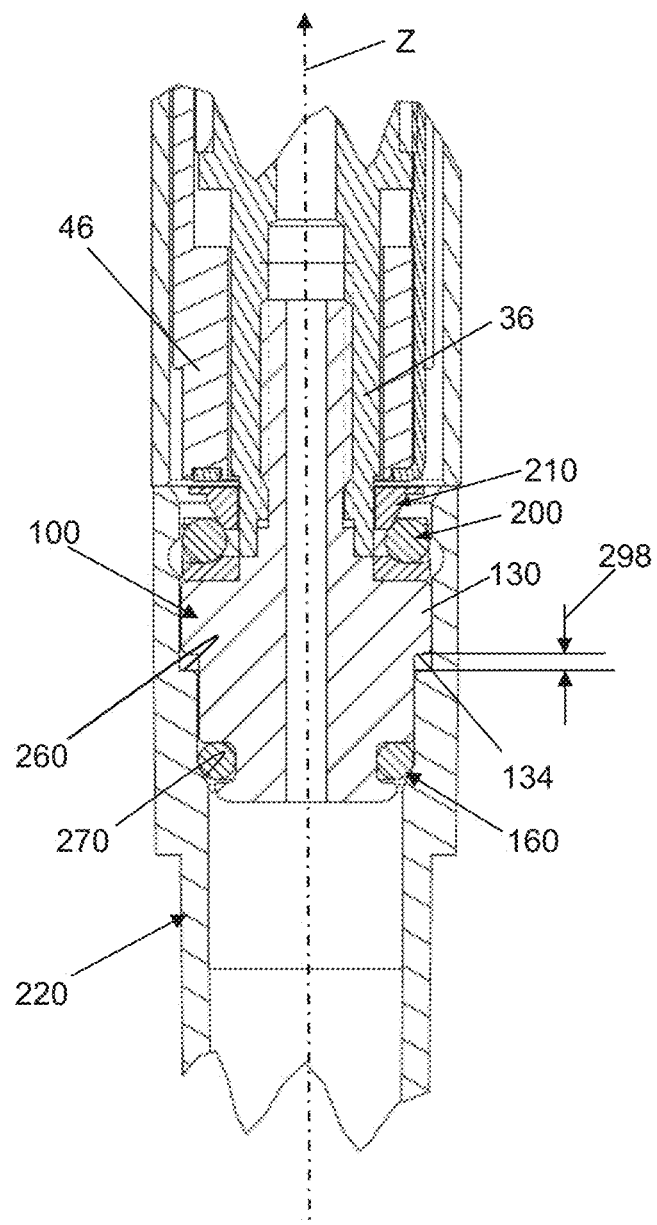
FIG. 21 is a fragmentary, longitudinal sectional, side elevational view of an example embodiment of the pipette tip coupler device moved into an example embodiment of the disposable pipette tip for contacting the distal O-ring against the tip sealing seat or surface such that a gap is maintained between the annular shoulder seat or stop surface of the pipette tip and the stop shoulder surface of the stop disk with the plurality of circumferentially spaced apart segments or balls retracting by contacting the interior surface of the pipette tip and being forced inwardly.

Next, FIG. 21 illustrates the pipette tip coupler 100 being moved down along the Z-axis and the squeeze sleeve 46 being moved down along the Z-axis into contact with the annular wedge squeeze ring 210 that surmounts the plurality of spherical balls 200 for lowering the distal elastomeric carrying portion of the pipette tip coupler 100 to pass into the interior cylindrical proximal end portions of the pipette tip 220 to bring the distal O-ring 160 into contact with the tip annular sealing seat or stop surface 270 while maintaining the plurality of spherical balls 200 in the unsqueezed state and before the annular shoulder seat or stop surface 260 of the pipette tip 220 and the axial stop shoulder surface 134 of the stop disk 130 are mated such that a gap 298 is maintained between the annular shoulder seat or stop surface 260 of the pipette tip 220 and the axial stop shoulder surface 134 of the stop disk 130.

Figure 22:
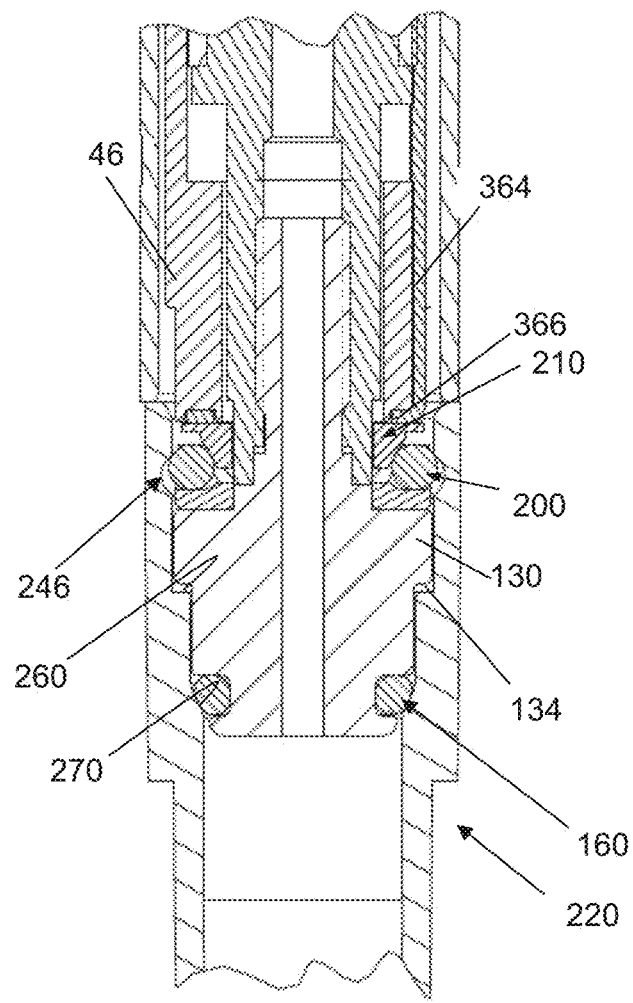
FIG. 22 is a fragmentary, longitudinal sectional, side elevational view of an example embodiment of the pipette tip coupler device moved into the tip a further amount with the annular wedge initially squeezing the elastomeric element or O-ring and the tip being lifted up for defining a first extended or lift state with the distal elastomeric element or O-ring in an initially compressed and seated state.

Next, FIG. 22 illustrates the squeeze sleeve 46 being moved further down along the Z-axis for pushing against the LLD circuit ring end 366 that makes contacts with and pushes against the annular wedge squeeze ring 210 that pushes down onto the plurality of spherical balls 200 for starting the process of squeezing or pushing the spherical balls 200 into the groove 246 and initially into abutment with the upper axially arcuate circumferential surface sector portion 250 (FIG. 17) of the axially arcuate circumferential interior surface 244 (FIG. 16) defining the groove 246 wherein the action of the plurality of spherical balls 200 extending or being projected into the groove 246 causes an axial upward force that pulls the pipette tip 220 axially up.

As a result, and referring to FIGS. 21 and 22, this starts a process of seating the proximally or upwardly facing annular shoulder seat surface 260 of the pipette tip 220 with the distally or downwardly facing axial stop shoulder surface 134 of the stop disk 130 for closing the gap 298 and concurrently compressing the distal or lower O-ring 160 with the sealing seat or stop surface 270 of the tip 220.

FIG. 23 illustrates the squeeze sleeve 46 being moved down along the Z-axis a pre-calibrated or predetermined length until it is locked in position resulting in the annular wedge or squeeze ring 210 being stopped and locked in position by the squeeze sleeve 46. As a result, the spherical balls 200 are radially extended to a desired distance or value (FIG. 24) for fully seating the axial stop shoulder surface 134 of the pipette tip coupler 100 against the annular shoulder seat surface 260 of the pipette tip 220 with the seating of the two surfaces 134, 260 along the X-axis (FIG. 19) substantially perpendicular to the Z-axis (FIG. 19) for forming a normal datum between the two axis while the distal O-ring 160 is compressed to a desired distance or value (FIG. 25) for seating the distal O-ring 160 with the annular sealing seat or stop surface 270 of the tip 220 such that its cross-section is in its final compressed non-circular form thereby completing the coupling of the pipette tip coupler 100 with the pipette tip 220.

Upon completion of the securing attachment process as illustrated in FIG. 23, the segment or ball coupling system 180 and the distal elastomeric element 160 work in combination to produce a segment and seal coupling between tip 220 and coupler 100 that provides a fluid-tight seal wherein the plurality of spherical balls 200 are at least partially received within the circumferential groove 246 and at least partially seated on the circumferential arcuate interior surface 244 defining the circumferential groove 246 and wherein the distal elastomeric element 160 seals against the radially inwardly angled and distally extending surface 270 of the pipette tip 220 in a storage state of elastic potential energy.

In one aspect, and referring to FIGS. 19 through 25, the segment or ball coupling system 180 comprises the peripheral circumferentially spaced apart guide sockets 192 (FIG. 9) configured for carrying radially advancing and retracting balls for attachment and detachment of the tip 220 wherein the balls move radially outward to engage the circumferential groove 246 of the tip 220 for coupling and wherein the balls move radially inward for releasing the tip 220 as a function of axial movement of the annular wedge or squeeze ring 210. In particular, movement of the annular wedge or squeeze ring 210 axially downwards results in the plurality of spherical balls 200 being urged to a radially outward position and release of pressure on the annular wedge or squeeze ring 210 results in a release of the plurality of spherical balls 200 from the radially outward position whereby the plurality of spherical balls 200 are free to move radially inward.

In another aspect, the rigidity of the plurality of spherical balls 200 provides a more rigid coupling for providing a stiffer joint between the pipette tip 220 and coupler 100. Furthermore, the rigidity and rotatability of the plurality of spherical balls 200 provides contacts of the balls with the interior of the disposable pipette tip 220 to be largely rolling contacts thereby precluding wear and increasing coupler life.

Disposable Pipette Tip Ejection Process

FIGS. 19 through 25 illustrate, in reverse, details of successive stages of an example method or process of ejecting the pipette tip 220 from the pipette tip coupler 100 operatively carried by the pipette device 20. This tip ejection process sequence is similar to the attachment or tip pickup securing process sequence except in reverse. Also, as described below and illustrated in FIG. 28, a distal O-ring axial force component of the compressed distal O-ring 160 provides a force to help remove the tip 220 during the ejection process.

In one example embodiment, and referring to FIGS. 19 through 25, the ejection process comprises the steps of: (1) positioning the tip where it is to be discarded, such as a waste container; (2) moving the squeeze sleeve 46 upward wherein force is released from the annular wedge or squeeze ring 210 and, as a result, this force is also released from the plurality of spherical balls 200 so as to allow retraction from the groove 246 in the tip 220 by moving on the respective plurality of circumferentially spaced apart guide sockets 192, the distal O-ring 160 starts to release stored elastic potential energy as a force against the tip 220, and wherein the spring loaded eject sleeve 62 also pushes against the tip 220 to push it off such that the tip begins to release from the plurality of spherical balls 200 and coupler body member 120; (3) continue moving the squeeze sleeve 46 upward wherein the plurality of spherical balls 200 continue to retract from the groove 246 in the tip 220 and wherein the distal O-ring 160 and the spring loaded eject sleeve 62 pushes against the tip 220 to push it off wherein the tip 220 continues to release from the plurality of spherical balls 200 and the coupler body member 120; (4) continue moving the squeeze sleeve 46 to its up most position wherein the spherical balls 200 return to their original free position and are completely free of the groove 246 in the tip 220 and wherein the distal O-ring 160 returns to its original shape and the spring loaded eject sleeve 62 pushes against the tip 220 until the tip is pushed off of the coupler body member 120 by the spring loaded eject sleeve 62 and the spring loaded eject sleeve 62 becomes fully extended.

In light of the foregoing, those skilled in the art will appreciate that the above described tip mounting and ejection processes are applicable to a wide range of mechanically and/or automatically driven pipette types and designs.

Coupling and Ejection Forces

Figure 26:
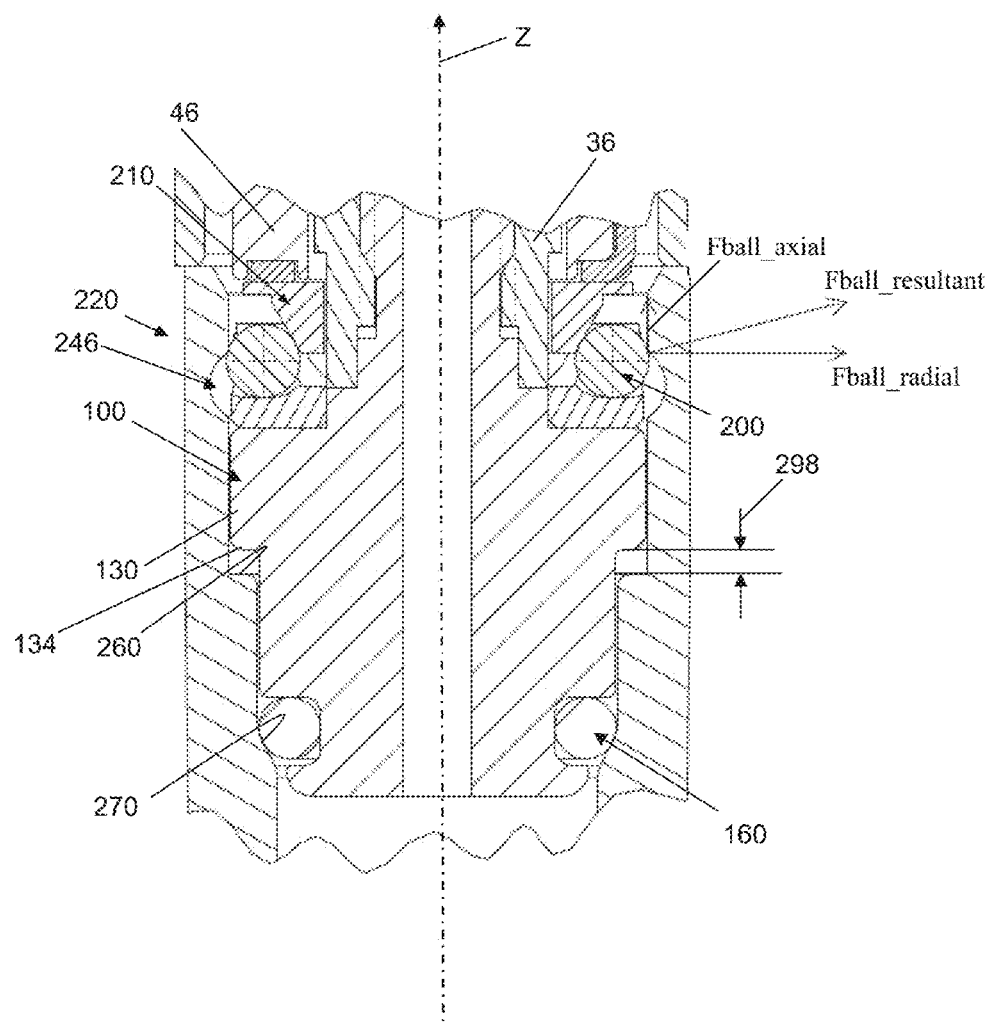
FIG. 26 is a fragmentary, longitudinal sectional, side elevational, view of an initial coupling state of an example embodiment of the pipette tip coupler device with the disposable pipette tip with an illustration of associated forces.

FIG. 26 illustrates a diagrammatical vector diagram of the plurality of spherical balls 200 of the pipette tip coupler 100 initially extending into the groove 246 with the plurality of spherical balls 200 contacting the upper corner of the tip groove above the center of the ball resulting in an axial upward force pulling the pipette tip 220 upward. As illustrated in FIG. 26, the ball force (Fball_resultant) for each ball is comprised of two components: an axial force (Fball_axial) component and a radial force (Fball_radial) component.

As long as the plurality of spherical balls 200 are contacting the upper corner of the tip groove above the center of the ball, Fball_axial increases as the distance between the ball center and corner of the groove increases. Accordingly, at the beginning of the tip pickup process, the ball axial force (Fball_axial) starts out low as illustrated in FIG. 26 and, in detail in FIG. 27, and increases to its maximum at the end of the tip pickup process as illustrated in FIG. 28.

Figure 27:
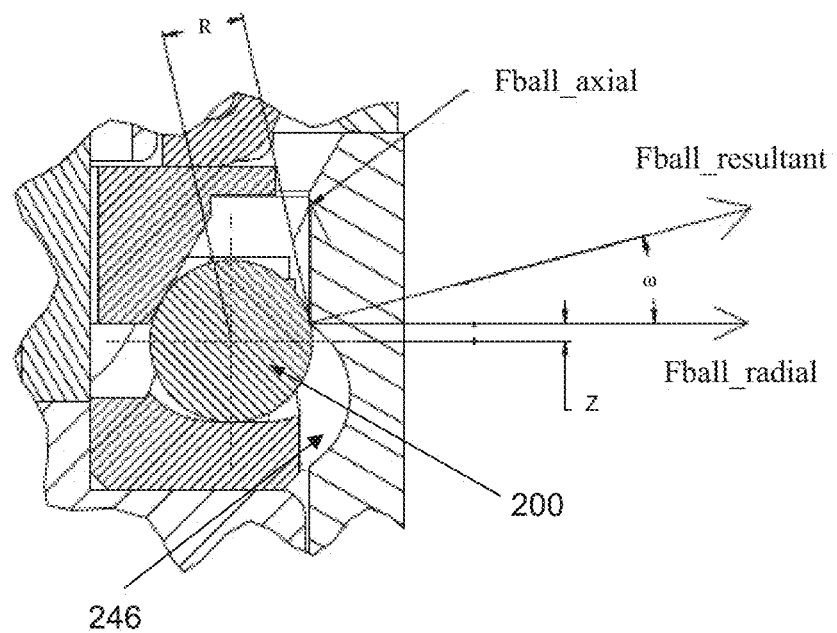
FIG. 27 is a fragmentary, longitudinal sectional, side elevational, detailed view of the initiation of coupling of one of a plurality of segments or balls of an example embodiment of the pipette tip coupler device with a groove of an example embodiment of the disposable pipette tip with an illustration of associated forces.

Referring to FIG. 27, the ratio of Z/R equals SIN (ω) and SIN (ω) is equal to (Fball_axial)/(Fball_resultant). As a result, (Fball_axial) is equal to (Fball_resultant) multiplied by the ratio of Z/R. From this, the result is that (Fball_axial) increases as Z increases.

Figure 28:
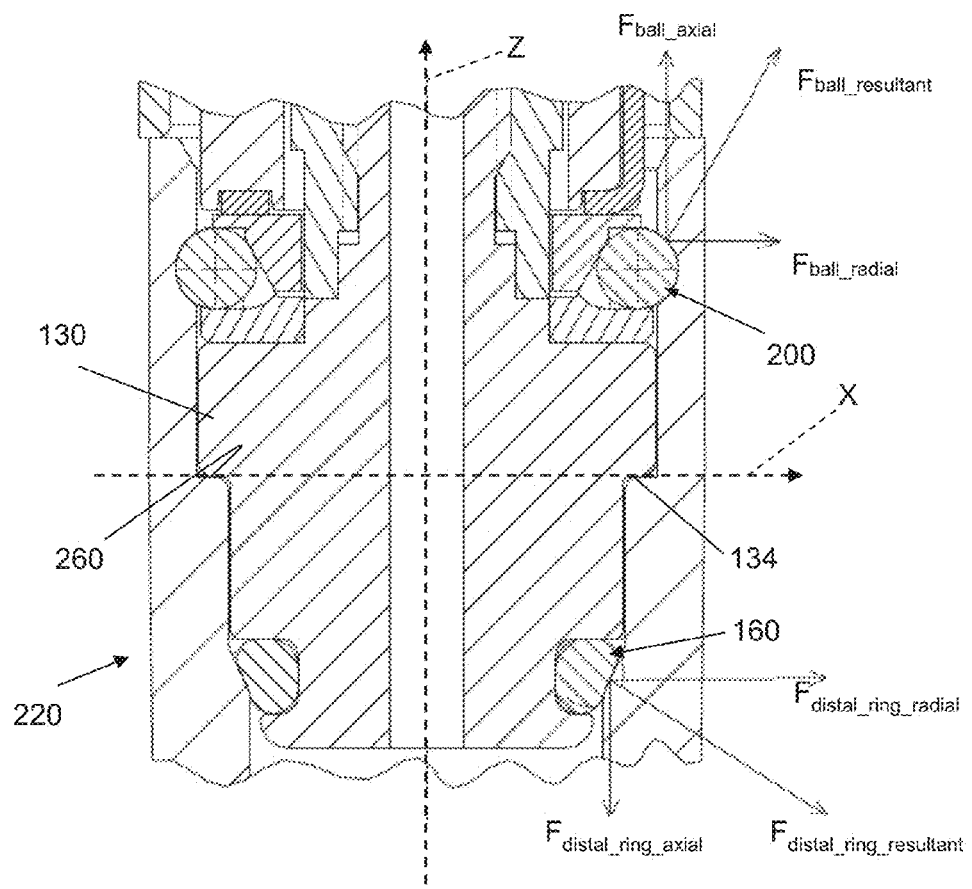
FIG. 28 is a fragmentary, longitudinal sectional, side elevational, detailed view of an example embodiment of the coupler and tip combination in the completed coupling state as illustrated in FIG. 23 and further illustrating associated forces.

Referring to FIG. 28, the ball axial force (Fball_axial) seats the stop disk 130 against the tip 220 and provides the force required to overcome an O-ring axial force (Fdistal_ring_axial) and compress the distal O-ring 160. The O-ring 160 has an O-ring force (Fdistal_ring_resultant) that results from being compressed and this O-ring force comprises two components: an axial component (Fdistal_ring_axial) and a radial component (Fdistal_ring_radial). Additionally, the ball radial force (Fball_radial) provides the radial force needed to lock the ball 200 into the tip groove 246 (FIG. 27) and the distal O-ring radial force component (Fdistal_ring_radial) provides the radial force needed to maintain the seal against the tip. Furthermore, the ball to tip groove geometry that causes Fball_axial to increase as the ball enters the groove (increasing dimension Z) helps to overcome the O-ring axial force (Fdistal_ring_axial) so that the distal O-ring 160 can be completely compressed to the desired extent. Moreover, the distal O-ring axial force component (Fdistal_ring_axial) provides force to help remove the tip 220 during the ejection process.

Alignment/Misalignment

Figure 29:
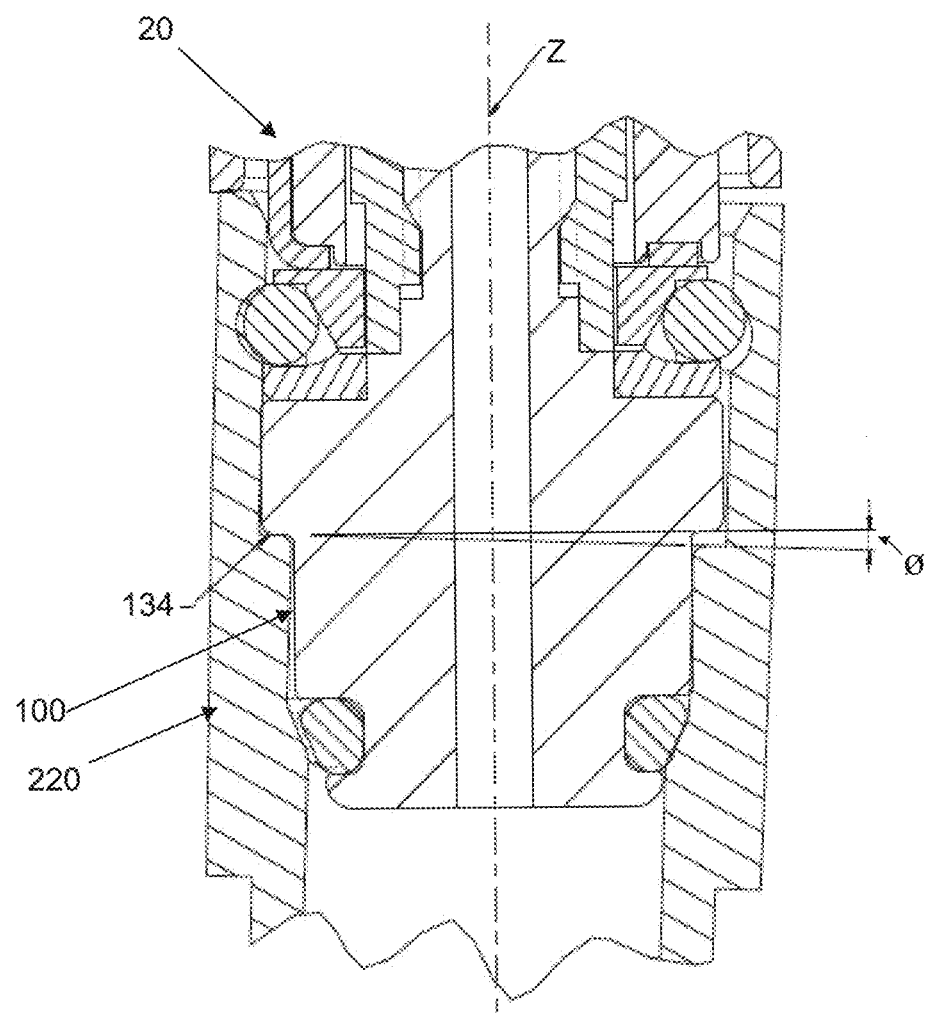
FIG. 29 is a fragmentary, longitudinal sectional, side elevational view of a misaligned coupling between an example embodiment of a pipette tip coupler device and an example embodiment of a disposable pipette tip.
Figure 30:
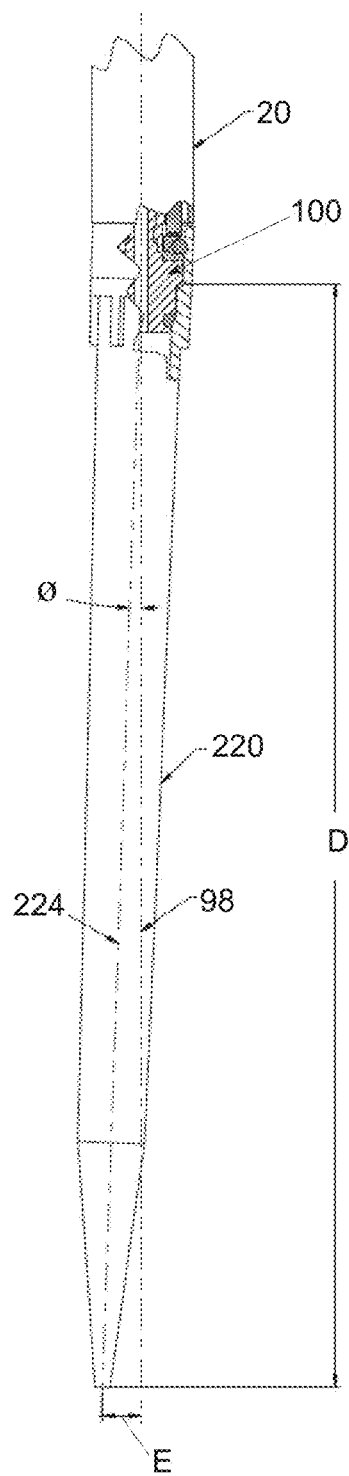
FIG. 30 is a fragmented and cutaway, longitudinal sectional, side elevational view of an example embodiment of an air displacement pipette device operatively coupled to an example embodiment of a pipette tip coupler device that is illustrated in the misaligned coupling state with an example embodiment of a disposable pipette tip.

Referring to FIGS. 26 through 30, the axial shoulder surface 134 of coupler body member 120 and the axial shoulder seat 260 of tip 220 are important for correct tip alignment. Accordingly, the coupler 100 and tip 220 are configured so that the plurality of spherical balls 200 push the axial shoulder surface 134 and the axial shoulder seat 260 together to preclude misalignment because if the shoulders are not properly mated, especially if they are tilted, the misalignment error (E) is significant as illustrated in FIGS. 29 and 30.

For example, and as illustrated in FIGS. 29 and 30, the relationship between the misalignment angle (Ø), the tip axial distance (D) and positional error (E) is: E=D*TAN(Ø). For example, with a misalignment angle (Ø) of two degrees and a tip axial distance of ninety millimeters, the positional error (E) is 3.14 millimeters. This is considered to be very high considering typical positional error tolerances are typically plus or minus 0.5 millimeters.

Figure 31:
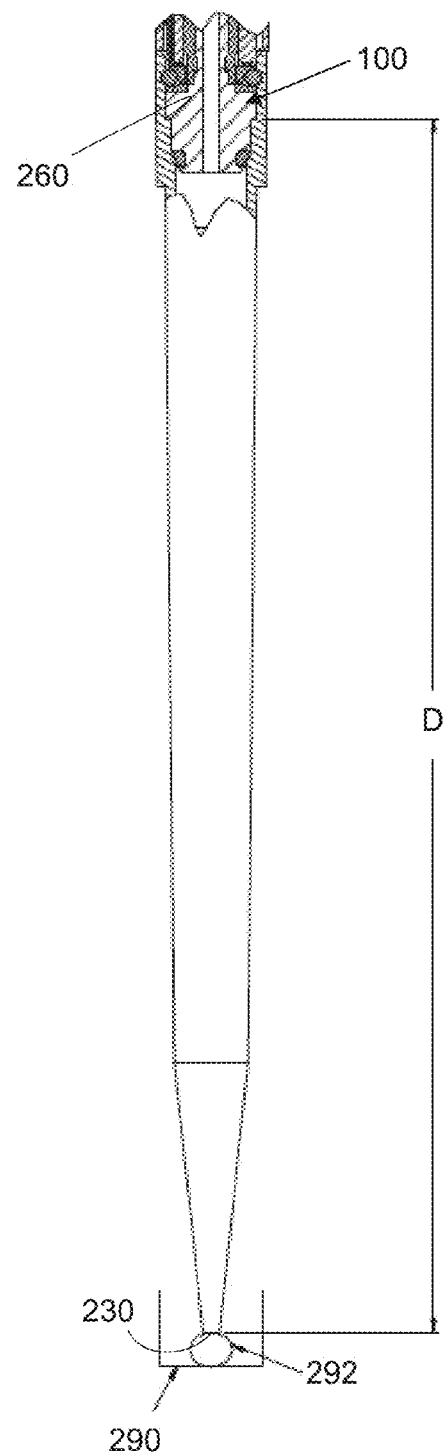
FIG. 31 is a fragmented and cutaway, longitudinal sectional, side elevational view of an example embodiment of the air displacement pipette device supporting in axial alignment an example embodiment of the pipette tip coupler device that, in turn, is coupled in axial alignment to the disposable pipette tip wherein the tip is illustrated with a small liquid volume interposed between its distal end of the tip and a working surface and with dimensioning lines illustrated and identified.

FIG. 31 illustrates correct tip alignment that maintains a tip axial distance D measured from the tip seat 260 to the distal end 230 constant to establish a known and controlled distance of the pipette tip end 230 along the vertical or axial axis Z and a perpendicular axis X illustrated in FIG. 28. This is important to allow the pipette device to target small holes and small volumes of liquid. Additionally, smaller volumes of liquid can be transferred resulting from the known fixed distance of the pipette tip allowing for a controlled touch of the pipette tip/liquid to the working surface 290 onto or from which liquid 292 is to be transferred.

Dimensions and Relationships

For proper use and operation, and referring to FIGS. 6 through 17, the dimensions between the coupler 100 and tip 220 are related accordingly. In particular, tip internal diameters of first section 242 and second section 262 must be larger than the diameter of the first cylindrical portion and the second cylindrical portion 130, 132 respectively. However, they must not be too much bigger, as this may result in a poor fit and/or misalignment.

Additionally, the diameter of tip groove 246 must be large enough to allow the plurality of spherical balls 200 to pull the tip up adequately lock the tip 220 in place. Conversely, if it is too big, the plurality of spherical balls 200 may not be able to be radially extended or projected sufficiently to get a good lock and/or seal.

The dimension between tip seat 260 and an axial center of the groove 246 is matched to the dimension between the stop disk seat 134 and the location of the center of one of the plurality of balls 200 as, for example, illustrated in FIG. 28 for providing proper coupling between the tip 220 and coupler 100.

The tip seat 260 to distal O-ring seal land 270 dimensions must match the stop disk seat 134 to distal O-ring groove 146 dimension. These dimensions control the amount that the distal O-ring 160 is compressed, and thus how well it seals.

Referring to FIGS. 28 and 31, the tip seat 260 to distal end 230 axial dimension D along with the mating of the coupling seats establish a known and controlled distance of the pipette tip end 230 along the vertical or axial axis Z and the perpendicular axis X. This is important to allow the pipette device to target small holes and small volumes of liquid. Additionally, smaller volumes of liquid can be transferred resulting from the known fixed distance of the pipette tip allowing for a controlled touch of the pipette tip/liquid to the working surface 290 onto or from which liquid 292 is to be transferred. As illustrated, in FIG. 28 the fully mated tip and stop disk seating/coupling surfaces 134, 260 provide proper alignment and maintain the tip axial distance D.

Liquid Level Detection (LLD) Circuit Contacts

Figure 32:
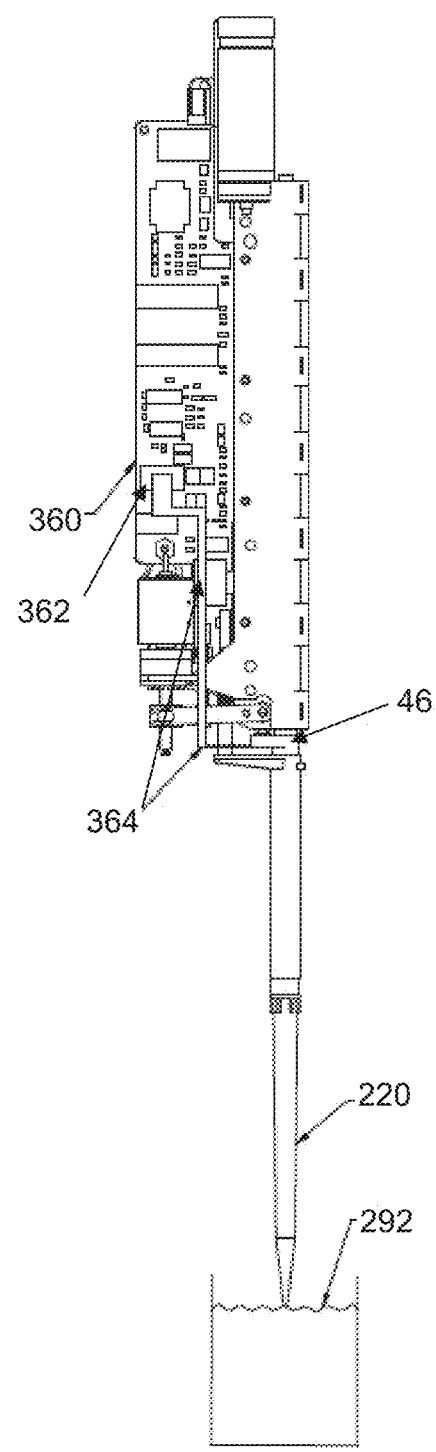
FIG. 32 is a longitudinal side elevational view of an example embodiment of the pipette device assembly illustrating a circuit board that processes a signal received from a Liquid Level Detection (LLD) circuit contact connected between the circuit board and the annular wedge or squeeze ring that selectively contacts a plurality of conductive segments or balls coupling with a conductive disposable pipette tip wherein the distal end of the tip is in contact with the liquid.
Figure 33:
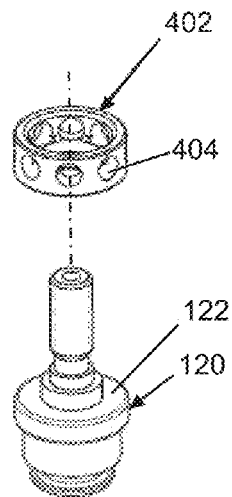
FIG. 33 is a top and side perspective view of an alternative example embodiment of a ball raceway for use with the pipette device assembly illustrated in FIG. 5.
Figure 34:
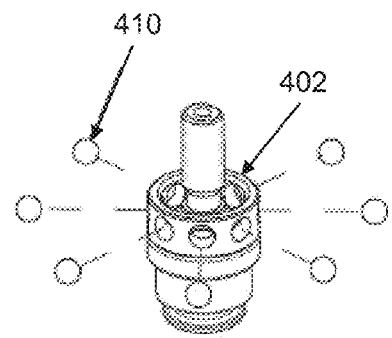
FIG. 34 is a partial exploded parts perspective view of a plurality of segments or balls and the alternative example embodiment of the ball raceway mounted on a coupler body.
Figure 35:
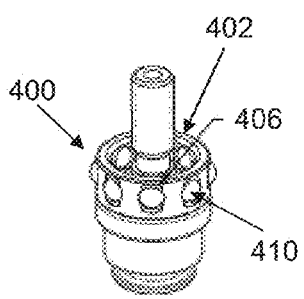
FIG. 35 is a top and side perspective view of the plurality of segments or balls captured by the alternative example embodiment of the ball raceway mounted on the coupler body.
Figure 36:
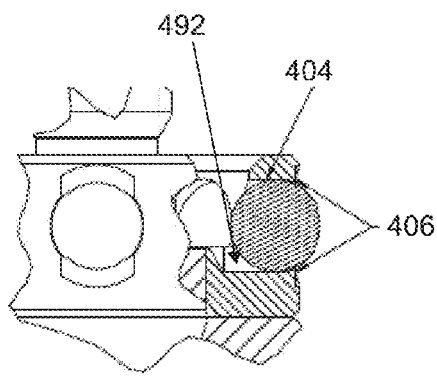
FIG. 36 is a fragmented and cutaway, longitudinal sectional, side elevational view of one of the plurality of segments or balls received and captured within the alternative example embodiment of the ball raceway.
Figure 37:
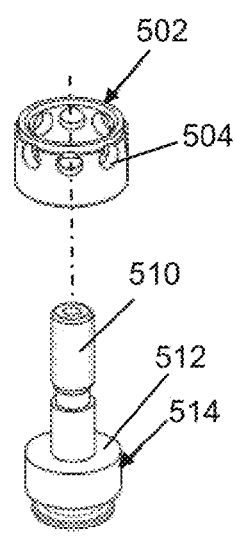
FIG. 37 is a top and side perspective view of a ball raceway and a pipette tip coupler body of a second example embodiment of a pipette tip coupler device for use with the pipette device assembly illustrated in FIG. 5.
Figure 38:
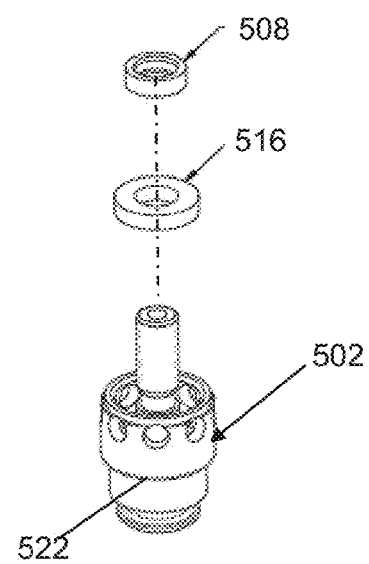
FIG. 38 is a partial exploded parts perspective view illustrating a spacer, a magnetic ring, and the ball raceway mounted on pipette tip coupler body of the second example embodiment of a pipette tip coupler device.
Figure 39:
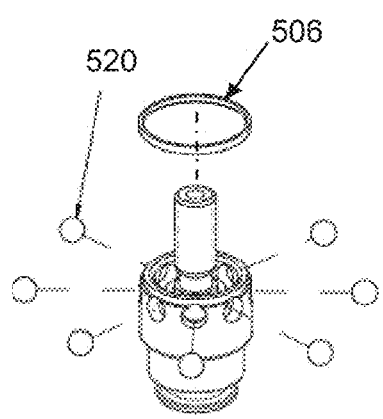
FIG. 39 is a partial exploded parts perspective view illustrating segments or balls, a top lid ring, and the ball raceway mounted on pipette tip coupler body of the second example embodiment of a pipette tip coupler device.

Referring to FIG. 32, and in one example embodiment, the pipette device assembly 10 further comprises a liquid level detection circuit assembly. The liquid level detection circuit assembly comprises a liquid level detection or LLD circuit board 360 comprising processing circuitry 362 electrically coupled to a LLD circuit contact 364 operatively coupled to the squeeze sleeve 46 that is made from an electrically non-conducting material so it is insulated from the rest of the assembly and wherein the contact 364 terminates to a circuit contact ring end 366 recessed in the bottom area of the squeeze sleeve 46 that is configured for selectively contacting the circuit contact ring end 366 with annular wedge 210 between the non-contact state illustrated in FIG. 19 and the contact state illustrated in FIG. 23 and therefore in contact with the plurality of conductive segments or spherical balls 200 coupling with the interior first working surface of tip 220 such as the tip groove 246 of the tip 220. As a result, this completes the circuit between the processing circuitry 362 of the LLD circuit board 360 and the tip 220.

Additionally, the stop disk mounting post or distal mounting flange 36 is made from a non-conducting material. Therefore, the body member 120 and the ball coupling system 180 are insulated from the rest of the assembly.

Furthermore, the processing circuitry 362 of the LLD circuit board 360 detects a signal change when the tip 220 contacts liquid thereby having an ability to detect a surface of a liquid being transferred or a surface onto or from which liquid is being transferred. Again, actuation occurs when the coupler 100 is attached to the tip 220 and the plurality of spherical balls 200 are radially pushed circumferentially and locked into the tip groove of the tip 220.

Alternate Embodiments

FIGS. 33 through 36 illustrate assembly perspective views of a ball coupling system 400 that is an alternate example embodiment of the ball coupling system 180 (FIG. 6) for substitute use. In one embodiment, the ball coupling system 400 comprises a ring-shaped raceway body 402 comprising a plurality of circumferentially spaced apart guide sockets or surfaces 492 each radially movably carrying one of a plurality of segments or spherical balls 410. The ring-shaped raceway body 402 further comprises a plurality of circumferentially spaced apart circular ball openings 404 for receiving and retaining the respective plurality of radially extended balls 410 therein wherein the balls 410 are captured by the circular ball openings 404 and retaining stakes 406 as illustrated in detail in FIG. 36.

FIGS. 37 through 40 illustrate assembly perspective views of a pipette tip coupler 500, that is an alternate example embodiment for substitute use of ball coupling system 180, shank member 102, and body 120 illustrated in FIG. 6.

Figure 40:
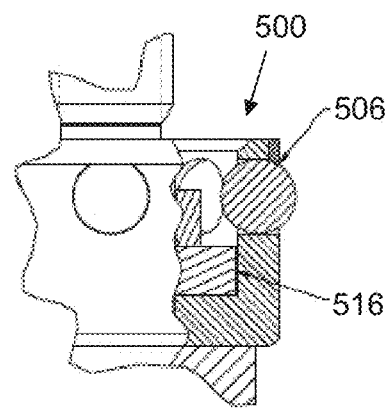
FIG. 40 is a fragmented and cutaway, longitudinal sectional, side elevational view of one of the plurality of segments or balls received and captured within the ball raceway of the second example embodiment of the pipette tip coupler device.

As illustrated in FIGS. 37 through 40, the pipette tip coupler 500 comprises a ring-shaped raceway body member 502 comprising a plurality of circumferentially spaced apart circular ball openings 504 receiving a plurality of balls 520 therein and captured by a press fitted or adhered ball keeper retaining ring 506 as illustrated in detail in FIG. 40.

The pipette tip coupler 500 further comprises an annular spacer 508 circumscribing a shank portion 510 adjacent an upper surface 512 of a disk 514 and an annular magnet 516 surmounting the annular spacer 508 for pulling the plurality of balls 520 into the raceway body member 502.

As illustrated, the body member 502 has a diameter greater than a diameter of the disk 514 such that its bottom peripheral lip defines a distally facing axial shoulder surface or stop shoulder surface 522 analogous to stop shoulder surface 134 (FIG. 6).

Pipette Tip Coupler 700

Figure 41:
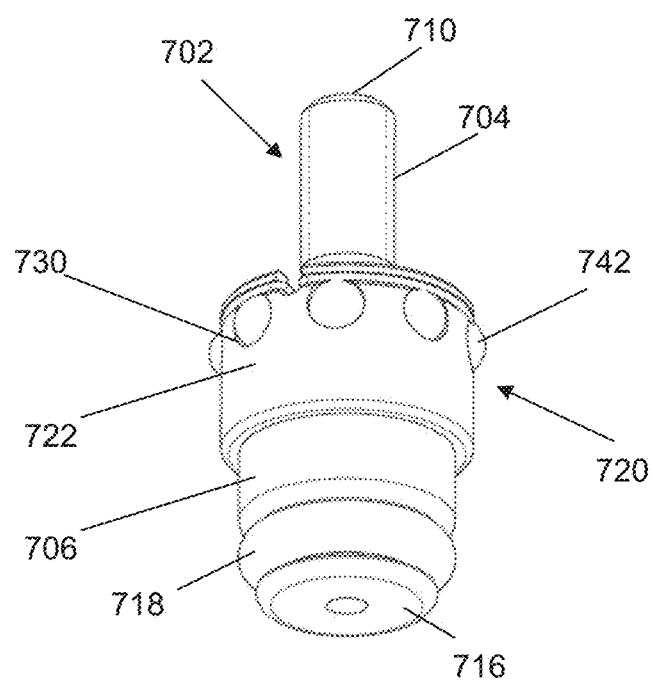
FIG. 41 is a bottom and side perspective view of a third example embodiment of a pipette tip coupler device comprising a pipette tip coupler body supporting a distal sealing element and a ball raceway with a snap ring securing a plurality of segments or balls therein.
Figure 42:
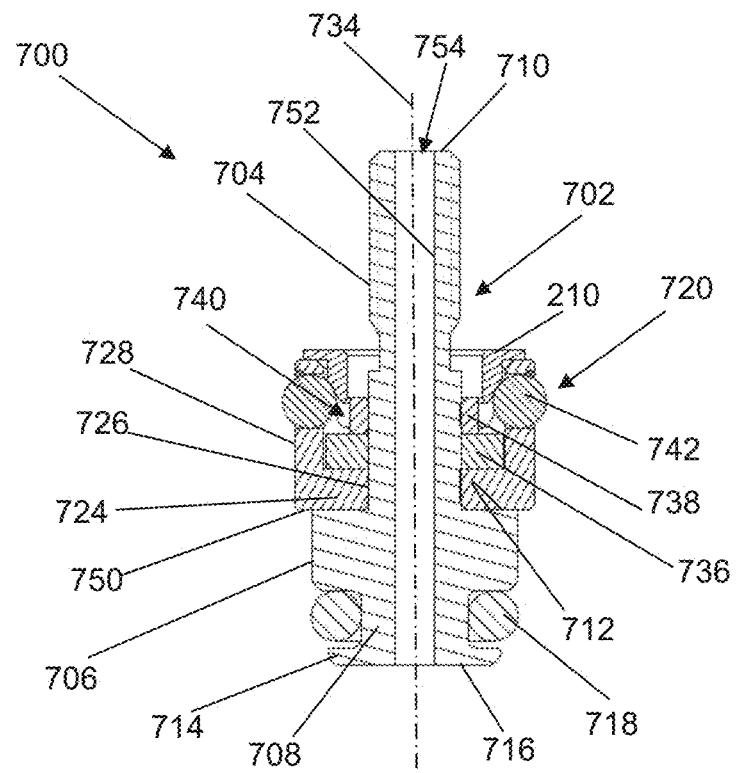
FIG. 42 is a longitudinal sectional, side elevational view of the third example embodiment of the pipette tip coupler device utilizing the annular wedge or squeeze ring that is illustrated in FIG. 12.

Referring to FIGS. 41 and 42, a pipette tip coupler device 700 is illustrated that is an alternate example embodiment of the pipette tip coupler 100 for alternative use wherein the pipette tip coupler device 700 is configured to be coupled between the disposable pipette tip 220 and the air displacement pipette device 20 of the air displacement pipette device assembly 10 (FIG. 1) utilizing the coupling process detailed above. The pipette tip coupler 700 comprises a central coupling member 702 that further comprises an elongated head or shank member 704, a body member 706, and distal stem portion 708. As illustrated, the shank member 704 includes a top end 710 and a distal end that transitions into an upper surface 712 of the body member 706. The body member 706 comprises a lower end that transitions into the distal stem portion 708. The distal stem portion 708 terminates to an end plate 714 that is generally round having a bottom end surface 716.

In one embodiment, the body member 706 has a diameter greater than a diameter of the shank member 704 and the distal stem portion 708. As illustrated, the ball segment and seal pipette tip coupler device 700 further comprises a distal elastomeric element 718 circumscribing the distal stem portion 708 wherein the distal elastomeric element 718 is configured analogous to element 160 (FIG. 6).

As illustrated in FIGS. 41 and 42, the pipette tip coupler device 700 also comprises a ball segment coupling system 720 disposed about the shank member 704 and mounted on body member 706. Additionally, the pipette tip coupler device 700 further comprises an annular wedge or squeeze ring 210 or 810 (detailed below) that is disposed about the shank member 704 and that surmounts the ball segment coupling system 720.

Figure 43:
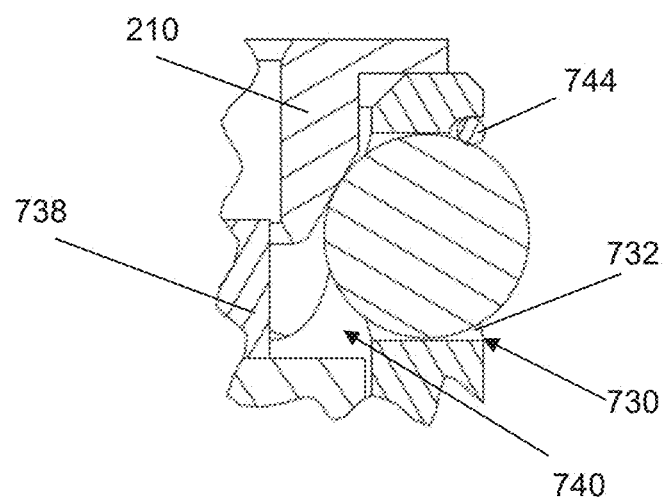
FIG. 43 is a fragmentary, longitudinal sectional, side elevational view of the third example embodiment of the pipette tip coupler device illustrating the contact between the annular wedge or squeeze ring illustrated in FIG. 12 and one of the plurality of segments or balls and further illustrating the snap ring securing one of the plurality of segments or balls.
Figure 44:
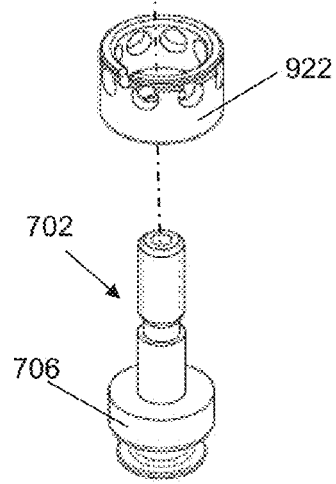
FIG. 44 is a partial exploded parts perspective view illustrating the pipette tip coupler body and the ball raceway of the third example embodiment of the pipette tip coupler device.
Figure 45:
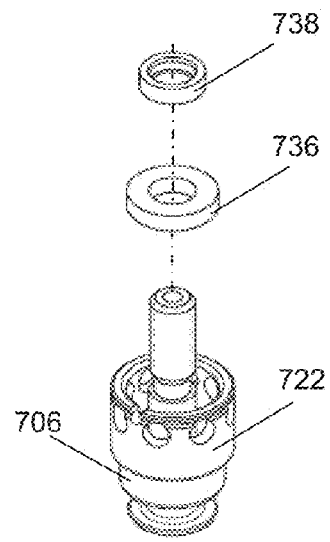
FIG. 45 is a partial exploded parts perspective view illustrating a spacer, a magnetic ring, and the ball raceway mounted the pipette tip coupler body of the third example embodiment of the pipette tip coupler device.
Figure 46:
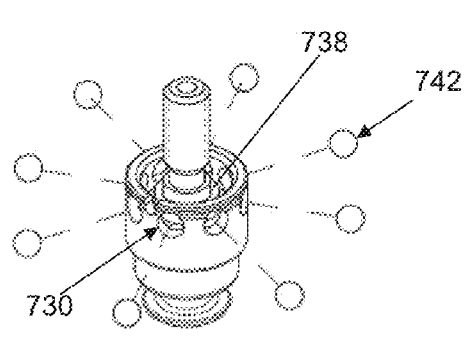
FIG. 46 is a partial exploded parts perspective view of segments or balls disposed proximate front entry openings of the ball raceway of the third example embodiment of the pipette tip coupler device.
Figure 47:
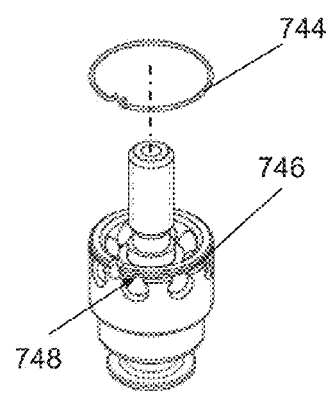
FIG. 47 is a partial exploded parts perspective view of the snap ring disposed axially above the ball raceway of the third example embodiment of the pipette tip coupler device.
Figure 48:
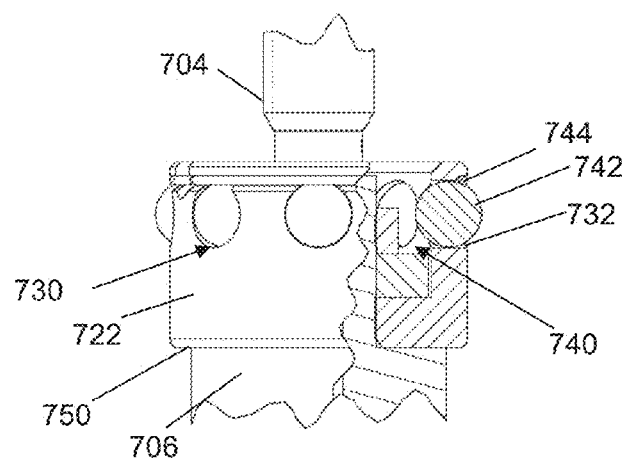
FIG. 48 is a fragmented and cutaway, longitudinal sectional, side elevational view of a portion of the ball raceway of the third example embodiment of the pipette tip coupler device with one of the plurality of segments or balls received and captured therein.

Referring to FIGS. 41 through 43, the ball segment coupling system 720 comprises a cylindrically shaped raceway body member 722 comprising an annular base 724 having a central opening 726 and an outer periphery transitioning into an upwardly extending circumscribing sidewall 728 terminating into a plurality of circumferentially spaced apart circular notched openings 730 each having a radially extending ball seating surface 732 thereby defining a raceway of ball seating surfaces 732 radially spaced from the shank member 702 such that a radially extending annular gap is formed between the openings 730 and the shank member 702.

As illustrated in FIG. 42, the pipette tip coupler device 700 further comprises an annular magnet 736 disposed about shank member 704 and mounted on the inner upper surface of the annular base 724 of the raceway body member 722 (FIG. 41). The pipette tip coupler device 700 further comprises an annular spacer 738 disposed about shank member 704 and surmounting the annular magnet 736. The annular magnet 736 is dimensioned to have a diameter greater than the annular spacer 738 for defining a radial gap 740 between the annular spacer 738 and the circular notched openings 730 of the raceway body member 722 wherein the annular magnet 736 provides a normal tendency to magnetically attract a plurality of ferrous metal balls 742 of system 720 that are disposed in the ball seating surfaces 732 of the circular notched openings 730 into the radial gap 740 toward the annular magnet 736. In one embodiment, the annular magnet 736 is a slip fit and the annular spacer 738 is a press fit, and also retains the annular magnet 736 in place.

Referring to FIGS. 44 through 48, the raceway body member 722 is aligned with and mounted on the body member 706 of the central coupling member 702 that is followed by the sequential mounting of the annular magnet 736 and the annular spacer 738 on the body member 706 of the central coupling member 702 and within the cylindrically shaped raceway body member 722. Then, the plurality of cylindrical balls 742 are respectively received through the notched openings 730 and prevented from escaping out the openings 730 by a snap ring 744 being received in a retaining groove 746 circumscribing the upper outer peripheral surface of the raceway body member 722. Snap ring 744 closes notches 748 of the circular notched openings 730 capturing the balls while allowing radial movement of the balls on the seating surfaces 732 of the raceway body member 722.

Referring to FIG. 42, the raceway body member 722 has an outer diameter greater than an outer diameter of the pipette tip coupler body member 706 of the central coupling member 702 such that a bottom peripheral lip is formed having a distally facing axial stop shoulder surface 750 that is functionally analogous to stop shoulder surface 134 (FIG. 6) of the coupler device 100.

As further illustrated in FIG. 42, the central coupling member 702 comprises an open ended, interior cylindrical channel surface 752 that defines an open ended cylindrically shaped central channel 754 that runs along the longitudinal central axis 734 of the pipette tip coupler 700 from the annular proximal or top end 710 defining the proximal end face of the pipette tip coupler 700 to the bottom end surface 716 of end plate 714 defining the distal end face of the pipette tip coupler 700. The open ended cylindrically shaped central channel 754 provides open communication between the aspirating and dispensing cylinder 34 (FIG. 3) and the pipette tip 220 wherein the aspirating and dispensing cylinder 34 is also in open communication with the aspirating and dispensing plunger 26 (FIG. 3).

Annular Wedge or Squeeze Ring 810 Comprising Ball Concavities 830

Figure 49:
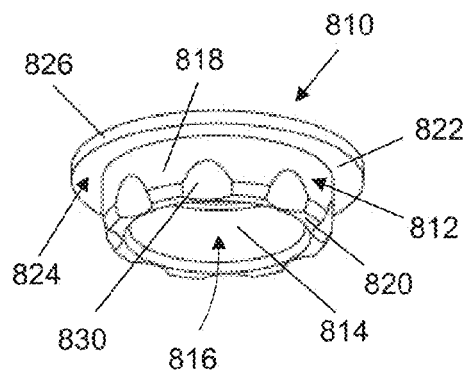
FIG. 49 is a bottom and side perspective view of another or second embodiment of an annular wedge or squeeze ring comprising circumferentially spaced apart concave faces or concavities.

FIG. 49 illustrates an annular wedge or squeeze ring 810 that comprises circumferentially spaced apart concave faces or concavities 830 and that is an alternate example embodiment of annular wedge or squeeze ring 210 for alternative use.

Figure 50:
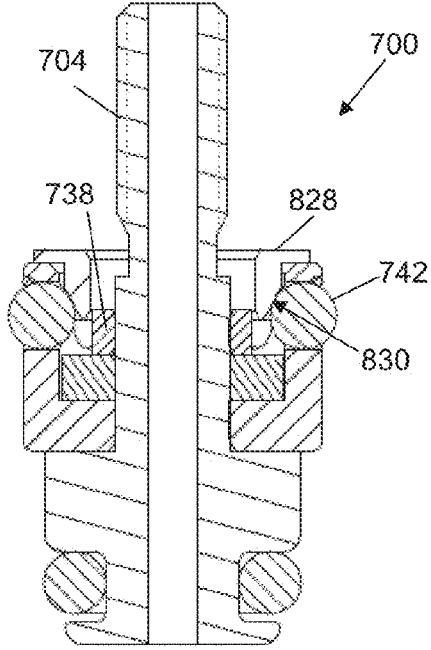
FIG. 50 is a longitudinal sectional, side elevational view of the third example embodiment of the pipette tip coupler device utilizing the second embodiment of the annular wedge or squeeze ring illustrated in FIG. 49 with the curvature of each of the circumferentially spaced apart concave faces or concavities being complemental in shape to the exterior arcuate shape of each of the plurality of segments or balls for complemental surface abutment therebetween as illustrated.

FIG. 50 illustrates the pipette tip coupler device 700 employing the squeeze ring 810 as an alternative to squeeze ring 210 (FIG. 6). As illustrated, the curvature of each of the circumferentially spaced apart concave faces or concavities 830 is complemental in shape to the arcuate shape of each of the plurality of segments or balls 742 for complemental surface abutment therebetween as illustrated wherein the plurality of segments or balls 742 are configured analogous to the plurality of segments or balls 200 (FIG. 6).

Referring to FIGS. 49 and 50, and analogous to squeeze ring 210, the squeeze ring 810 comprises a resilient annular body 812 having a central interior annular surface 814 defining a central opening 816 extending through the annular body 812. Additionally, the wedge shaped annular body 812 comprises an exterior side surface 818 upwardly extending from a bottom annular end 820 to an underside 822 of an annular peripheral lip 824 that radially extends outwardly and terminates to circumscribing outer edge surface 826 that transitions into a top planar annular surface 828 radially extending between the central interior annular surface 814 to the circumscribing outer edge surface 826. Further, the squeeze ring 810 comprises the circumferentially spaced apart concave faces or concavities 830 disposed in the exterior side surface 818 of the squeeze ring 810. As noted above, the curvature of each of the circumferentially spaced apart concave faces or concavities 830 is complemental in shape to the arcuate shape of each of the plurality of segments or balls 742 for complemental arcuate surface abutment therebetween.

Still referring to FIGS. 49 and 50, the central opening 816 of the annular wedge or squeeze ring 810 is dimensioned to allow passage of the resilient annular body 812 between the balls 742 and annular spacer 738 so as to allow a abutment and seating of the circumferentially spaced apart concave faces or concavities 830 of the annular wedge or squeeze ring 810 with the plurality of segments or spherical balls 742. In turn, and analogous to pipette tip coupler 100, the shank member 704 of the pipette tip coupler 700 is configured to operatively couple to the pipette device 20 of the pipette device assembly 10. With this coupling, the actuation of the squeeze motor 52 (FIG. 4) in the first direction results in linear axial translation of the squeeze ring 810 in a distal or vertically downward direction for applying a force axially on the top surface 828 of the squeeze ring 810 for forcing the concave faces or concavities 830 to push uniformly against the arcuate surfaces of plurality of spherical balls 742 for pushing them radially outwardly for coupling with a disposable pipette tip such as disposable pipette tip 220. Subsequent actuation of the squeeze motor 52 (FIG. 4) in a second direction, opposite the distal or vertically downward direction, releases the force on the squeeze ring 810 resulting in the plurality of segments or spherical balls 742 being urged back into the radial gap 740 toward the annular spacer 738 thereby defining the retracted or tip disengagement state of the plurality of balls 742.

Pipette Tip Coupler Device 900

Figure 51:
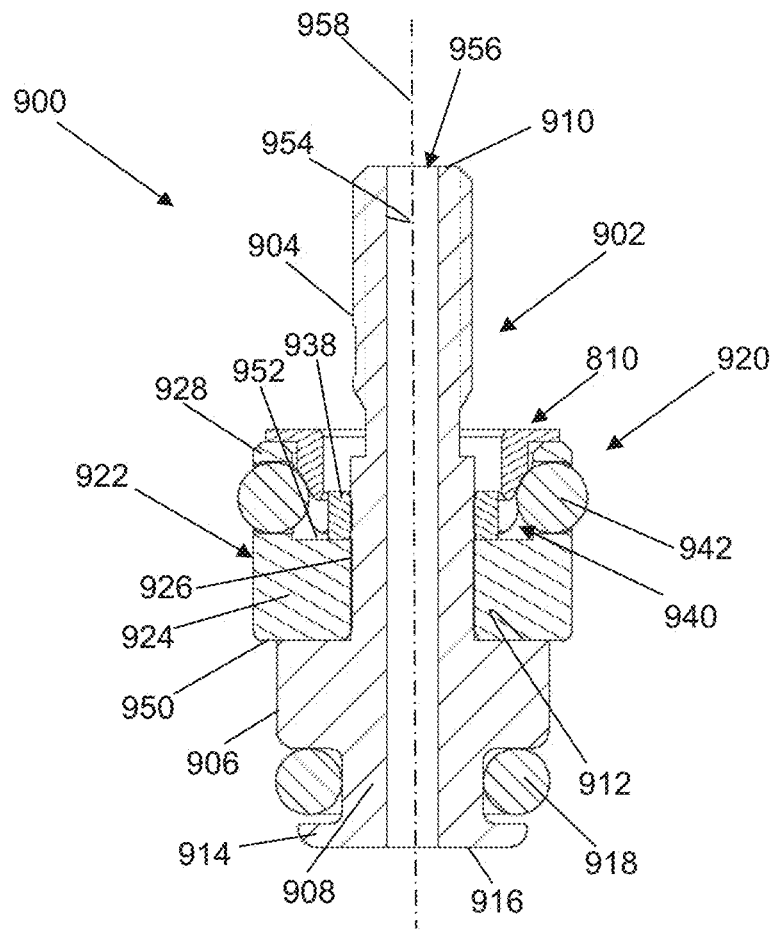
FIG. 51 is a longitudinal sectional, side elevational view of a fourth example embodiment of a pipette tip coupler device comprising an alternative ball raceway having a machined ball retention configuration securing a plurality of segments or balls therein.
Figure 52:
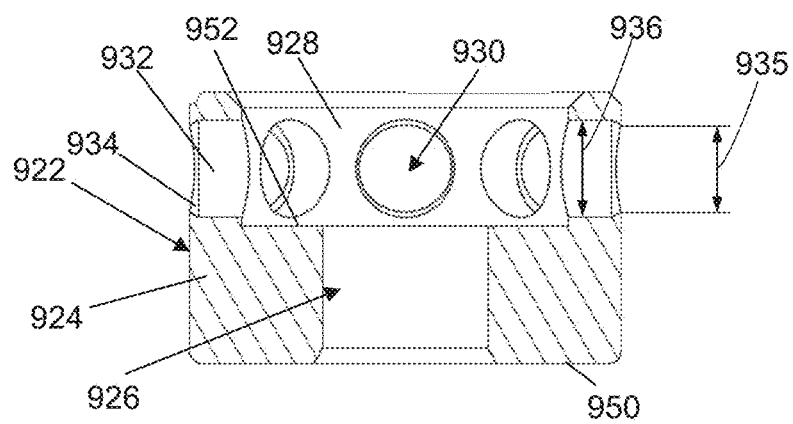
FIG. 52 is a longitudinal sectional, side elevational view detailing the machined ball retention configuration of the ball raceway of the fourth example embodiment of the pipette tip coupler device.

Referring to FIGS. 51 and 52, a ball segment and seal pipette tip coupler device 900 is illustrated that is an alternate example embodiment of the coupler device 100 for alternative use wherein the pipette tip coupler device 900 is configured to be coupled between, for example, the disposable pipette tip 220 and the air displacement pipette device 20 of the air displacement pipette device assembly 10 (FIG. 1) utilizing the coupling process detailed above.

Referring to FIG. 51, the coupler device 900 comprises a central coupling member 902 comprising an elongated head or shank member 904, a body member 906, and distal stem portion 908. As illustrated, the shank member 904 comprises a top end 910 and a lower end that transitions into an upper surface 912 of the body member 906 and the body member 906 comprises a lower end that transitions into the distal stem portion 908 that terminates to a lower end 914 having a bottom end surface 916. In one embodiment, the body member 906 has a diameter greater than a diameter of the shank member 904 and a diameter of the distal stem portion 908.

As also illustrated FIG. 51, the ball segment and seal pipette tip coupler device 900 further comprises a distal elastomeric element 918 circumscribing the distal stem portion 908 wherein the distal elastomeric element 918 is configured analogous to distal elastomeric element 160.

As further illustrated FIG. 51, the pipette tip coupler device 900 further comprises a ball segment coupling system 920 disposed about the shank member 904 and mounted on body member 906, and the squeeze ring 810 disposed about the shank member 904 and surmounting the ball segment coupling system 920.

Figure 53:
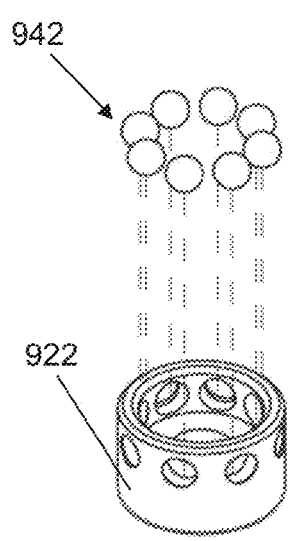
FIG. 53 is a partial exploded parts perspective view of segments or balls disposed proximate rear openings of the ball raceway of the fourth example embodiment of the pipette tip coupler device.

Referring to FIG. 52, the ball segment coupling system 920 comprises a raceway retainer body member 922, that is cylindrical in shape as illustrated in FIG. 53 and that comprises an annular base 924 having a central opening 926 and an outer periphery transitioning into an upwardly extending circumscribing sidewall 928 having a plurality of circumferentially spaced apart circular holes 930 each defined by an interior circumscribing cylindrical raceway surface 932 radially outwardly transitioning into an interior annular tapering or conic surface 934.

As illustrated in FIG. 52, the interior circumscribing cylindrical raceway surface 932 of each hole 930 has a first diameter 936 that is larger than the diameter of the ball segments 942. The interior annular tapering or conic surface 934 has a diameter that decreases from the first diameter 936 and terminates to a second diameter 935 that is smaller than the first diameter 936 and that is smaller than the diameter of each of the ball segments 942. Accordingly, the ball segments 942 are retained by the interior annular tapering or conic surfaces 934 from radially or horizontally moving out through the respective holes 930 of the raceway retainer body member 922 when in the radially translated state as illustrated in FIG. 51 thereby defining a ball segment retention configuration that is machined into the raceway retainer body member 922 and that is an alternative to the above delineated retention configurations that comprise the retaining stakes 406 illustrated in FIG. 36, the ball keeper retaining ring 506 illustrated in FIG. 40, and the snap ring 744 illustrated in FIG. 48.

As illustrated in FIG. 51, the pipette tip coupler device 900 further comprises an annular spacer 938 disposed about shank member 904 and mounted on an inner upper surface 952 of the annular base 924 of the raceway retainer body member 922. The annular spacer 938 is dimensioned to define a radial gap 940 between the annular spacer 938 and the holes 930 of the raceway retainer body member 922.

Figure 54:
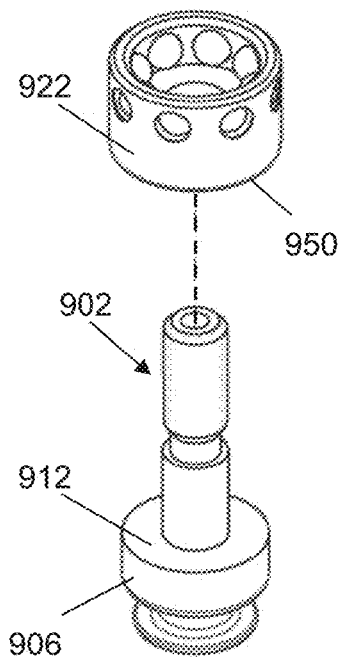
FIG. 54 is a partial exploded parts perspective view illustrating a pipette tip coupler body and the ball raceway of the fourth example embodiment of the pipette tip coupler device.
Figure 55:
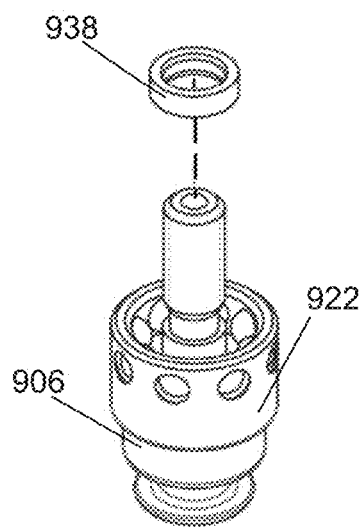
FIG. 55 is a partial exploded parts perspective view illustrating an annular spacer or ring of the fourth example embodiment of the pipette tip coupler device and the mounting of the ball raceway on the pipette tip coupler body of the fourth example embodiment of the pipette tip coupler device.

Referring to FIGS. 53 through 55, and during one example assembly process, the plurality of cylindrical ball segments 942 are respectively received through the interior ends of the holes 930 (FIG. 52) of the upwardly extending circumscribing sidewall 928 (FIG. 52) of the raceway retainer body member 922. Next, the raceway retainer body member 922 is aligned with and mounted on the upper surface 912 of the body member 906 of the central coupling member 902 wherein the raceway retainer body member 922 comprises a distally facing axial stop shoulder surface 950 having a diameter greater than the diameter of the body member 906 as illustrated in FIG. 51. The stop shoulder surface 950 is functionally analogous to stop shoulder surface 134 (FIG. 6) of the coupler device 100. The annular spacer 938 is then aligned with and mounted on the upper surface 912 of the body member 906 of the central coupling member 902 within the cylindrically shaped raceway retainer body member 922.

Figure 56:
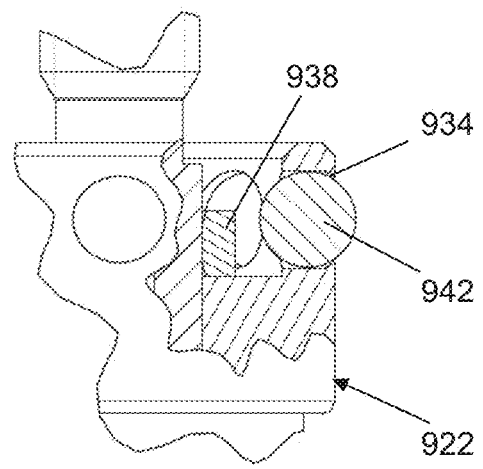
FIG. 56 is a fragmented and cutaway, longitudinal sectional, side elevational view of a portion of the ball raceway of the fourth example embodiment of the pipette tip coupler device with one of the plurality of segments or balls received and captured therein by the machined ball retention configuration.

Accordingly, and referring to FIG. 56, the plurality of cylindrical ball segments 942 are respectively received within the holes 930 (FIG. 52) and are captured for radial movement while being precluded from escaping therethrough by the interior annular tapering or conic surface 934 and back out by annular spacer 938.

As further illustrated in FIG. 51, the central coupling member 902 comprises an open ended, interior cylindrical channel surface 954 that defines an open ended cylindrically shaped central channel 956 that runs along the longitudinal central axis 958 of the pipette tip coupler device 900 from the annular proximal or top end 910 defining the proximal end face of the pipette tip coupler device 900 to the bottom end surface 916 defining the distal end face of the pipette tip coupler device 900. The open ended cylindrically shaped central channel 956 provides open communication between the aspirating and dispensing cylinder 34 (FIG. 3) and, for example, the pipette tip 220 wherein the aspirating and dispensing cylinder 34 is also in open communication with the aspirating and dispensing plunger 26 (FIG. 3).

Ball Coupling System Aspects

In one aspect, the ball coupling system comprises components that are formed from hard and durable materials such as, but not limited to, metallic or hard plastic to provide improved system life. And, because the balls are much harder than the plastic tip, they work into the tip groove more efficiently than soft elastomeric material such as an O-ring.

In another aspect, the ball coupling system provides a much stiffer joint between the tip and the stop disk and, in particular, the rigidity of the plurality of discrete balls provides a more rigid coupling for providing a stiffer joint between the pipette tip and pipette tip coupler.

In another aspect, the ball coupling system pulls the tip up and seats it more efficiently.

In another aspect, the life of the balls of the ball coupling system will not be affected by ejecting the tip in free air. In contrast, O-ring coupling life is adversely affected when the tip is ejected in free air because the O-ring is scuffed and abraded by the groove in the tip as the tip is pushed off by the spring loaded eject sleeve. The hardness of the balls resists harmful acts of the scuffing and abrasion.

In another aspect, the ball coupling materials can easily be made from conductive material in order to provide an electrical circuit to the tip for liquid level detection or other uses.

In another aspect, ball coupling system can be activated with a low squeeze/axial force because of efficient mechanical design. A lower squeeze/axial force requirement improves the life on the associated parts providing the axial force. In another aspect, ball coupling system allows the lower seal to have improved life span because of the lower squeeze/axial force requirement noted above.

In another aspect, the distal seal can be made from a greater variety of materials because it does not need to be conductive.

In another aspect, maintenance costs are lower because of the improved life and easier accessibility to the lower seal.

In another aspect, tip alignment to the pipette device is improved because of improved seating.

Pipette Tip Coupler 1100

Figure 57:
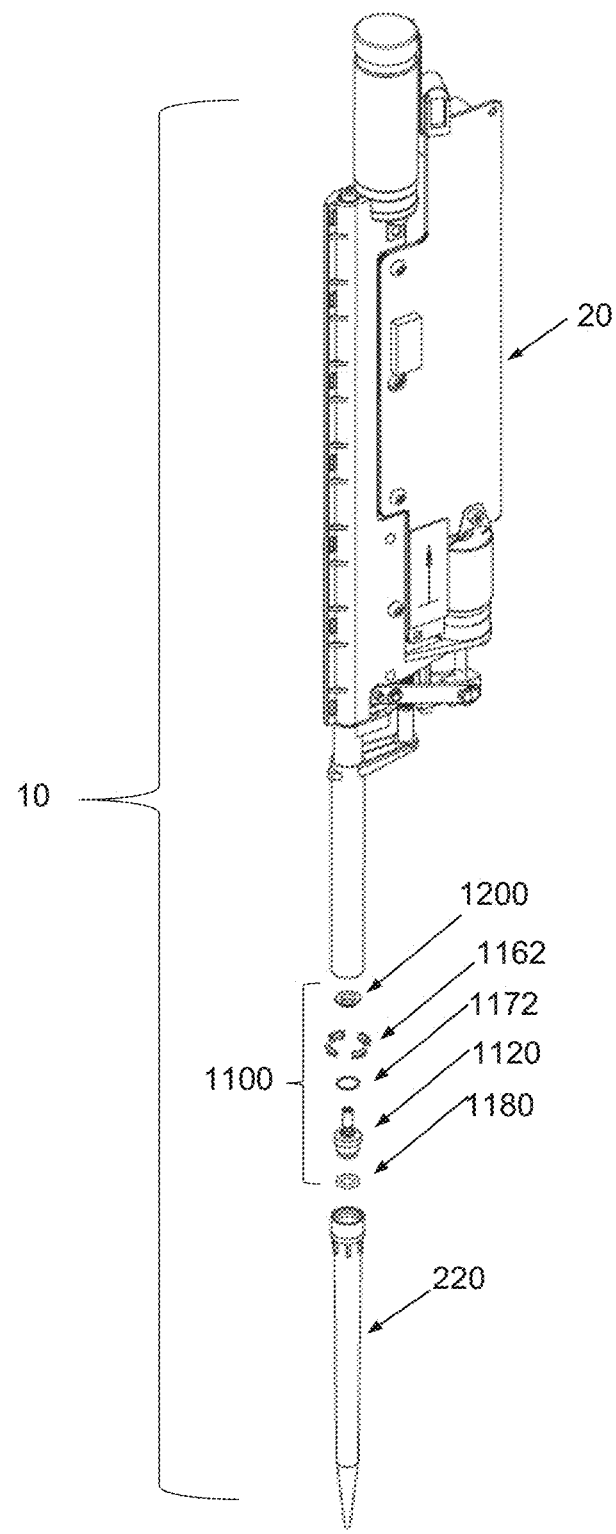
FIG. 57 is a partial exploded parts perspective view detailing parts of a fifth example embodiment of a pipette tip coupler device interposed between the disposable pipette tip and the pipette device of the air displacement pipette device assembly.

FIG. 57 illustrates a segment and seal pipette tip coupler device 1100 that is an alternate example embodiment of the coupler device 100 and that is illustrated interposed between the example embodiment of the disposable pipette tip 220 and the example embodiment air displacement pipette device 20 of the air displacement pipette device assembly 10.

Figure 58:
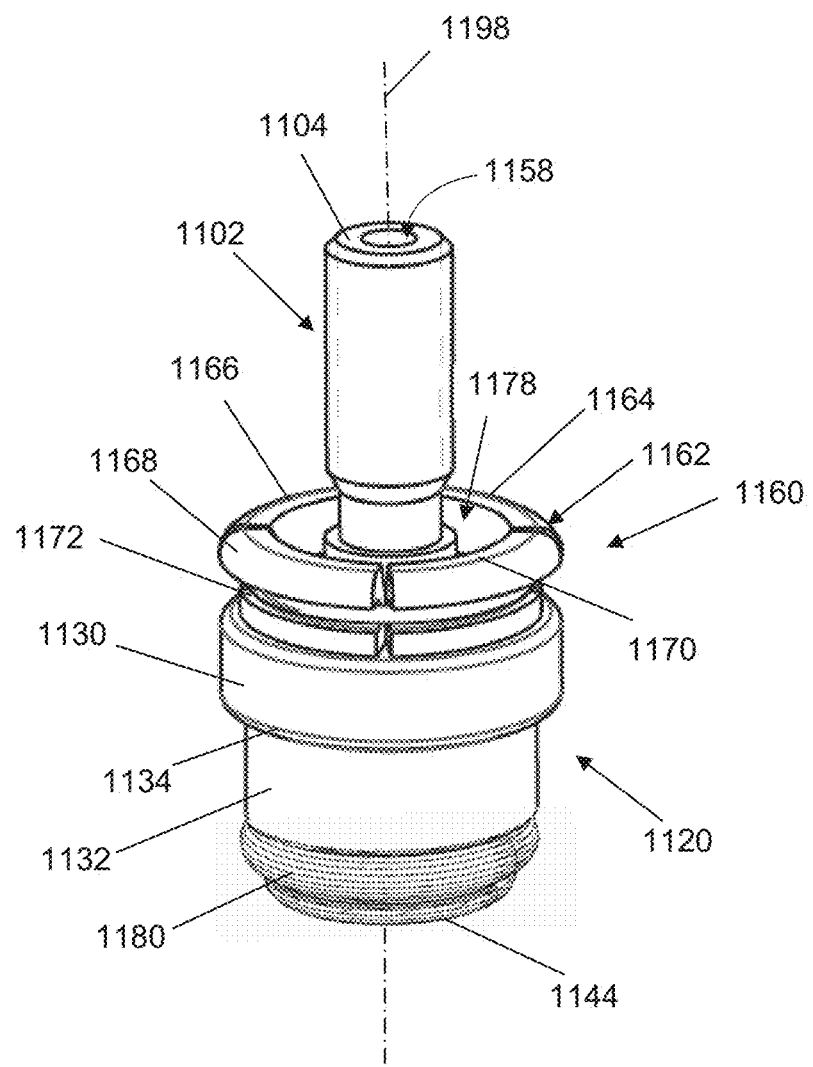
FIG. 58 is a top and side perspective view of an example embodiment of the pipette tip coupler device.

As illustrated in FIGS. 57 and 58, the pipette tip coupler 1100 comprises an elongated head or shank member 1102, a pipette tip coupler body 1120; a discrete element or segment coupling system 1160 comprising a plurality of elements or segments defining a segment ring 1162 and a spring retainer 1172; a distal elastomeric element 1180; and an annular wedge or squeeze ring 1200 surmounting the plurality of elements or segments 1162.

Figure 59:
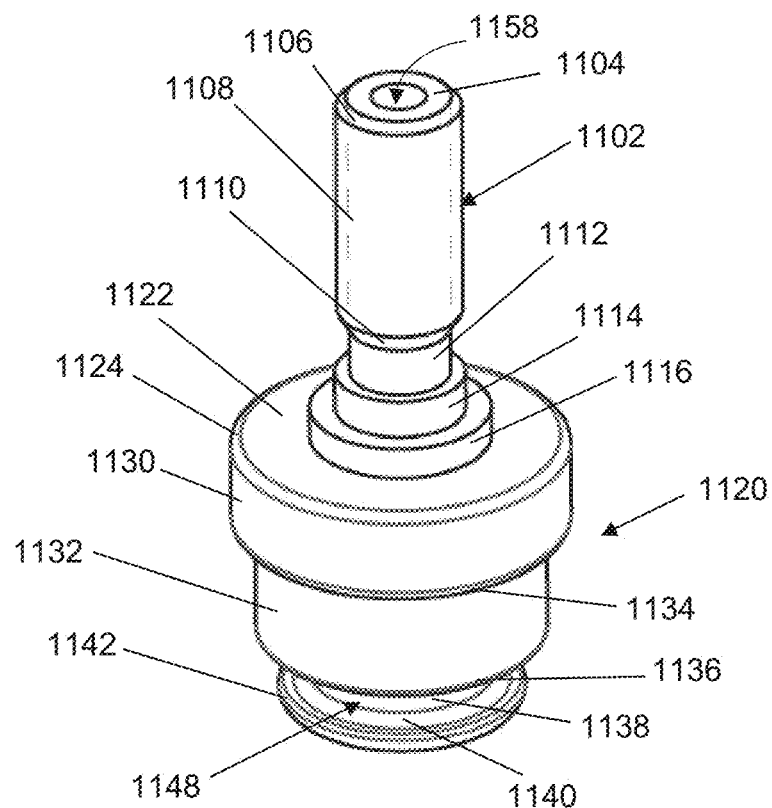
FIG. 59 is a top and side perspective view of an example embodiment of a pipette tip coupler body of the fifth example embodiment of the pipette tip coupler device.

As illustrated in FIGS. 58 and 59, the elongated head or shank member 1102 surmounts the pipette tip coupler body member 1120 and the plurality of elements or segments 1162 are circumferentially spaced apart and carried about the shank member 1102 on an upper annular surface 1122 of a first cylindrical portion 1130 of the pipette tip coupler body 1120. The spring retainer 1172 constrains the radial extension or circumferential increase of the plurality of circumferentially spaced apart elements or segments 1162.

Additionally, the pipette tip coupler 1100 comprises a lower or distal elastomeric element 1180 carried at a distal or lower end portion of the pipette tip coupler body 1120 as detailed below.

Figure 64:
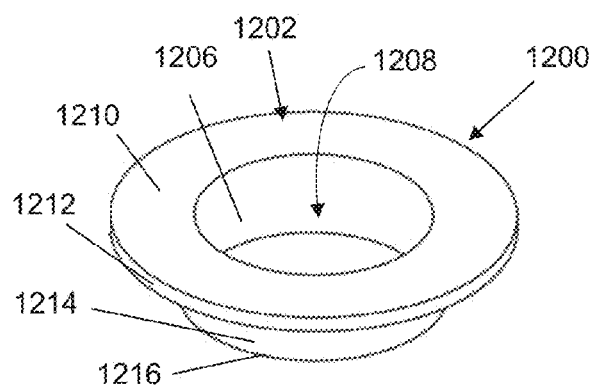
FIG. 64 is a top and side perspective view of the annular wedge of an example embodiment of the pipette tip coupler device.
Figure 65:
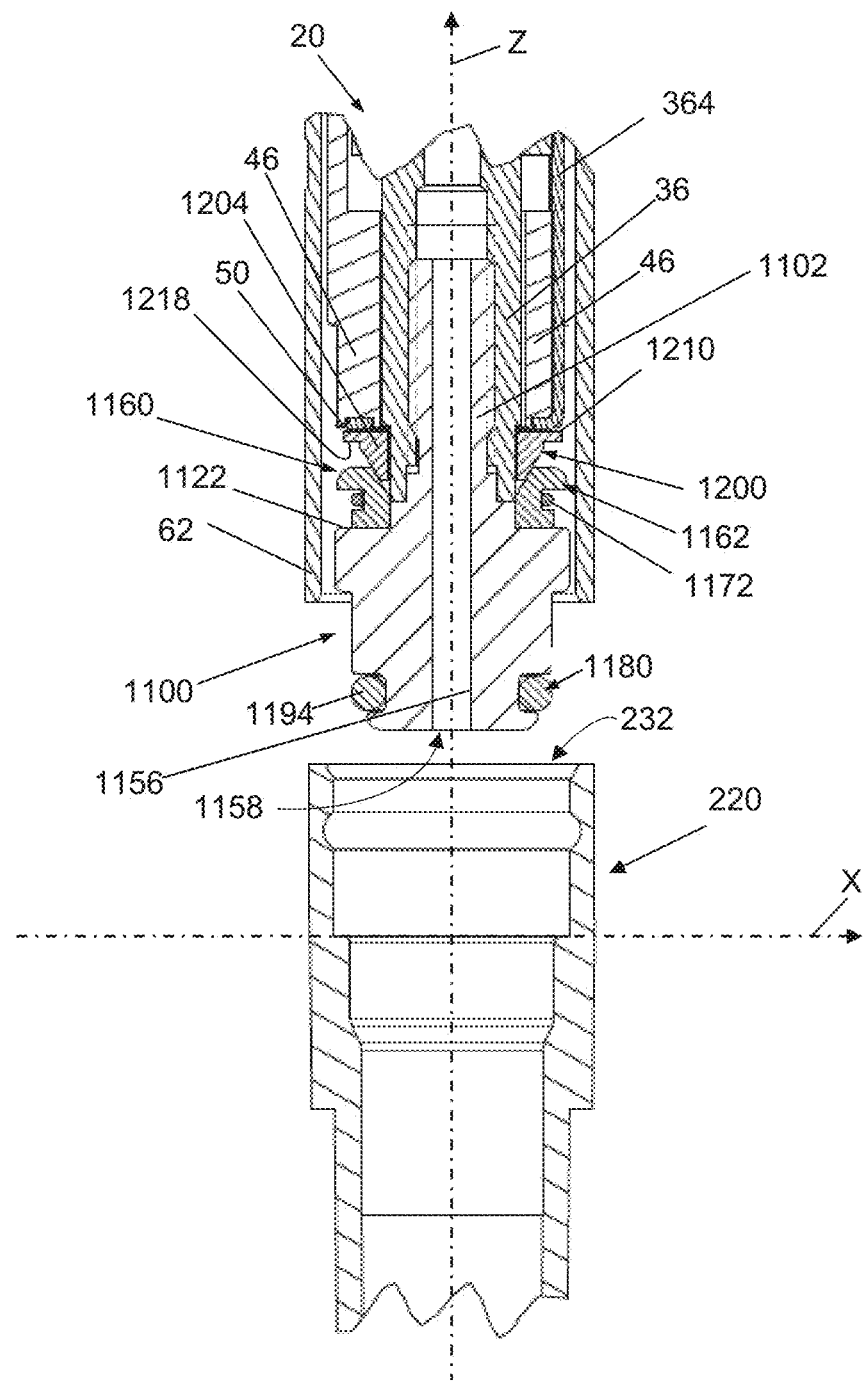
FIG. 65 is a longitudinal sectional, side elevational, fragmented view of an example embodiment of the pipette device supporting an example embodiment of the pipette tip coupler device over an example embodiment of the disposable pipette tip.

Furthermore, and as illustrated in FIGS. 64 and 65, the pipette tip coupler 1100 comprises an annular wedge or squeeze ring 1200 surmounting the plurality of elements or segments 1162 retained by spring retainer 1172 such that the plurality of elements or segments 1162 are interposed between pipette tip coupler body 1120 and annular wedge 1200 wherein the plurality of elements or segments 1162 are radially moveable against spring retainer 1172 between a radially retracted position and a radially extended position as a function of the axial location of annular wedge 1200 as illustrated in FIGS. 66 through 70 by an increasing gap 1174 (FIG. 68) between the interior annular surface 1282 of each of the plurality of elements or segments 1162 and the ring 1116 adjacently surmounting upper annular surface 1122 (FIG. 59).

Shank Member 1102

More specifically, and as illustrated in FIG. 59, the shank member 1102 comprises an annular proximal end face 1104 defining a proximal or upper end face of the pipette tip coupler 1100 and comprising an outer periphery 1106 that can be chamfered and that transitions into elongated tubular body 1108.

Distal from proximal end face 1104, the elongated tubular body 1108 transitions into an annular tapered portion 1110 that decreases in diameter and transitions into a cylindrical neck portion 1112. The cylindrical neck portion 1112 distally transitions into a cylindrical collar 1114 that has a diameter greater than a diameter of the cylindrical neck portion 1112. Next, the cylindrical collar 1114 is distally followed by a ring 1116 that has a diameter greater than a diameter of the cylindrical collar 1114 and that surmounts an inner portion of the upper circular body end surface 1122.

As illustrated in FIG. 65, the shank member 1102 of the pipette tip coupler 1100 is configured to fit within the distal mounting flange 36 of the aspirating and dispensing cylinder 34 for operatively coupling the pipette tip coupler 1100 to the pipette device 20 of the pipette device assembly 10.

Coupler Body 1120

As illustrated in FIG. 59, the superior or upper end surface 1122 of the pipette tip coupler body 1120 radially outwardly extends from the ring 1116 and transitions into an outer peripheral edge 1124 that is rounded. In one example embodiment, the upper circular body end surface 1122 is a substantially planar radially outwardly extending surface that extends from the distal end of the ring 1116 to the outer peripheral edge 1124.

Additionally, the pipette tip coupler body 1120 comprises a multi cylindrical section comprising a first cylindrical portion or stop disk portion 1130 that distally extends axially away from the upper end surface 1122 and that is distally followed by a second cylindrical portion 1132 that is reduced in diameter for forming a distally or downwardly facing axial shoulder surface or stop shoulder surface 1134 between the adjoining first and second cylindrical portions 1130, 1132.

As illustrated in FIG. 59, the second cylindrical portion 1132 distally extends from the stop shoulder surface 1134 to a distally facing lower surface 1136 that radially inwardly transitions into a reduced diameter distal cylindrical stem portion 1138 that terminates to a radially outwardly extending upper surface 1140 of a generally round end plate 1142. End plate 1142 comprises a rounded peripheral edge that provides a circumferential rounded transition between the upper surface 1140 of the end plate 1142 and a lower generally planar surface 1144 (FIG. 58) of the end plate 1142 defining the distal end face of the pipette tip coupler body 1120 of pipette tip coupler 1100.

As illustrated in FIGS. 58 and 59, the first cylindrical portion 1130 comprises a first diameter that is greater than a second diameter of the second cylindrical portion 1132 for forming the distally or downwardly facing axial shoulder surface or stop shoulder surface 1134 between the first and second cylindrical portions 1130, 1132. Additionally, the second diameter of the second cylindrical portion 1132 is greater than a diameter of the end plate 1142. Furthermore, a diameter of the distal cylindrical stem portion 1138 is less than both the second diameter of the second cylindrical portion 1132 and the diameter of the end plate 1142 for defining a lower, distal groove 1148 between the second cylindrical portion 1132 and the end plate 1142.

In one example embodiment, the first and second cylindrical head portions 1130 and 1132 respectively comprise generally smooth exterior cylindrical surfaces and the distal cylindrical stem portion 1138 comprises a generally smooth exterior cylindrical surface or groove surface.

Referring to FIGS. 58 and 65, the pipette tip coupler 1100 further comprises an open ended, interior cylindrical channel surface 1156 that defines an open ended cylindrically shaped central channel 1158 that runs along a longitudinal central axis 1198 of the pipette tip coupler 1100 from the annular proximal end face 1104 defining the proximal end face of the pipette tip coupler 1100 to the lower generally planar surface 1144 of end plate 1142 (FIG. 59) defining the distal end face of the pipette tip coupler 1100. The open ended cylindrically shaped central channel 1158 provides open communication between the aspirating and dispensing cylinder 34 (FIG. 3) and the pipette tip 220 wherein the aspirating and dispensing cylinder 34 is also in open communication with the aspirating and dispensing plunger 26 (FIG. 3).

Distal Elastomeric Element 1180

Figure 60:
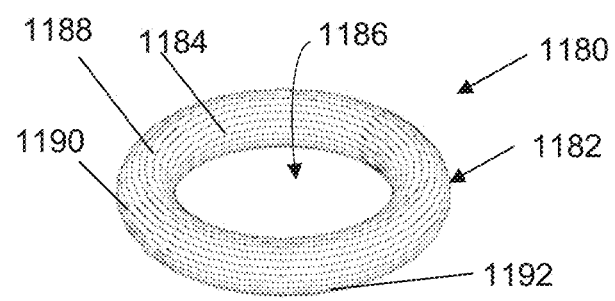
FIG. 60 is a top and side perspective view of an example embodiment of a distal elastomeric element or O-ring of the fifth example embodiment of the pipette tip coupler device.

As illustrated in FIG. 60, the elastomeric element 1180 comprises an annular body 1182 having an interior surface 1184 defining a central opening 1186, a top surface 1188, a peripheral exterior surface 1190, and a bottom surface 1192.

Referring to FIGS. 58 through 60, the central opening 1186 of the lower elastomeric element 1180 is dimensioned to tightly circumscribe the distal cylindrical stem portion 1138 of the pipette tip coupler 1100 between the distally facing lower surface 1136 of the second cylindrical portion 1132 and the upper surface 1140 of the end plate 1142 of the pipette tip coupler body member 1120 wherein the surfaces 1136,1140 are in the form of, but not limited to, a planar, conical or concaved configuration.

Accordingly, as illustrated in FIG. 58, the lower or distal elastomeric element 1180 is carried at the lower or distal end portion of coupler body 1120 by way of stem portion 1138 (FIG. 59) and is distal to the discrete element or segment coupling system 1160 that is carried at the upper or proximate end portion of coupler body 1120. In a relaxed or unsqueezed state, the lower or distal elastomeric element 1180 comprises a circumferentially continuous, generally circular cross section area 1194 as is illustrated in FIG. 65.

Discrete Element or Segment Coupling System 1160

Figure 61:
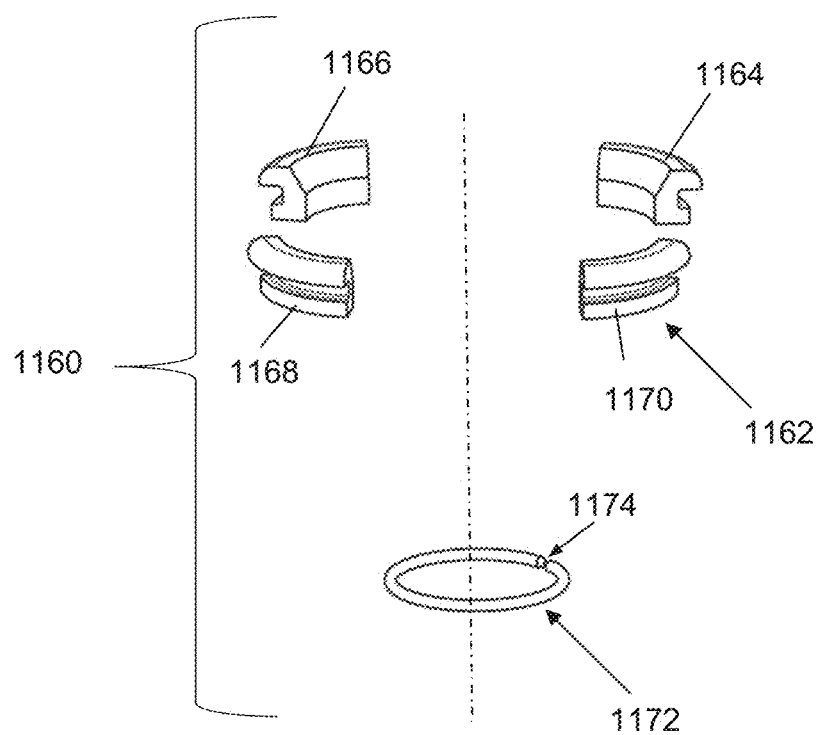
FIG. 61 is an exploded parts perspective view of a segmented coupling system of the fifth example embodiment of the pipette tip coupler device comprising a plurality of segments or individual coupling elements and a retaining ring.

FIG. 61 illustrates an exploded parts view of the discrete element or segment coupling system 1160 comprising the plurality of discrete elements or segments 1162 and the spring retainer 1172 having a gap 1174 that allows circumferential expansion of segments 1162. The plurality of discrete elements or segments 1162 define a segmented ring comprising, but not limited to, four discrete arcuate elements or segments 1164, 1166, 1168, and 1170. The gapped spring retainer 1172 circumscribes the four arcuate elements or segments 1164, 1166, 1168, and 1170 to form a radially extendable segmented ring comprising an annular base defined by the bases 1278 (FIG. 62) of the plurality of discrete elements or segments 1162 of discrete element or segment coupling system 1160.

Accordingly, and referring to FIG. 58, the discrete element or segment coupling system 1160, disposed on the upper surface 1122 of the first cylindrical portion 1130 of the pipette tip coupler body member 1120 (FIG. 59), retains the plurality of discrete elements or segments 1162 and allows movement of the discrete elements or segments 1162 between a relaxed (FIG. 66) and an extended (FIG. 70) position.

Discrete Elements or Segments 1162

Figure 62:
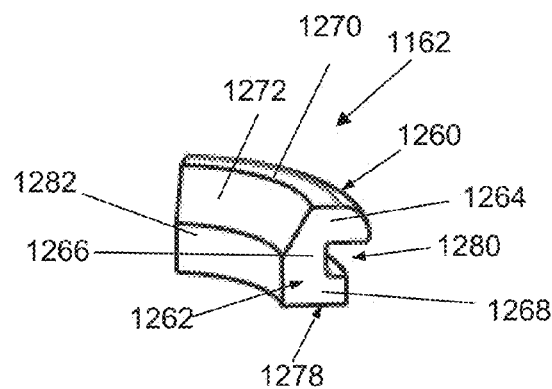
FIG. 62 is a top, back, and side perspective view of a discrete coupling element or segment of the segmented coupling system of an example embodiment of the pipette tip coupler device.
Figure 63:
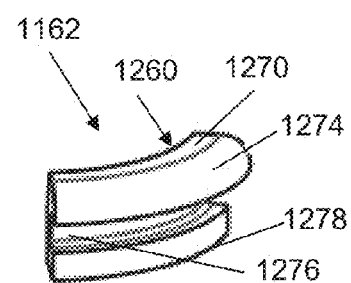
FIG. 63 is a top and front perspective view of the discrete coupling element or segment illustrated in FIG. 62.

Referring to FIGS. 62 and 63, and in one example embodiment, each of the plurality of elements or segments 1162 comprises a resilient arcuate shaped body 1260 having a generally C-shaped continuous cross sectional area 1262 along an arcuate length of the arcuate shaped body 1260.

The arcuate shaped body 1260 comprises an upper arcuate sector 1264, a medial sector 1266, and a lower base sector 1268 having an exterior base surface 1278. The upper arcuate sector 1264 comprises a top planar annular surface 1270 having an interior arcuate edge that transitions into a back side sloped surface 1272 of the body 1260 and having an outer front arcuate edge that transitions into a downwardly rounded peripheral arcuate edge sector 1274 (FIG. 63) that, in turn, transitions into a cutout surface 1276 of body 1260 forming a groove 1280. As FIG. 62 illustrates, the cutout surface 1276 (FIG. 63) of body 1260, and therefore groove 1280 (FIG. 62), has a shape, such as a generally C-shaped or a sideways U-shaped configuration, for receipt of the spring retainer 1172 (FIG. 61) that is not continuous in circumference, but includes the gap 1174 for allowing expansion.

Additionally, each of the plurality of elements or segments 1162 comprises an interior arcuate base surface 1282 extending between an inner edge of base surface 1278 and a bottom edge of the back side sloped surface 1272 of the body 1260. Thus, in the discrete element or segment coupling system 1160, the interior arcuate base surfaces 1282 of the plurality of segmented elements 1162 defines a central annular base opening extending through the segmented coupling system 1160 surmounted by a central conical opening extending through the discrete element or segment coupling system 1160 defined by the back side sloped surfaces 1272 of the plurality of elements or segments 1162 of the discrete element or segment coupling system 1160.

Annular Wedge or Squeeze Ring 1200

Referring to FIGS. 64 and 65, the annular wedge or squeeze ring 1200 comprises a resilient wedge shaped annular body 1202 having a circumferentially continuous, generally wedge shaped cross section 1204 as illustrated in FIG. 65. The resilient wedge shaped annular body 1202 comprises a central interior annular surface 1206 defining a central annular opening 1208 extending through the annular body 1202. Body 1202 further comprises a top planar circular surface 1210 radially outwardly extending from the central interior annular surface 1206 to a circumscribing outer edge surface 1212. A radially outwardly proximally inclined side surface 1214 extends from a bottom annular end 1216 to an underside of an annular peripheral lip 1218 that radially outwardly extends and terminates to the circumscribing outer edge surface 1212.

The central annular opening 1208 of the wedge shaped annular body 1202 is dimensioned to allow passage of the shank member 1102 so as to allow a seating abutment of radially outwardly proximally inclined side surface 1214 of the annular wedge squeeze ring 1200 with the plurality of discrete elements or segments 1162 of the discrete element or segment coupling system 1160 carried on the upper end surface 1122 of the pipette tip coupler body 1120 of the pipette tip coupler 1100.

With the pipette tip coupler 1100 fitted within the distal mounting flange 36, the top planar circular surface 1210 of the annular wedge or squeeze ring 1200 is adjacent the distal end 50 of the squeeze sleeve 46. Accordingly, actuation of the squeeze motor 52 (FIG. 1) in the first direction results in linear axial translation of the squeeze sleeve 46 in a distal or vertically downward direction for applying a force axially on the top surface 1210 of the annular wedge ring 1200 via the LLD circuit ring end 366 for forcing the inclined side surface 1214 to push against the plurality of discrete elements or segments 1162 for pushing them radially outward into the groove 246 of the tip 220 and into contact with surface 244 (FIG. 16) as exemplified in FIGS. 64 and 65. Subsequent actuation of the squeeze motor 52 (FIG. 1) in a second direction, opposite the distal or vertically downward direction, returns the distal end 50 of the squeeze sleeve 46 to a home position releasing the applied force on the top surface 1210 of the annular wedge ring 1200.

Discrete Element/Segment Coupling System Aspects

In one aspect, the discrete element or segment coupling system 1160 comprises components that are formed from hard and durable materials such as, but not limited to, metallic or hard plastic to provide improved system life and because the discrete elements or segments are much harder than the plastic tip, they work into the tip groove more efficiently than soft elastomeric material such as an O-ring.

In another aspect, the discrete element or segment coupling system 1160 provides a stiff joint between the tip and the stop disc.

In another aspect, the discrete element or segment coupling system 1160 pulls the tip up and seats it efficiently.

In another aspect, the discrete element or segment coupling system 1160 will not be affected by ejecting the tip in free air. The O-ring coupling life is adversely affected when the tip is ejected in free air because the O-ring is scuffed and abraded by the groove in the tip as the tip is pushed off by the spring loaded eject sleeve. The hardness of the discrete elements or segments resists the harmful acts of the scuffing and abrasion.

In another aspect, the materials of the discrete elements or segments can easily be made from conductive material in order to provide an electrical circuit to the tip for liquid level detection or other uses.

In another aspect, the discrete element or segment coupling system 1160 can be activated with a low squeeze/axial force because the mechanical design is efficient. A lower squeeze/axial force requirement improves the life on the associated parts providing the axial force. As a result of this lower squeeze/axial force requirement, the coupling system 1160 allows the lower or distal seal to have improved life span because the elastomeric material is not compressed as much.

In another aspect, the coupling system 1160 allows the lower or distal seal to be easily accessed if replacement is required. Also, the lower or distal seal can be made from a greater variety of materials because it does not need to be conductive.

In another aspect, maintenance costs are lower because of the improved life and easier accessibility to the lower or distal seal.

In another aspect, tip alignment to the pipette device 20 is improved because of improved seating.

Pipette Tip Pickup Process with Pipette Tip Coupler 1100

FIGS. 65 through 72 illustrate details of an example embodiment of successive stages of a pipette tip pickup process and, in particular, a method of securing attachment of the pipette tip 220 to the pipette tip coupler 1100 operatively carried by the pipette device 20. As noted above, and in one example embodiment, the pipette tip 220 may be supported by a support surface 282 (FIG. 15).

As illustrated in FIG. 65, the pipette tip coupler 1100 is connected to the pipette device 20, and upon command, the pipette tip coupler 1100 is positioned over the open proximal end 232 of pipette tip 220 wherein each of their respective central longitudinal axes is aligned along the Z-axis. The eject sleeve 62 is in the eject position, the squeeze sleeve 46 is in the unsqueezed position, the discrete element or segment coupling system 1160 is in the relaxed state, and the distal elastomeric element 1180 is in the unsqueezed state.

Figure 66:
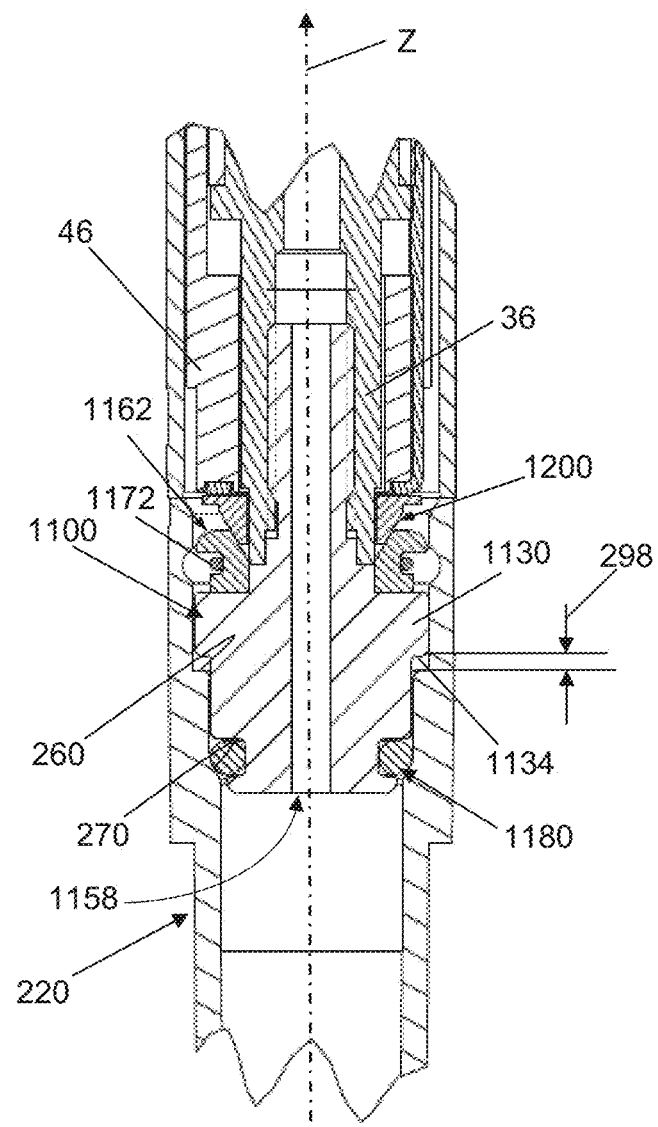
FIG. 66 is a longitudinal sectional, side elevational, fragmented view of the fifth example embodiment of the pipette tip coupler device positioned over and moved into an example embodiment of the disposable pipette tip for bringing the distal O-ring into contact with the tip sealing seat or surface while maintaining the plurality of discrete coupling elements or segments in a radially unextended state and before the shoulder seat of the pipette tip and the stop shoulder surface of the stop disk are mated such that a gap is maintained between the annular shoulder seat of the pipette tip and the stop shoulder surface of the stop disk.

Next, FIG. 66 illustrates the pipette tip coupler 1100 being moved down along the Z-axis into the pipette tip 220 for lowering the distal, elastomeric carrying portion of the pipette tip coupler 1100 into the interior cylindrical proximal or upper end portions of the pipette tip 220 to bring the distal O-ring 1180 into contact with the tip annular sealing seat or stop surface 270 while maintaining the plurality of discrete elements or segments 1162 in the unextended or unsqueezed state and before the proximally or upwardly facing annular shoulder seat or stop surface 260 of the pipette tip 220 and the distally of downwardly facing axial stop shoulder surface 1134 of the stop disk 1130 are mated such that a gap 298 is maintained between the annular shoulder seat or stop surface 260 of the pipette tip 220 and the axial stop shoulder surface 1134 of the stop disk 1130.

Figure 67:
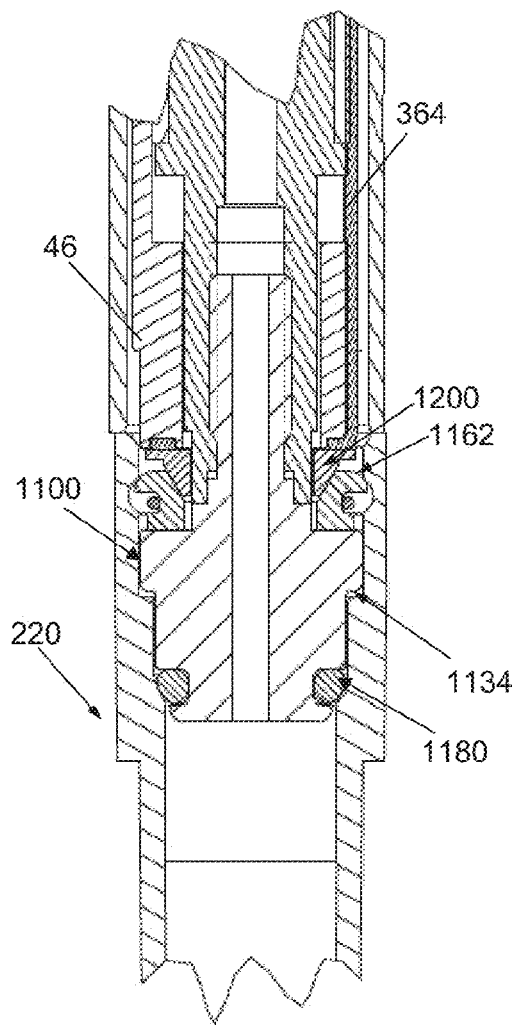
FIG. 67 is a longitudinal sectional, side elevational, fragmented view of the fifth example embodiment of the pipette tip coupler device moved into the tip a further amount with the tip being lifted while pushing down on the annular wedge squeeze ring for radially extending the segmented coupler into the groove of the tip.

Next, FIG. 67 illustrates both the pipette tip coupler 1100 and squeeze sleeve 46 being moved down along the Z-axis with the squeeze sleeve 46 squeezing the annular wedge ring 1200 against the plurality of discrete elements or segments 1162 for starting the process of pulling the tip 220 up and starting the process of pushing or squeezing the plurality of discrete elements or segments 1162 radially outward and into the groove 246. Specifically, the start of this pushing process initially places the downwardly rounded peripheral arcuate edge sector 1274 of each of the plurality of discrete elements or segments 1162 into abutment with the upper axially arcuate circumferential surface sector portion 250 of the axially arcuate circumferential interior surface 244 defining the groove 246 as illustrated in FIG. 68.

Figure 68:
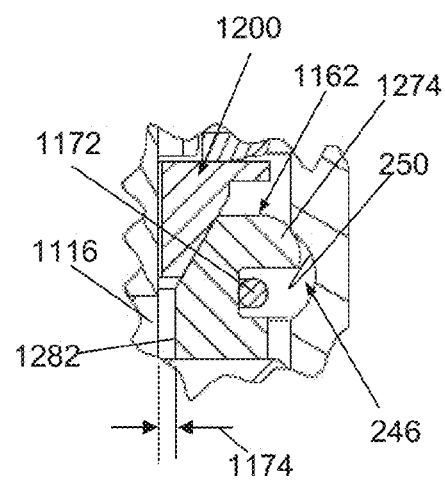
FIG. 68 is a longitudinal sectional, side elevational, fragmented detailed view of one of a plurality of segments of the segmented coupler being extended into the groove of the tip as is illustrated in FIG. 67.
Figure 69:
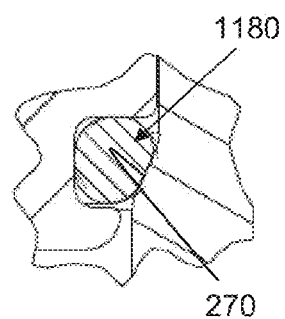
FIG. 69 is a longitudinal sectional, side elevational, fragmented detailed view of the distal O-ring in a compressed state against the tip sealing seat or surface as is illustrated in FIG. 67.

Referring to FIGS. 67 through 69, the action of the plurality of discrete elements or segments 1162 extending or being projected into the groove 246 into abutment with the upper axially arcuate circumferential surface sector portion 250 causes an axial upward force that pulls the pipette tip 220 up for starting a process of seating the annular shoulder seat surface 260 of the pipette tip 220 with the axial stop shoulder surface 1134 of the stop disk 1130 for closing the gap 298 and compressing the distal O-ring 1180 with the sealing seat or stop surface 270 of the tip 220 to start a process of energizing the distal O-ring 1180 into a storage state of elastic potential energy to be released as a force from the O-ring 1180 to the sealing seat or stop surface 270 of the tip 220 during the tip 220 ejection process.

Figure 70:
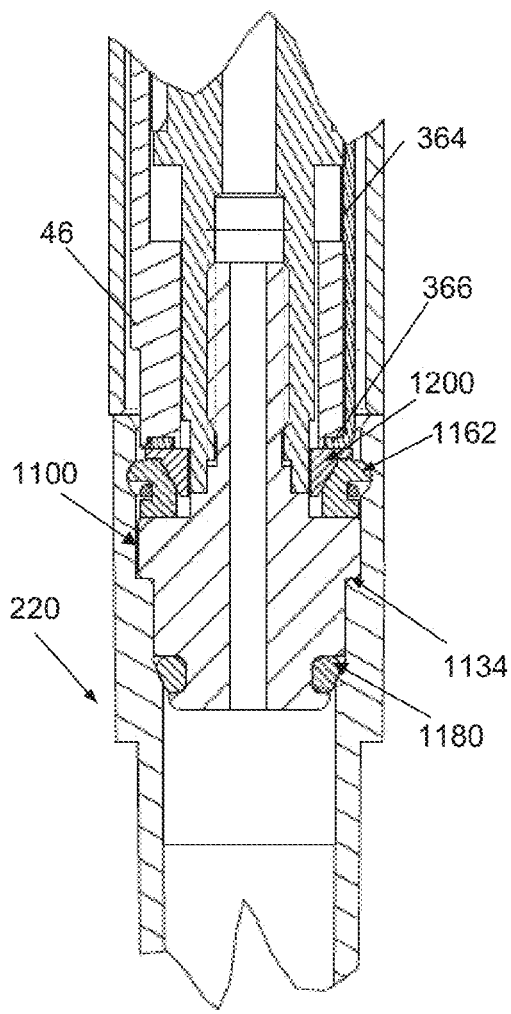
FIG. 70 is a longitudinal sectional, side elevational, fragmented view of the fifth example embodiment of the pipette tip coupler device moved into the disposable pipette tip to a final amount with the tip being lifted with a force pushing down on the annular wedge or squeeze ring for defining a final state of coupling of the fifth example embodiment of the pipette tip coupler device with the disposable pipette tip.
Figure 71:
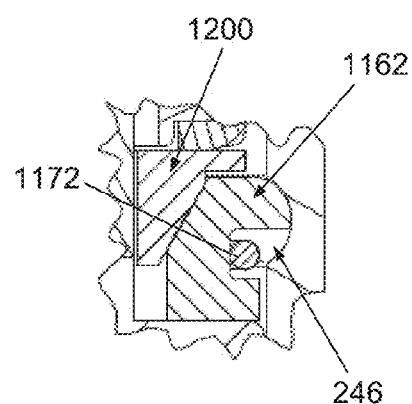
FIG. 71 is a longitudinal sectional, side elevational, fragmented detailed view of one of a plurality of segments of the segmented coupler being fully extended into the groove of the tip as is illustrated in FIG. 70.
Figure 72:
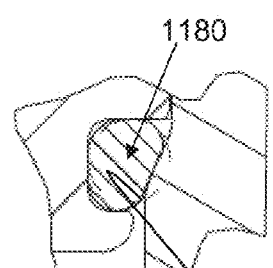
FIG. 72 is a longitudinal sectional, side elevational, fragmented detailed view of the distal O-ring in a final compressed state against the tip sealing seat or surface as is illustrated in FIG. 70.

FIG. 70 illustrates the squeeze sleeve 46 being moved down along the Z-axis a pre-calibrated or predetermined length until it is locked in position resulting in the annular wedge squeeze ring 1200 being stopped and locked in position by the squeeze sleeve 46. As a result, the plurality of discrete elements or segments 1162 are radially extended circumferentially to a desired value (FIG. 71) for fully seating the axial stop shoulder surface 1134 of the pipette tip coupler 1100 against the annular shoulder seat surface 260 (FIG. 16) of the pipette tip 220 with the seating of the two surfaces 1134, 260 along an X-axis substantially perpendicular to the Z-axis for forming a normal datum between the two axis while the distal O-ring 1180 is compressed to a desired value for seating the distal O-ring 1180 with the annular sealing seat or stop surface 270 of the tip 220 (FIG. 72) to finish the process of energizing the distal O-ring 1180 into the storage state of elastic potential energy to be released as a force from the O-ring 1180 to the sealing seat or stop surface 270 of the tip 220 during the tip 220 ejection process.

Upon completion of the securing attachment process, the discrete element or segment coupling system 1160 and the distal elastomeric element 1180 work in combination to produce a segment and seal coupling that provides a fluid-tight seal wherein the plurality of discrete elements or segments 1162 are at least partially received within the circumferential groove 246 and at least partially seated on the circumferential arcuate interior surface 244 defining the circumferential groove 246 and wherein the distal elastomeric element 1180 seals against the radially inwardly angled and distally extending surface 270 of the pipette tip 220 in a storage state of elastic potential energy.

Ejection Process

Ejecting the pipette tip 220 from the pipette tip coupler 1100 operatively carried by the pipette device 20 is similar to the attachment or tip pickup securing process sequence except in reverse and follows the process as detailed above for ejecting the pipette tip 220 from the pipette tip coupler 100. As also described above, the act of uncompressing the distal elastomeric element 1180 provides a force from the released elastic potential energy of the compressed distal elastomeric element 1180 to provide a force to help remove the tip 220 during the ejection process.

Coupling and Ejection Forces

Figure 73:
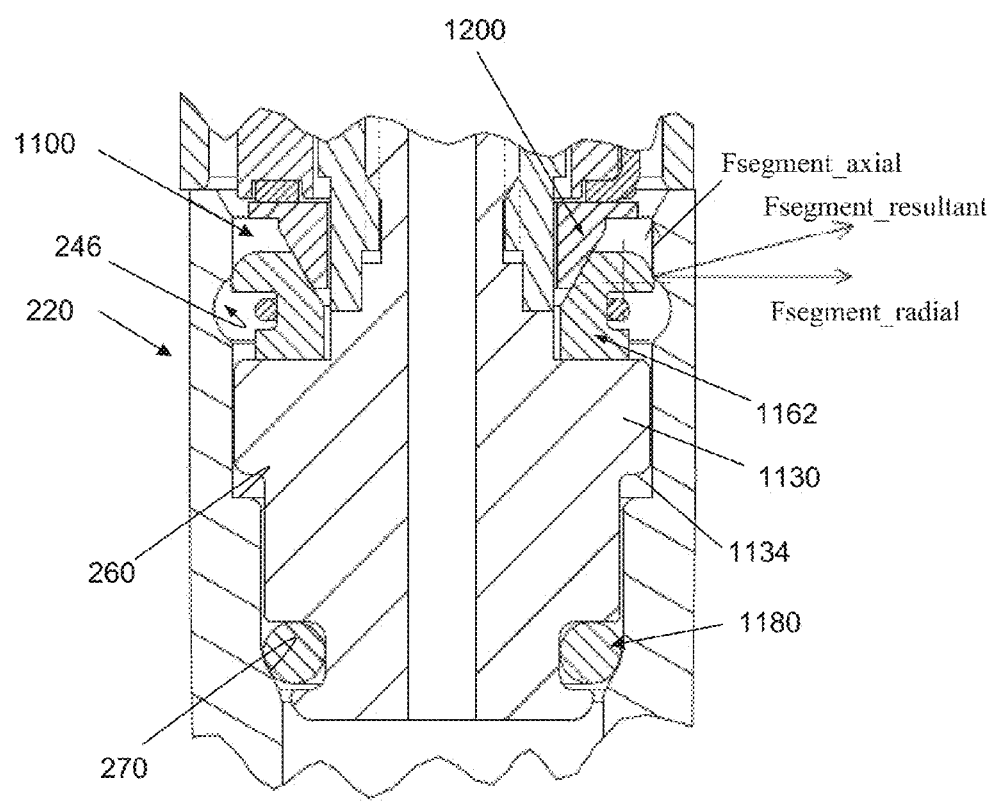
FIG. 73 is a fragmentary, longitudinal sectional, side elevational, view of an initial coupling state of the fifth example embodiment of the pipette tip coupler device with the disposable pipette tip with an illustration of associated forces.

FIG. 73 illustrates a vector diagram associated with the plurality of discrete elements or segments 1162 of the pipette tip coupler 1100 initially extending into the groove 246 with the plurality of discrete elements or segments 1162 contacting the upper corner of the tip groove resulting in an axial upward force pulling the pipette tip 220 upward. As illustrated in FIG. 73, each segmented element force (Fsegment_resultant) is comprised of two components: an axial force (Fsegment_axial) component and a radial force (Fsegment_radial) component.

Figure 74:
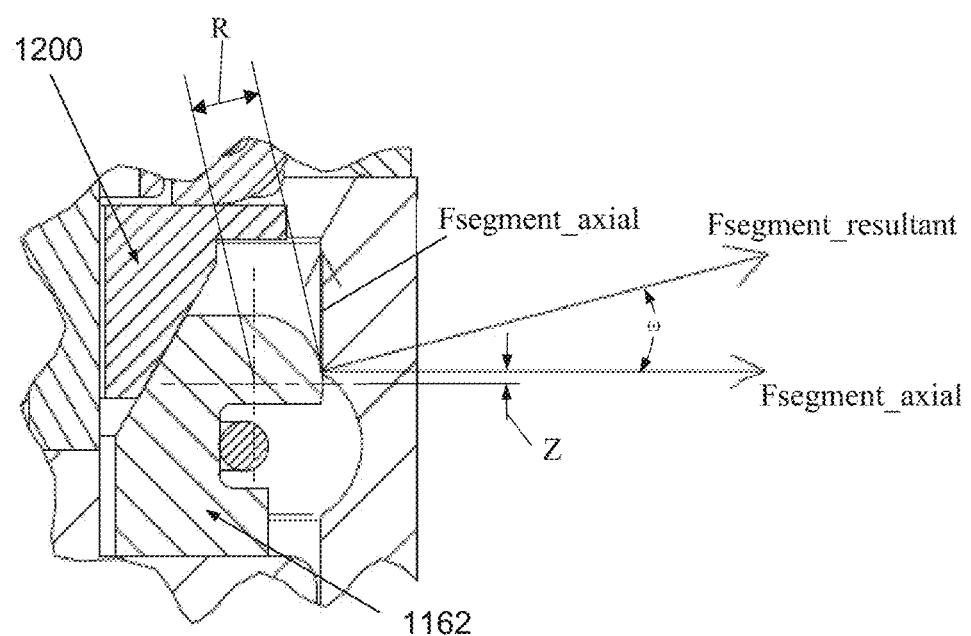
FIG. 74 is a fragmentary, longitudinal sectional, side elevational, detailed view of the initiation of coupling of one of a plurality of arcuate segments of the fifth example embodiment of the pipette tip coupler device with the groove of an example embodiment of the disposable pipette tip with an illustration of associated forces.

As long as the plurality of discrete elements or segments 1162 are contacting the upper corner of the tip groove above the center of the segment radius, dimension Z on FIG. 74, Fsegment_axial acts to pull the tip up toward the stop disk and increases as the distance between the center of the segment radius and the corner of the groove increases. Accordingly, at the beginning of the tip pickup process, the segment axial force (Fsegment_axial) starts out low as illustrated in detail in FIG. 74 and increases to its maximum at the end of the tip pickup process as illustrated in FIG. 75.

Referring to FIG. 74, the ratio of Z/R equals SIN (ω) and SIN (ω) is equal to (Fsegment_axial)/(Fsegment_resultant). As a result, (Fsegment_axial) is equal to (Fsegment_resultant) multiplied by the ratio of Z/R. From this, the result is that (Fsegment_axial) increases as Z increases.

Figure 75:
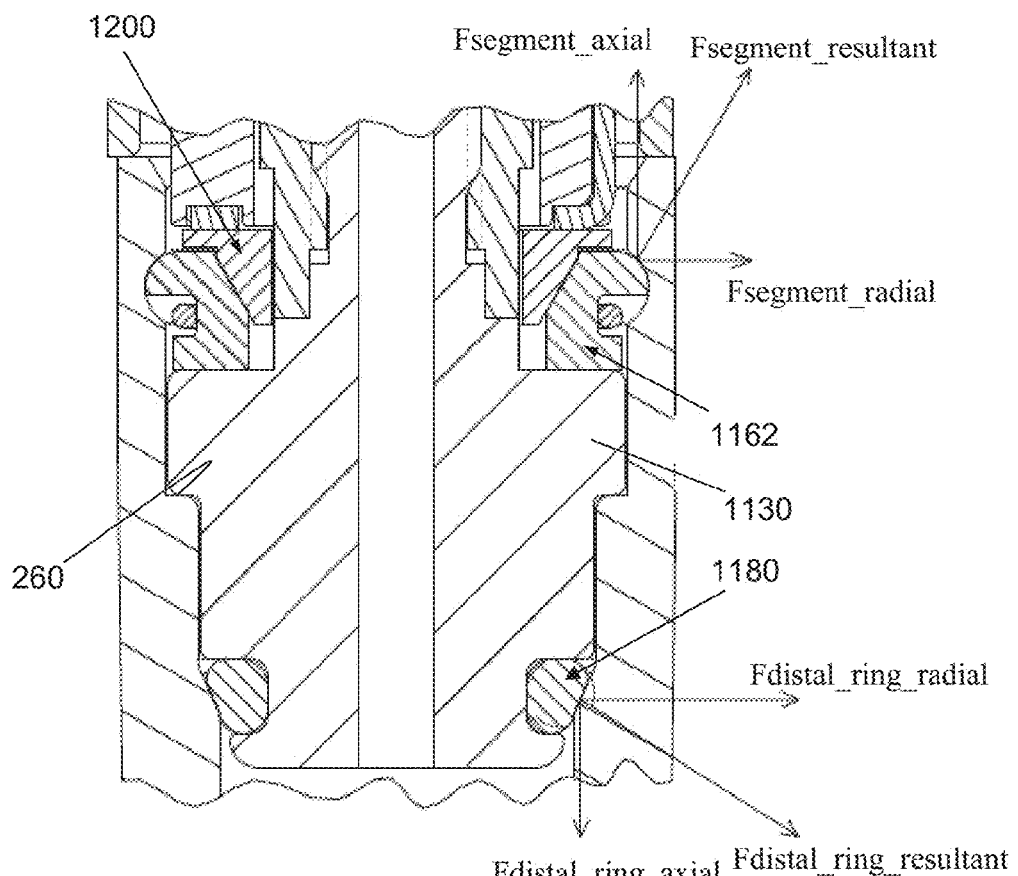
FIG. 75 is a fragmentary, longitudinal sectional, side elevational, detailed view of the completed combination coupling state of the fifth example embodiment of the pipette tip coupler device and disposable pipette tip with an illustration of associated forces.

Referring to FIG. 75, the segment axial force (Fsegment_axial) seats the stop disk 1130 against seat 260 of the tip 220 and provides the force required to overcome an O-ring axial force and compress the O-ring 1180. The segment radial force (Fsegment_radial) provides the radial force needed to lock the segment into the tip groove.

The O-ring 1180 has an O-ring force (Fdistal_ring_resultant) that results from being compressed and this force comprises two components: an axial component (Fdistal_ring_axial) and a radial component (Fdistal_ring_radial).

The segment axial force (Fsegment_axial) provides the force to overcome the O-ring axial force (Fdistal_ring_axial) and compress the O-ring 1180. The segment to tip groove geometry that causes Fsegment_axial to increase as the segment enters the groove (increasing dimension Z) helps to overcome the O-ring axial force so that the O-ring can be completely compressed to the desired extent.

Again, the segment radial force (Fsegment_radial) provides the radial force needed to lock the segment into the tip groove and the O-ring radial force component (Fdistal_ring_radial) provides the radial force needed to maintain the seal against the tip.

Furthermore, the O-ring axial force component (Fdistal_ring_axial) provides force to help remove the tip 220 during the ejection process.

Alignment/Misalignment

Analogous to coupler 100, the horizontal plane of the axial shoulder surface 1134 of coupler body member 1120 of the coupler 1100 and the horizontal plane of the axial shoulder seat 260 of tip 220 are maintained in a parallel adjacent relationship for correct tip alignment.

Dimensions and Relationships

Additionally, it is noted that for proper use and operation, dimensions between the coupler 1100 and tip 220 are related accordingly as described above for coupler 100.

Liquid Level Detection (LLD) Circuit Contacts

Referring to FIGS. 32 and 70, the pipette device assembly 10 further comprises a liquid level detection circuit assembly employed with pipette tip coupler 1100 in a manner analogous to coupler 100 described hereinabove for having an ability to detect a surface of a liquid being transferred or a surface onto or from which liquid is being transferred.

As illustrated in FIG. 70, the ring end 366 of the LLD circuit contact 364 is captured and sandwiched between the squeeze sleeve 46 and the squeeze ring 1200 for making electrical contact between the processing circuitry 362 of the LLD circuit board 360 (FIG. 32) and the squeeze ring 1200 that is made from an electrically conductive material and that makes electrical contact with the plurality of radially outwardly projecting segments 1162 that are also made using an electrically conductive nonpliable material. Accordingly, with the tip attached and the plurality of radially outwardly projecting segments 1162 squeezed or pushed and locked into the tip groove 246 (FIG. 71) of the tip 220, the plurality of radially outwardly projecting segments 1162 make electrical contact with the tip 220 that is also made from an electrically conductive material. As a result, and referring to FIG. 32, this completes the circuit between the processing circuitry 362 of the LLD circuit board 360 and the tip 220.

Additionally, the stop disk mounting post or distal mounting flange 36 is made from a non-conducting material. Therefore, the shank member 1102, body member 1120, and the plurality of radially outwardly projecting segments 1162 are insulated from the rest of the assembly.

Furthermore, the processing circuitry 362 of the LLD circuit board 360 detects a signal change when the tip 220 contacts liquid thereby having an ability to detect a surface of a liquid being transferred or a surface onto or from which liquid is being transferred. Again, actuation occurs when the coupler 1100 is attached to the tip 220 and the plurality of radially outwardly projecting segments 1162 are radially pushed circumferentially and locked into the tip groove of the tip 220.

Further Pipette Tip Embodiments

In a further embodiment, FIG. 76 illustrates a fragmentary, longitudinal sectional, side elevational view of the example embodiment of the disposable pipette tip 220 comprising an alternative sealing seat surface 2270 having an angle of substantially ninety degrees relative to the central longitudinal axis of the pipette tip 220.

Figure 77:
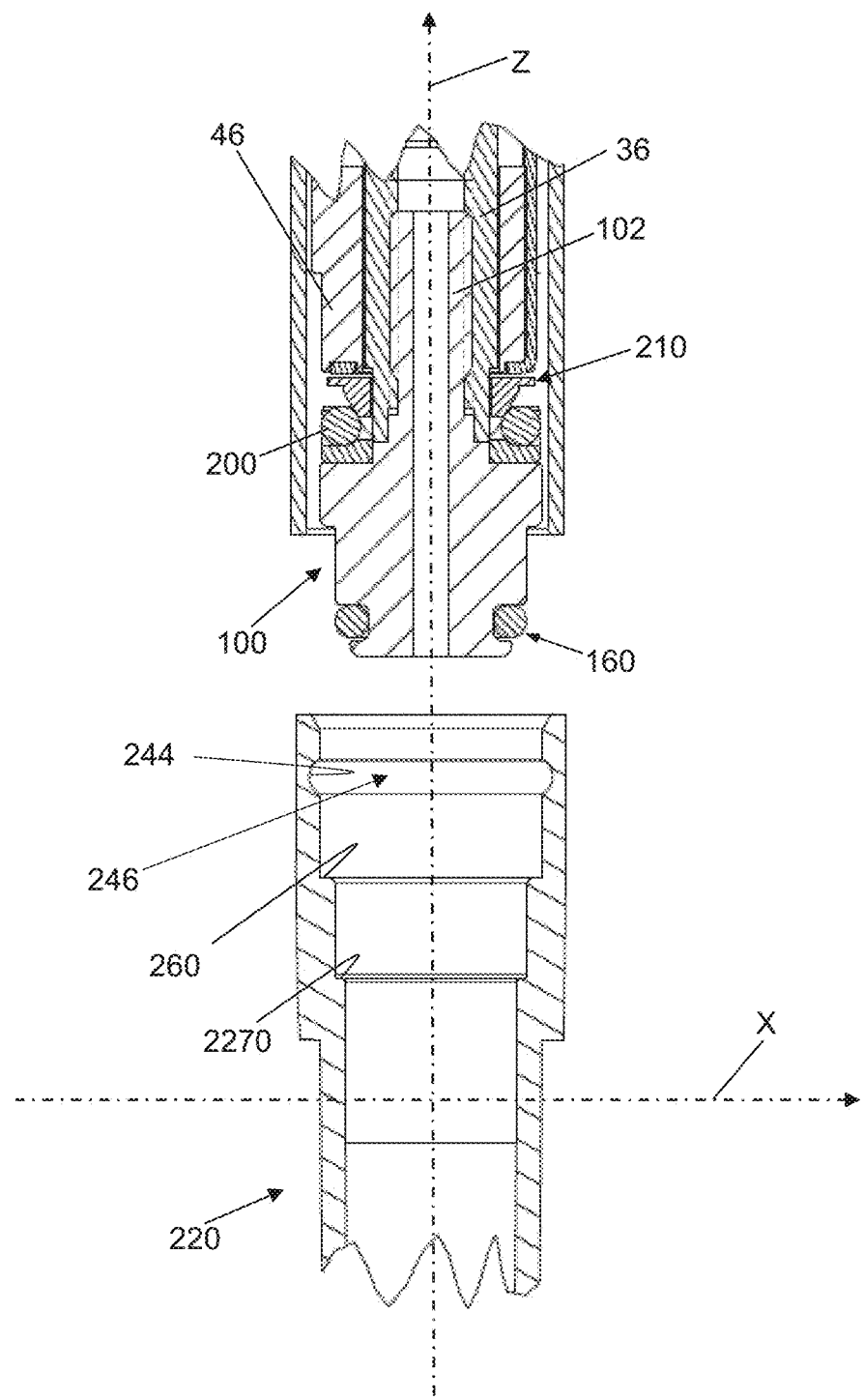
FIG. 77 is a fragmentary, longitudinal sectional, side elevational view of an example embodiment of the pipette tip coupler device positioned over an example embodiment of the disposable pipette tip comprising the alternative sealing seat surface angle of substantially ninety degrees.

FIG. 77 illustrates the example embodiment of the disposable pipette tip 220 comprising the alternative sealing seat surface 2270 being aligned for mating with, for example, the pipette tip coupler device 100.

Figures 78, 79:
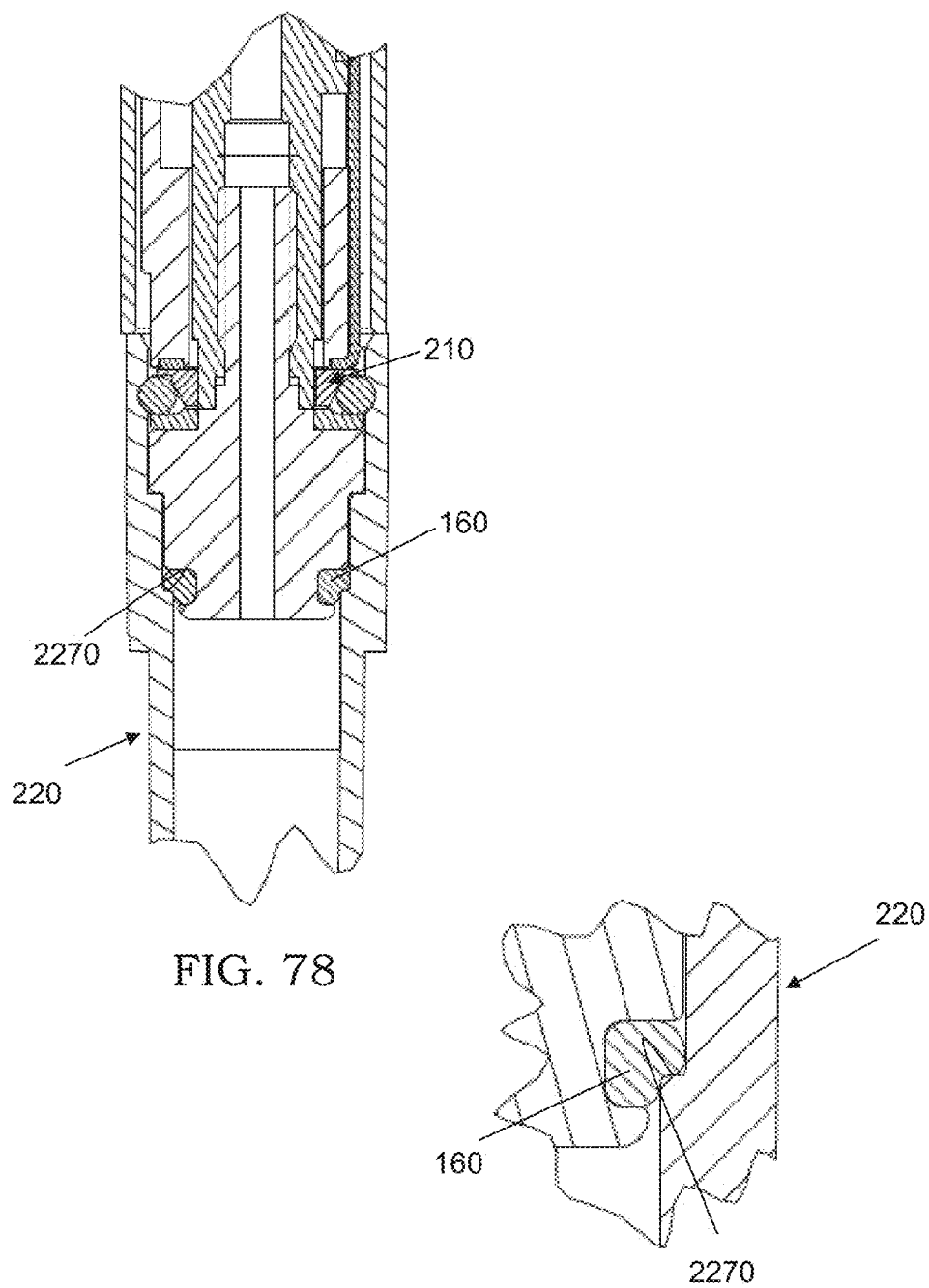
FIG. 78 is a fragmentary, longitudinal sectional, side elevational view of an example embodiment of the pipette tip coupler device positioned in the disposable pipette tip comprising the alternative sealing seat surface angle of substantially ninety degrees wherein the tip is lifted up to its final seated state and the annular wedge moved into its final position for defining a final coupling state with the distal elastomeric element in a final compressed and seated sealing state against the sealing seat surface having the alternative sealing seat surface angle of substantially ninety degrees.
FIG. 79 is a fragmentary, longitudinal sectional, side elevational detailed view of the distal elastomeric element in the final compressed state against the sealing seat surface having the alternative sealing seat surface angle of substantially ninety degrees as is illustrated in FIG. 78.

FIG. 78 illustrates the pipette tip coupler device 100 positioned in the disposable pipette tip 220 comprising the alternative sealing seat surface 2270 wherein the tip 220 with the alternative sealing seat surface 2270 is lifted up to its final seated state and the annular wedge 210 moved into its final position for defining a final coupling state with the distal elastomeric element 160 in a final compressed and seated sealing state against the alternative sealing seat surface 2270 having the alternative sealing seat surface angle of substantially ninety degrees.

FIG. 79 illustrates a detailed view of the distal elastomeric element 160 in the final compressed state against the alternative sealing seat surface 2270 having the alternative sealing seat surface angle of substantially ninety degrees.

Figures 80, 81:
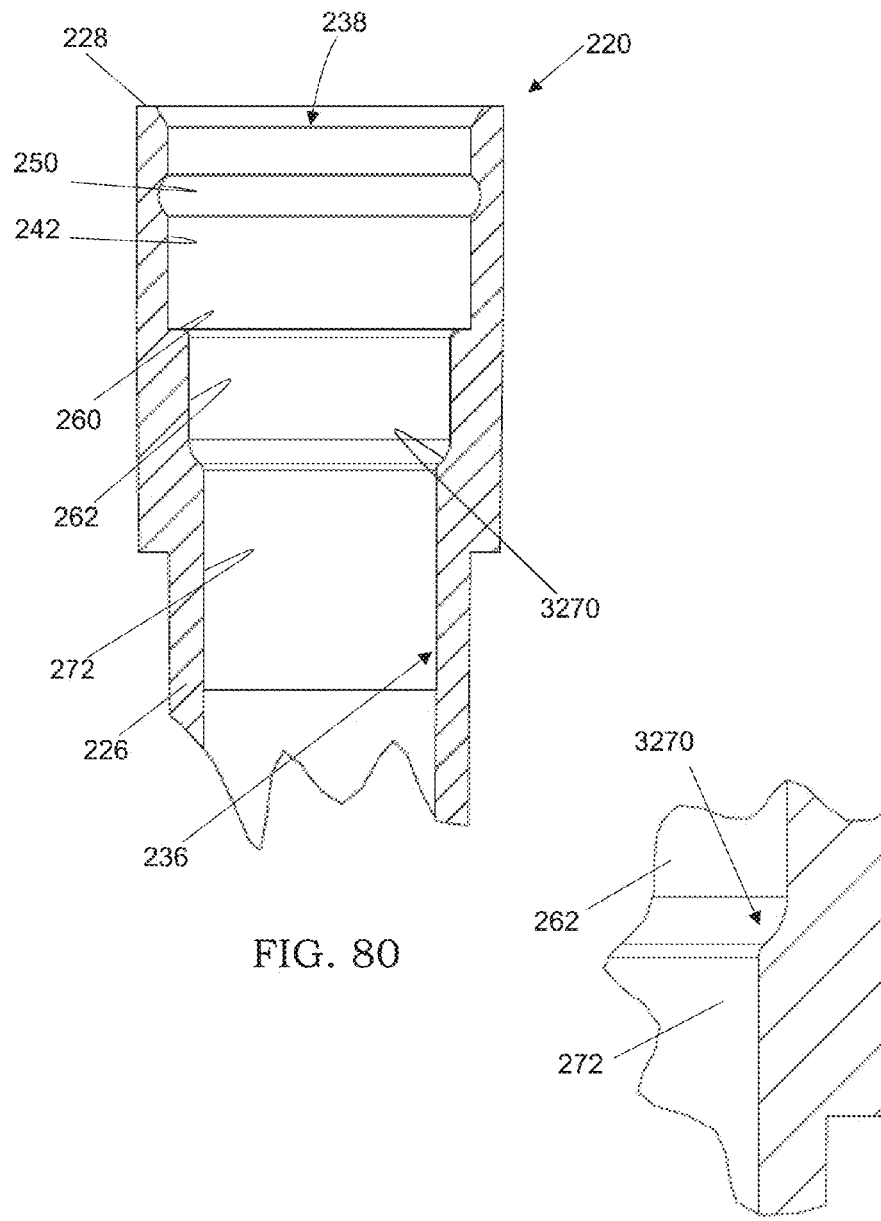
FIG. 80 is a fragmentary, longitudinal sectional, side elevational view of the upper interior of an example embodiment of the disposable pipette tip comprising another alternative sealing seat surface in the form of a circumferential radially concave sealing seat surface.
FIG. 81 is a fragmentary, longitudinal sectional, side elevational detailed view of an example embodiment of the disposable pipette tip illustrating detail of the circumferential radially concave sealing seat surface illustrated in FIG. 80.

In a further embodiment, FIG. 80 illustrates a fragmentary, longitudinal sectional, side elevational view of the upper interior of the example embodiment of the disposable pipette tip comprising another alternative sealing seat surface in the form of a circumferential radially concave sealing seat surface 3270 that is further illustrated in detail in FIG. 81.

Figure 82:
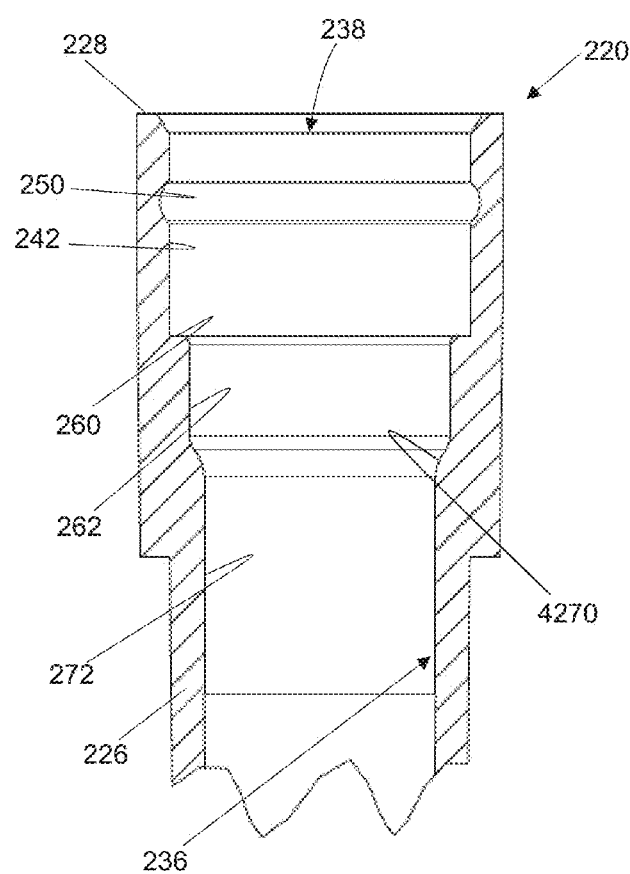
FIG. 82 is a fragmentary, longitudinal sectional, side elevational view of an example embodiment of the disposable pipette tip illustrating detail of a further alternative sealing seat surface in the form of a circumferential radially convex sealing seat surface.
Figure 83:
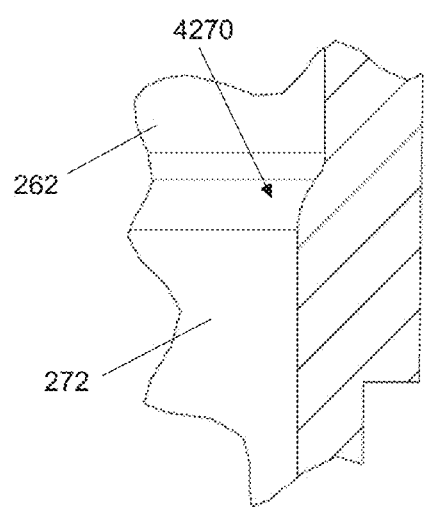
FIG. 83 is a fragmentary, longitudinal sectional, side elevational detailed view of an example embodiment of the disposable pipette tip illustrating detail of the circumferential radially convex sealing seat surface illustrated in FIG. 82.

In a further embodiment, FIG. 82 illustrates a fragmentary, longitudinal sectional, side elevational view of the example embodiment of the disposable pipette tip illustrating detail of a further alternative sealing seat surface in the form of a circumferential radially convex sealing seat surface 4270 that is further illustrated in detail in FIG. 83.

Figure 84:
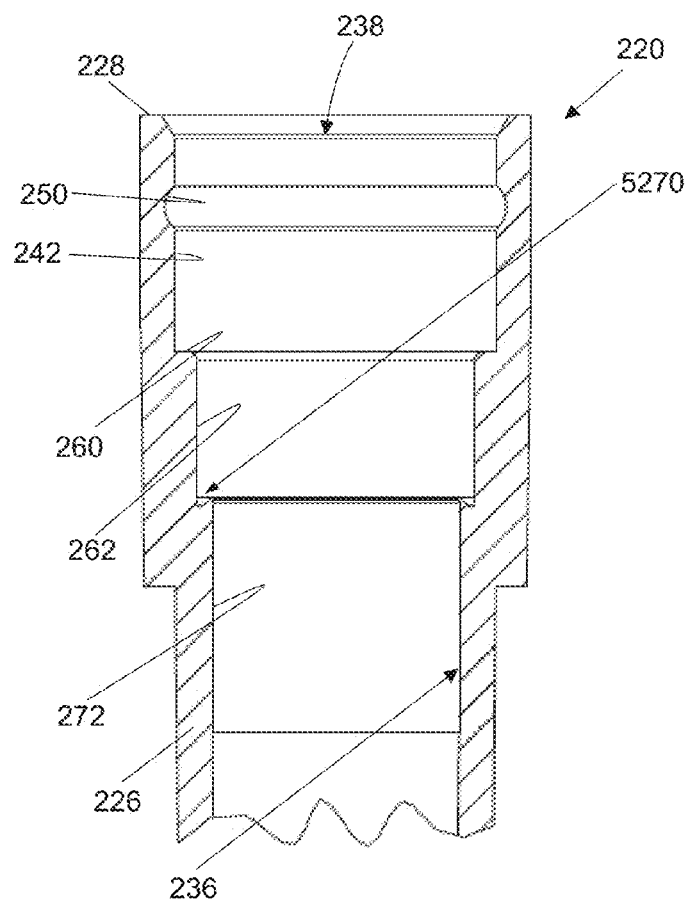
FIG. 84 is a fragmentary, longitudinal sectional, side elevational view of an example embodiment of the disposable pipette tip illustrating a yet further alternative sealing seat surface in the form of a circumferential upward facing tooth edge sealing seat surface.
Figure 85:
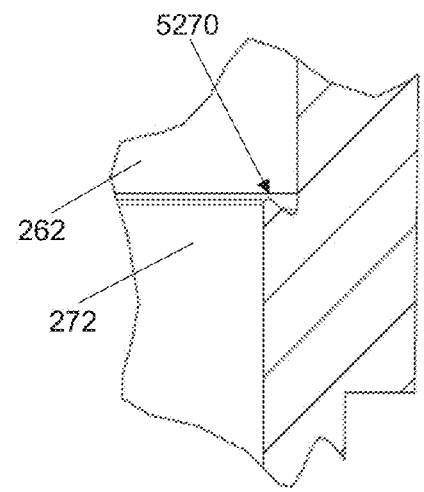
FIG. 85 is a fragmentary, longitudinal sectional, side elevational detailed view of an example embodiment of the disposable pipette tip illustrating detail of the circumferential upward facing tooth edge sealing seat surface illustrated in FIG. 84.

In a further embodiment, FIG. 84 illustrates a fragmentary, longitudinal sectional, side elevational view of the example embodiment of the disposable pipette tip illustrating a yet further alternative sealing seat surface in the form of a circumferential upward facing tooth edge sealing seat surface 5270 that is further illustrated in detail in FIG. 85.

Figure 86:
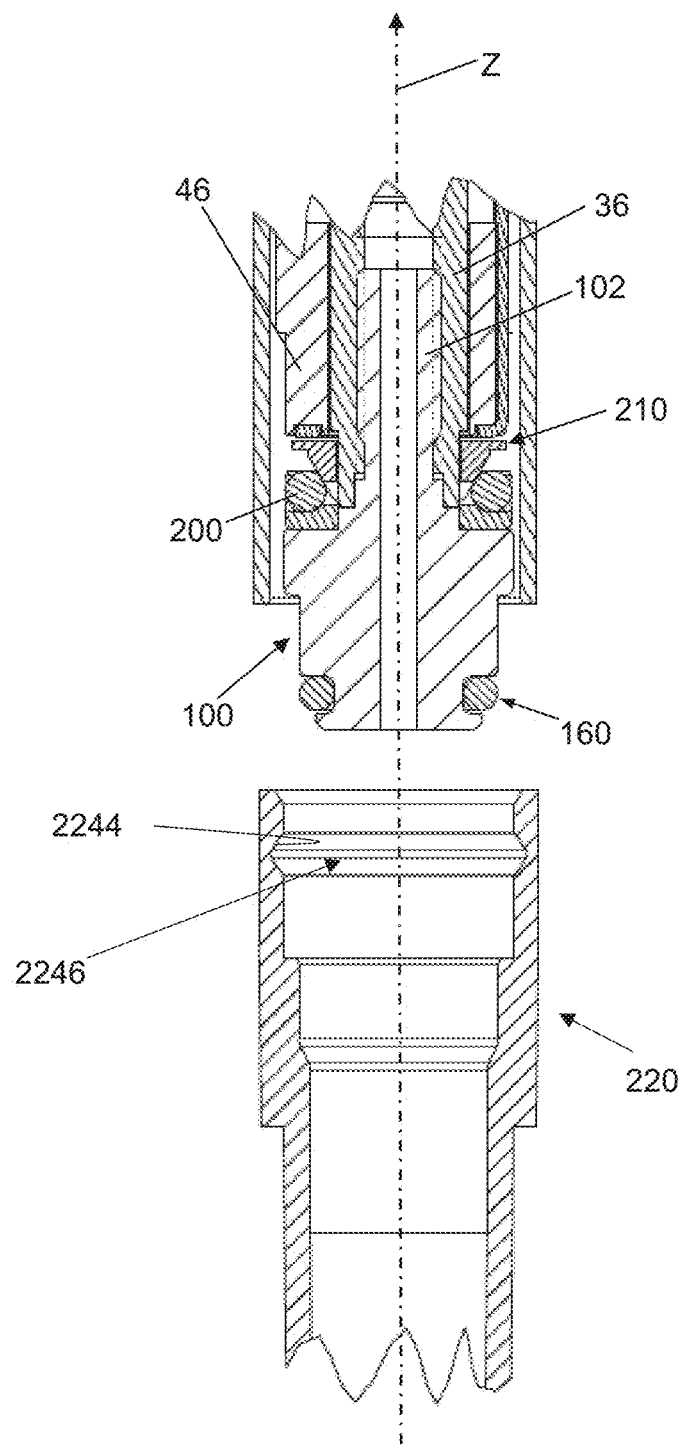
FIG. 86 is a fragmentary, longitudinal sectional, side elevational view of an example embodiment of the pipette tip coupler device positioned over the example embodiment of the disposable pipette tip comprising an alternative circumferential annular tip groove in the form of a V-shaped groove defined by an V-shaped circumferential interior surface of the disposable pipette tip opening toward the longitudinal axis and having a V-shaped cross section as illustrated.

FIG. 86 illustrates pipette tip coupler device 100 positioned over the example embodiment of the disposable pipette tip 220 comprising an alternative V-shaped groove 2246 defined by a V-shaped circumferential interior surface 2244 of the disposable pipette tip 220 opening toward the longitudinal Z axis and having a V-shaped cross section as illustrated.

Figure 87:
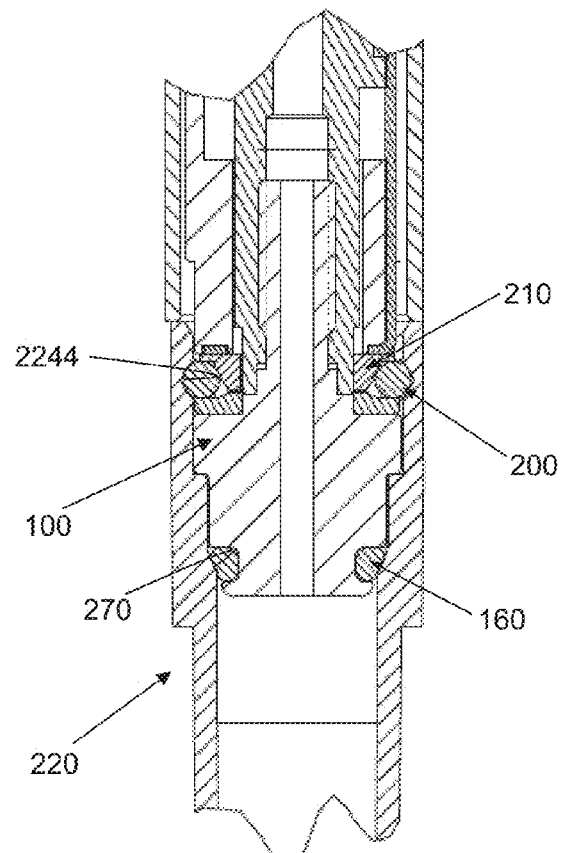
FIG. 87 is a fragmentary, longitudinal sectional, side elevational view of an example embodiment of the pipette tip coupler device positioned in the disposable pipette tip comprising the alternative V-shaped groove wherein the tip is lifted up to its final state with the rounded surfaces of the plurality of segments or balls being extended into the V-shaped groove and into abutment against the V-shaped circumferential interior surface with the distal elastomeric element in a final compressed and seated sealing state against the sealing seat surface of the tip.

FIG. 87 illustrates the pipette tip coupler device 100 being positioned in the disposable pipette tip 220 comprising the alternative V-shaped groove 2246 (FIG. 86) wherein the tip 220 with the alternative V-shaped groove 2246 is lifted up to its final state with the rounded surfaces of the plurality of spherical balls 200 being extended into the V-shaped groove 2246 and into abutment against the V-shaped circumferential interior surface 2244 with the distal elastomeric element 160 in the final compressed and seated sealing state against the sealing seat surface 270 of the tip.

Figure 88:
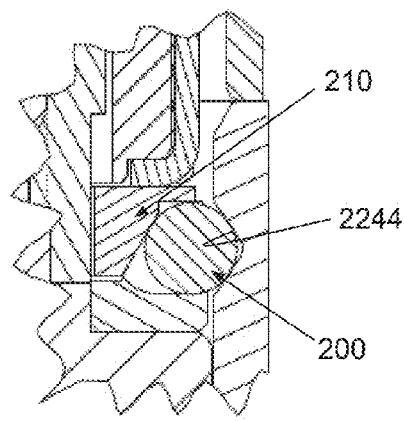
FIG. 88 is a fragmentary, longitudinal sectional, side elevational detailed view of the rounded surface of one of the plurality of segments or balls being extended into the V-shaped groove and abutting against the V-shaped circumferential interior surface defining the V-shaped groove as is illustrated in FIG. 87.
Figure 89:
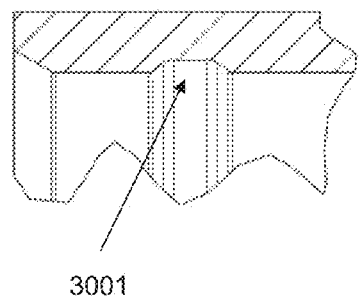
FIGS. 89 through 99 are fragmentary, longitudinal sectional, side elevational views detailing different further example embodiments of circumferential annular tip grooves.
Figure 90:
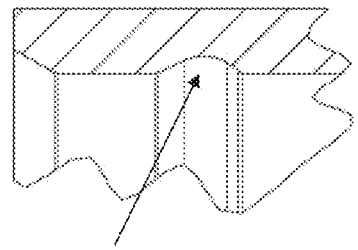
Figure 91:
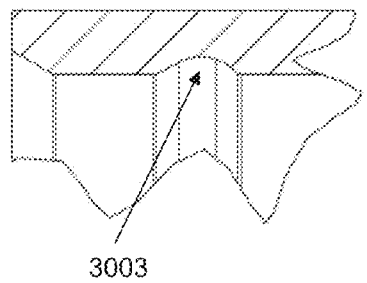
Figure 92:
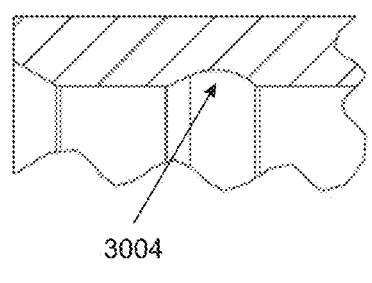
Figure 93:
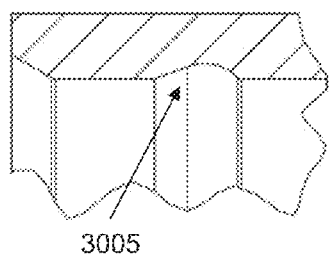
Figure 94:
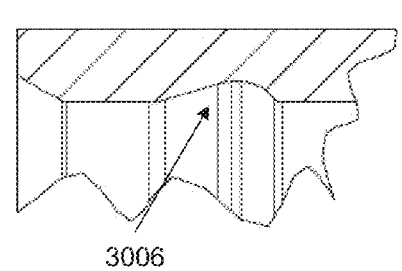
Figure 95:
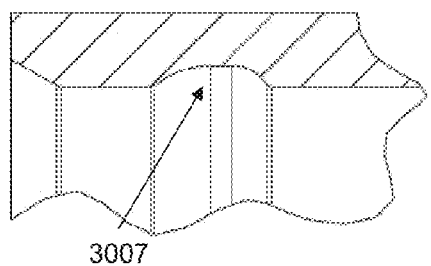
Figure 96:
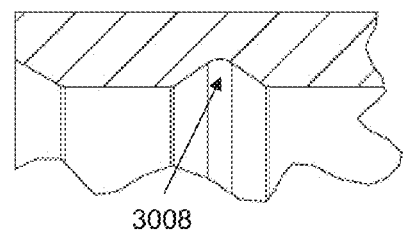
Figure 97:
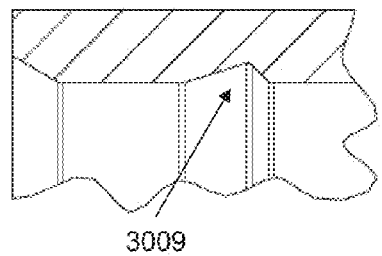
Figure 98:
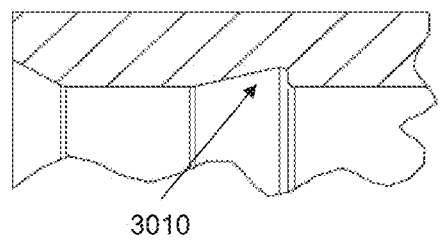
Figure 99:
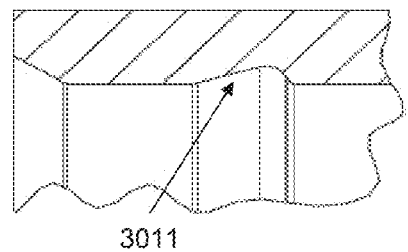

FIG. 88 illustrates the detail of the rounded surface of one of the plurality of segments or balls 200 being extended into the V-shaped groove 2246 (FIG. 86) and abutting against the V-shaped circumferential interior surface 2244.

Furthermore, FIGS. 89 through 99 illustrate fragmentary, longitudinal sectional, side elevational views detailing further different alternative example embodiments of the circumferential annular tip groove 246 illustrated in FIG. 16.

In particular, FIGS. 89 through 99 illustrate respective groove configurations 3001, 3002, 3003, 3004, 3005, 3006, 3007, 3008, 3009, 3010, and 3011. Additionally, the segments of the couplers may comprise radially outwardly extending faces complementary to the respective different alternative example embodiments of the respective groove configurations 3001 through 3011.

Moreover, the alternative sealing seat geometries 270 (FIG. 16), 2270 (FIG. 76), 3270 (FIG. 80), 4270 (FIG. 82), and 5270 (FIG. 84) may be employed with any one of the circumferential annular tip groove geometries 2246 3001, 3002, 3003, 3004, 3005, 3006, 3007, 3008, 3009, 3010, or 3011 respectively illustrated in FIGS. 89 through 99 and annular tip groove geometry 2246 illustrated in FIG. 860. Moreover, the elastomeric element may also have alternate shapes than an O-ring shape and may be in the form of, but not limited to, configurations complementary to the tip sealing seat.

Figure 100:
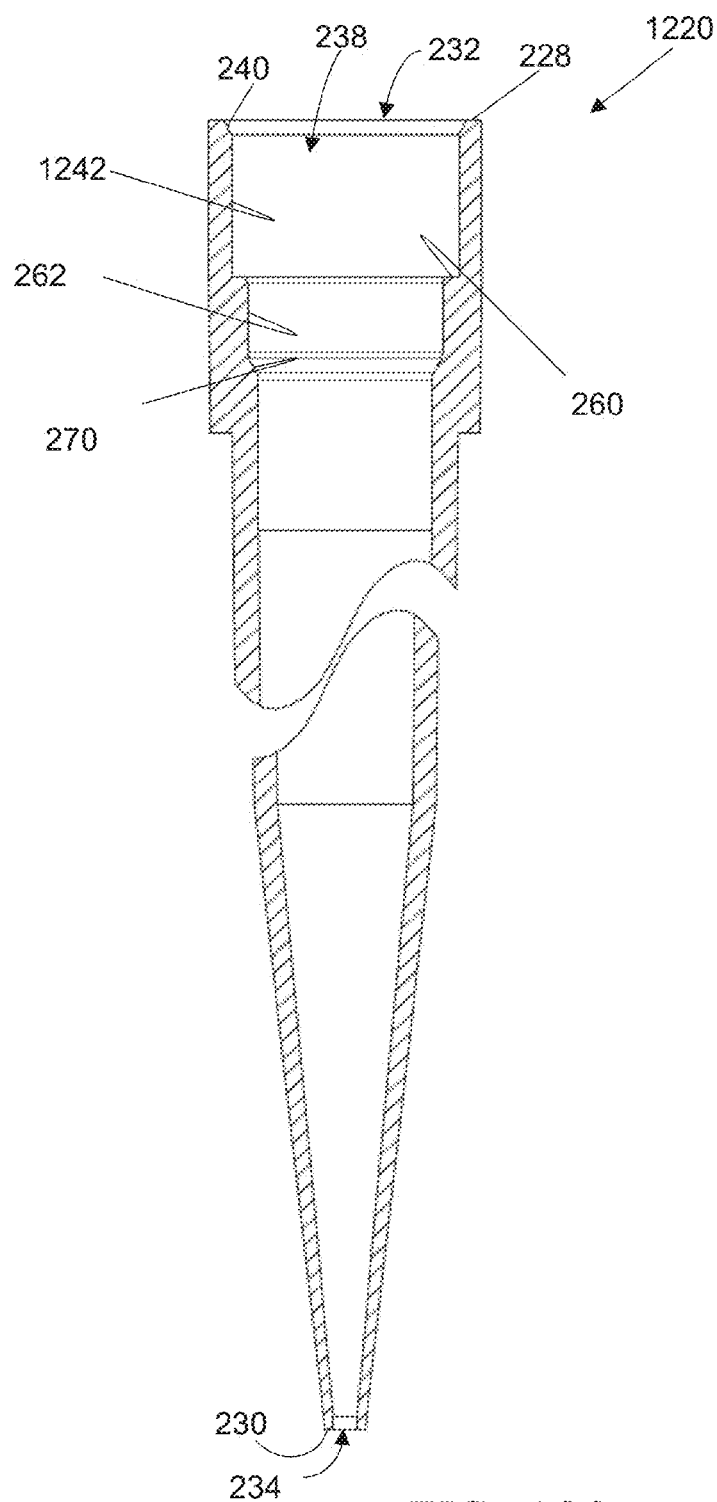
FIG. 100 is a fragmentary, longitudinal sectional, side elevational detailed view detailing the interior of a second example embodiment of a disposable pipette tip.

In another example embodiment, FIG. 100 details an interior of a disposable pipette tip 1220 that is analogous in all portions to disposable pipette tip 220 with the exception that interrupted interior surface section 242 is devoid of interruption thereby defining uninterrupted interior surface section 1242 of the disposable pipette tip 1220.

In alternative embodiments, the disposable pipette tip 1220 can also employ one of the alternative sealing alternative sealing seat geometries 270 (FIG. 16), 2270 (FIG. 76), 3270 (FIG. 80), 4270 (FIG. 82), and 5270 (FIG. 84) detailed above.

Figure 101:
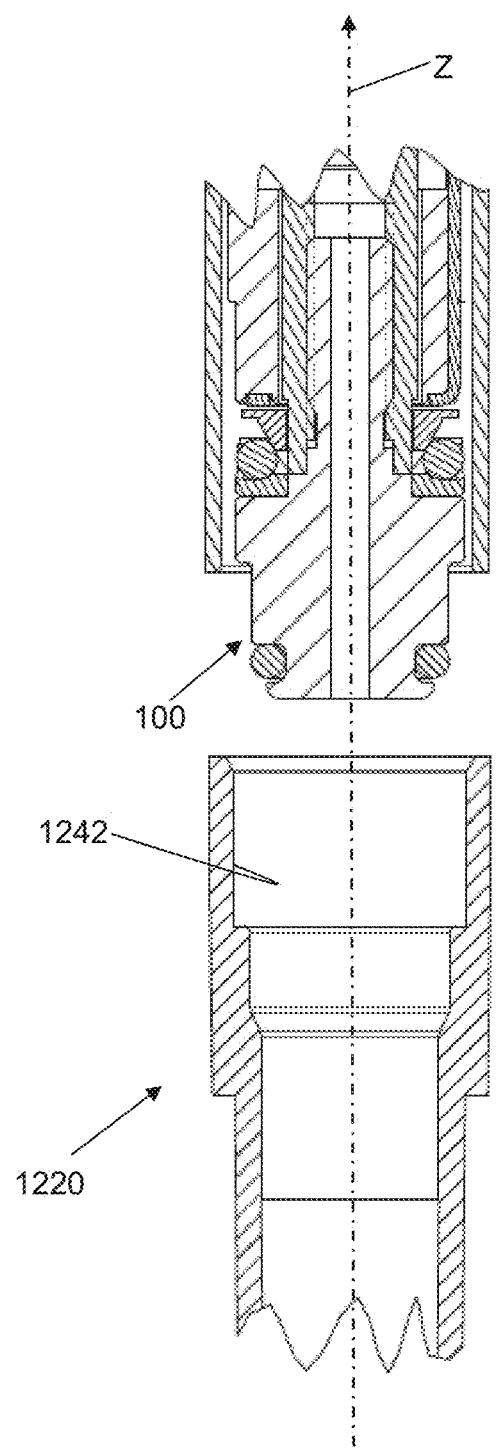
FIG. 101 is a fragmentary, longitudinal sectional, side elevational view of an example embodiment of the pipette tip coupler device positioned over the second example embodiment of the disposable pipette tip.

FIG. 101 illustrates pipette tip coupler device 100 positioned over the example embodiment of the disposable pipette tip 1220 comprising uninterrupted interior surface section 1242.

Figure 102:
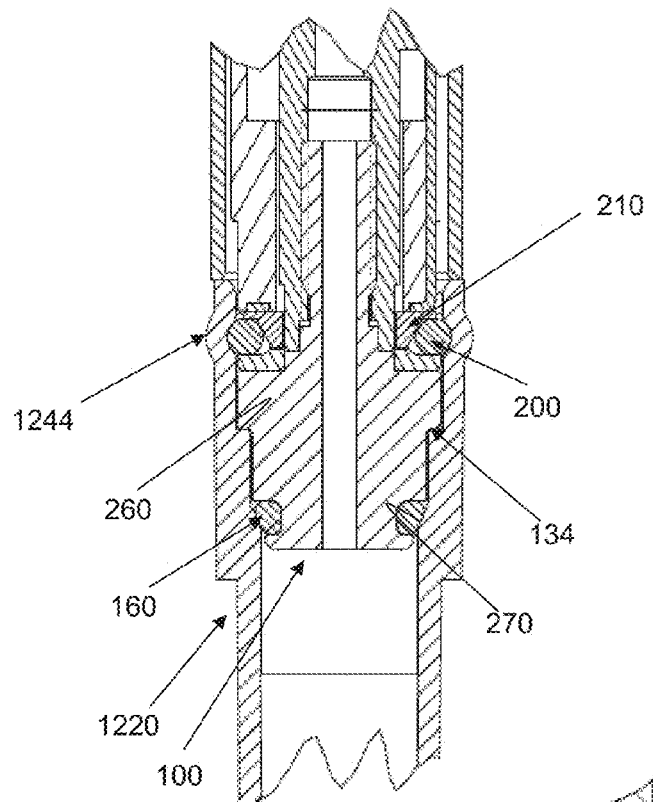
FIG. 102 is a fragmentary, longitudinal sectional, side elevational view of an example embodiment of the pipette tip coupler device positioned in the second example embodiment of the disposable pipette tip with the stop disk shoulder surface of the coupling device abutting against an axial stop surface of the second example embodiment of the disposable pipette tip and the rounded surfaces of the plurality of segments or balls being extended against an interior surface of a circumscribing sidewall of the second example embodiment of the disposable pipette tip resulting in a deformation of the interior surface and with the distal elastomeric element in a final compressed and seated sealing state against a sealing seat surface of the second example embodiment of the disposable pipette tip.
Figure 103:
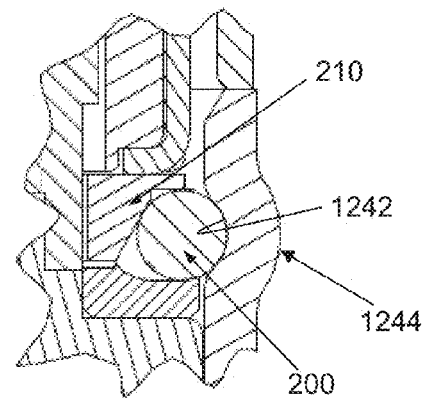
FIG. 103 is a fragmentary, longitudinal sectional, side elevational detailed view of the rounded surface of one of the plurality of spherical balls of the pipette tip coupler device being extended against and deforming the circumscribing sidewall of the second example embodiment of the disposable pipette tip.

FIG. 102 illustrates the pipette tip coupler device 100 positioned in the disposable pipette tip 1220 with the stop shoulder surface 134 of the coupler device 100 abutting against the axial stop surface 260 of disposable pipette tip 1220 with the rounded surfaces of the plurality of spherical balls 200 being extended against the interior surface 1242 (FIG. 103) of the circumscribing sidewall of the disposable pipette tip 1220 resulting in a deformation 1244 adjacent the interior surface 1242 (FIG. 103) of the disposable pipette tip 1220 and with the distal elastomeric element 160 in the final compressed and seated sealing state against the sealing seat surface 270 of the second example embodiment of the disposable pipette tip 1220.

Accordingly, the first working surface is in the form of, but not limited to, the respective groove configurations or the uninterrupted configuration illustrated in FIGS. 100-103 wherein the first substantially cylindrical interior surface section 242 is devoid of interruption thereby defining uninterrupted interior surface section 1242 of the disposable pipette tip 1220.

Shoulder Seat Surface Comprising Axially Upwardly Projecting Rib 5020

Figure 104:
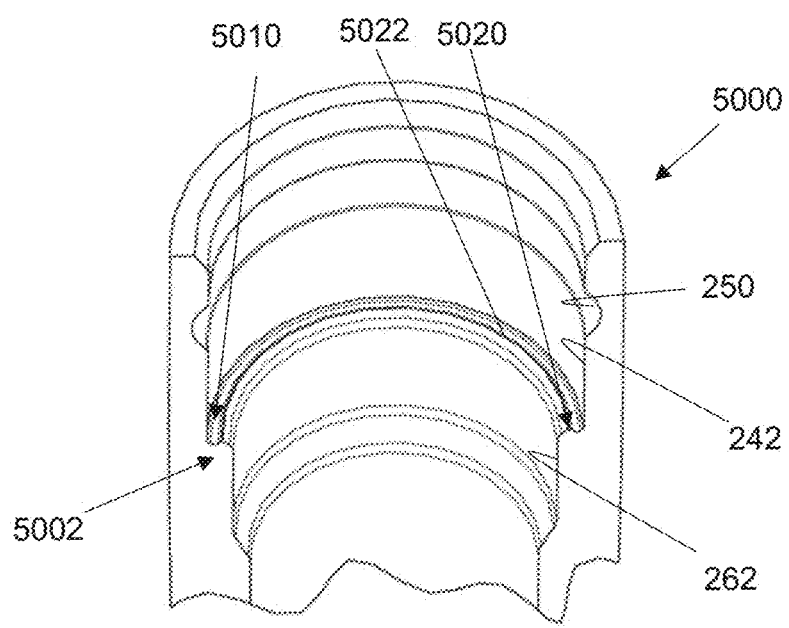
FIG. 104 is an upper fragmentary, longitudinal sectional, top and side perspective view detailing an upper interior of a further example embodiment of a disposable pipette tip comprising an interior axially upwardly facing shoulder seat surface having an axially upwardly facing annular groove coaxially disposed around an interior axially upwardly extending circumscribing rib.
Figure 105:
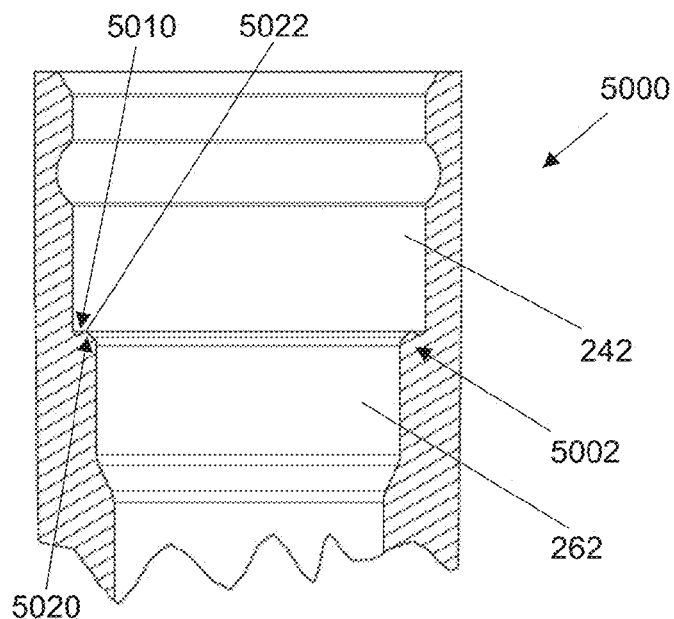
FIG. 105 is a fragmentary, longitudinal sectional, side elevational view of the further example embodiment of the disposable pipette tip comprising the interior axially upwardly facing shoulder seat surface having the axially upwardly facing annular groove coaxially disposed around the interior axially upwardly extending circumscribing rib having a continues solid circumscribing cross section.

In another example embodiment, FIGS. 104 and 105 detail an upper interior of a disposable pipette tip 5000 that is analogous in all portions to disposable pipette tip 220 (FIG. 16) with the exception of an alternative interior axially upwardly facing shoulder seat surface having an axially upwardly facing annular groove 5010 coaxially disposed around an axially upwardly extending circumscribing rib 5020 having a continues solid circumscribing cross section.

As illustrated in FIGS. 104 and 105, the first substantially cylindrical interior surface section 242 is axially distally proceeded by the second substantially cylindrical interior surface section 262 having a second diameter less than the first diameter of the first substantially cylindrical interior surface section 242 for forming the proximally facing, radially inwardly extending annular shoulder 5002 comprising the axially upwardly facing annular groove 5010 coaxially disposed around the axially upwardly extending circumscribing rib 5020.

Figure 106:
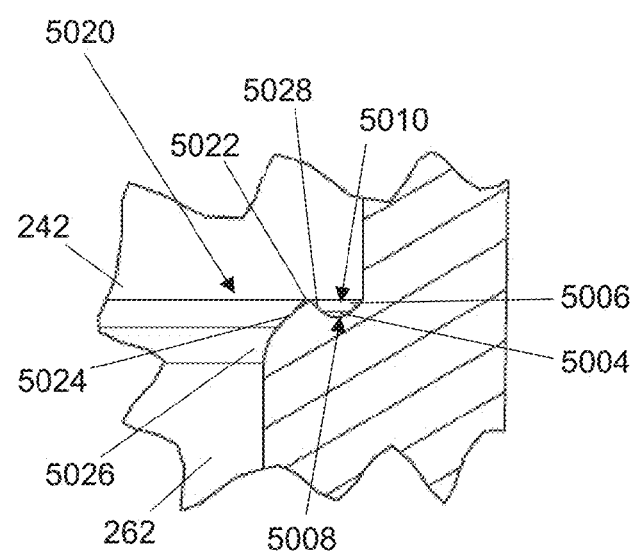
FIG. 106 is a fragmentary, longitudinal sectional, side elevational detailed view of the further example embodiment of the disposable pipette tip illustrating detail of the axially upwardly facing annular groove coaxially disposed around the interior axially upwardly extending circumscribing rib.

In one embodiment, and as illustrated in FIG. 106, the axially upwardly extending circumscribing rib 5020 comprises an uppermost rib seat surface or rib apex 5022 transitioning into sloping rib side surfaces 5024 and 5028. Sloping rib side surface 5024 transitions into an annular convex surface 5026 that terminates to the second substantially cylindrical interior surface section 262. On the outer radial side of the circumscribing rib 5020, sloping side surface 5028 forms a side wall surface of a groove surface 5008 defining the groove 5010. The groove surface 5008 further comprises a lower surface 5004 that transitions between the side surface 5028 and a sloping side surface 5006 that transitions into the first substantially cylindrical interior surface section 242.

In one embodiment, and referring to FIGS. 104 through 106, the axially upwardly extending circumscribing rib 5020 comprising the rib apex 5022 may be formed by, for example, the removal of material from the upper surface of the proximally facing, radially inwardly extending annular shoulder to form the groove 5010 or by the upper surface of the proximally facing, radially inwardly extending annular shoulder being molded to be devoid of material to form the groove 5010.

Figure 107:
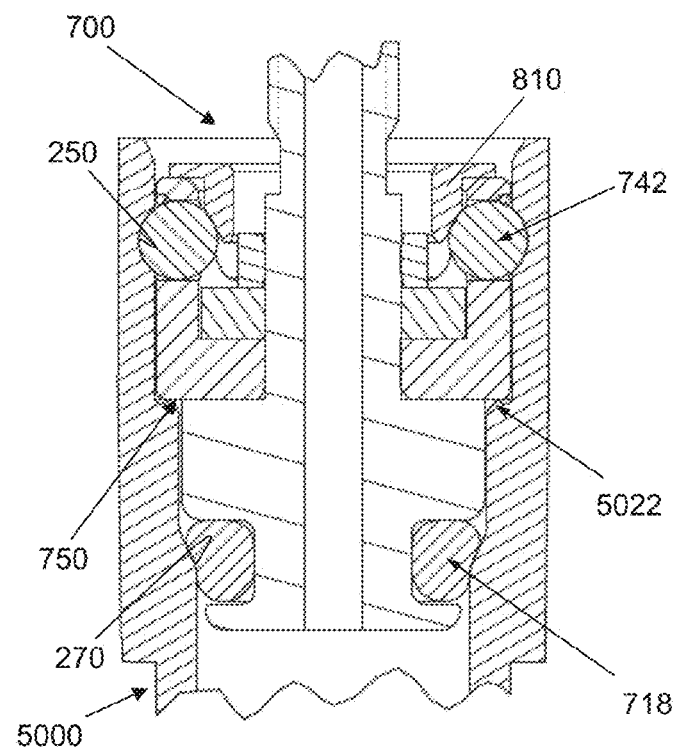
FIG. 107 is a fragmentary, longitudinal sectional, side elevational view of the third example embodiment of the pipette tip coupler device operatively positioned in the further example embodiment of the disposable pipette tip comprising the interior axially upwardly extending circumscribing rib.
Figure 108:
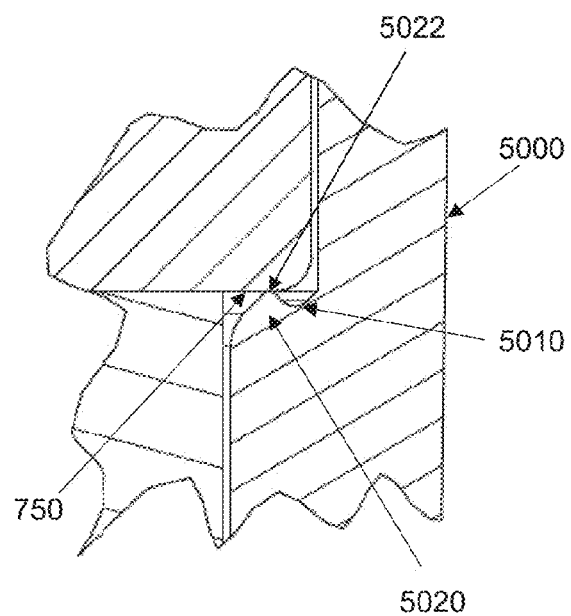
FIG. 108 is a fragmentary, longitudinal sectional, side elevational detailed view of a distally facing axial stop shoulder surface of the third example embodiment of the pipette tip coupler device abutting the interior axially upwardly extending circumscribing rib of the further example embodiment of the disposable pipette tip.

Referring to FIGS. 107 and 108, the disposable pipette tip 5000 can be used with one of the pipette tip coupler devices described above such as coupling device 700 wherein reducing the proximally facing surface area of the radially inwardly extending annular shoulder 5002 by forming rib apex 5022 provides an increase in the pressure between the tip 5000 and the stop shoulder surface 750 of the coupling device 700 on the rib apex 5022.

Referring to FIGS. 26, 107 and 108, the axial force (Fball_axial) produced by the ball 742 engaging the groove 250 will push against the rib apex 5022 thereby producing a seal between the tip 5000 and surface 750. Since pressure (P) is equal to force (F) divided by area (A), reducing the surface area of the tip seating shoulder by providing the rib apex 5022 results in increased pressure (P=F/A). This increased pressure between the tip 5000 and surface 750 provides a seal. Accordingly, the disposable pipette tip 5000 provides a new seal for every use. In alternative embodiments, circumscribing rib 5020 may also be provided by a sealant bead, an elastomeric washer, an O-ring, or other material to provide a configuration exemplified by rib 5020.

Internal Seal Pipette Tip Assembly 6010

Figure 109:
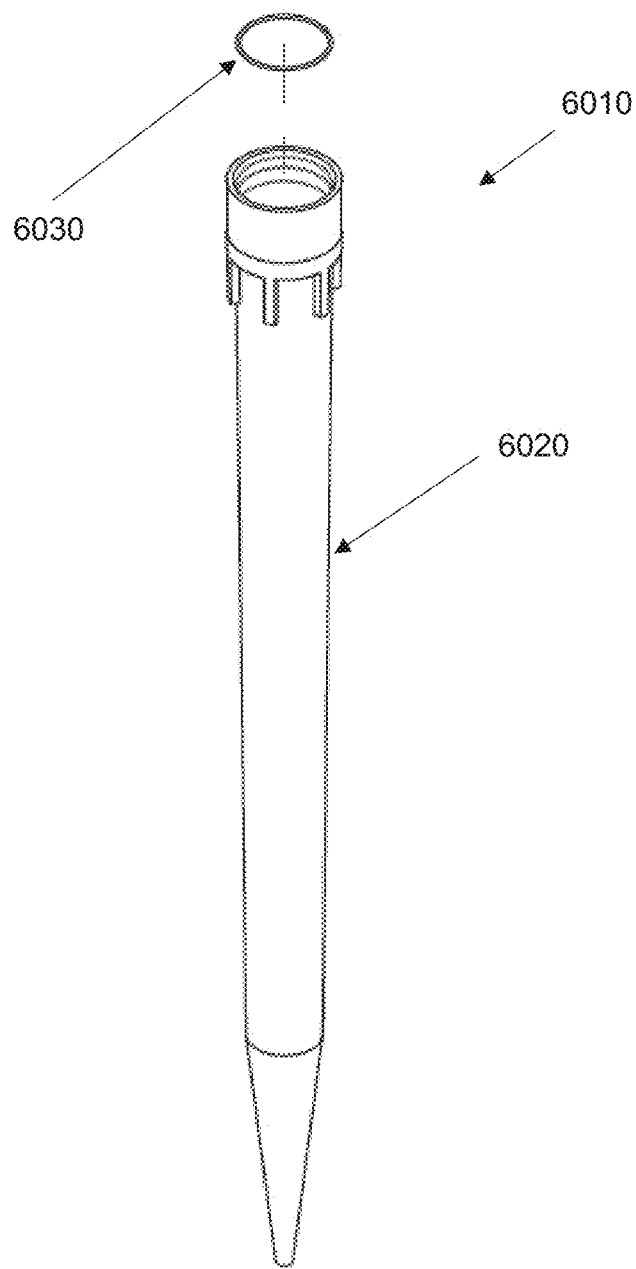
FIG. 109 is an exploded parts perspective view of an example embodiment of an internal seal pipette tip assembly comprising an internal seal pipette tip and an internal seal.

In another example embodiment, FIG. 109 illustrates an example embodiment of an internal seal pipette tip assembly 6010 comprising an internal seal pipette tip 6020 and an internal seal 6030.

Figure 110:
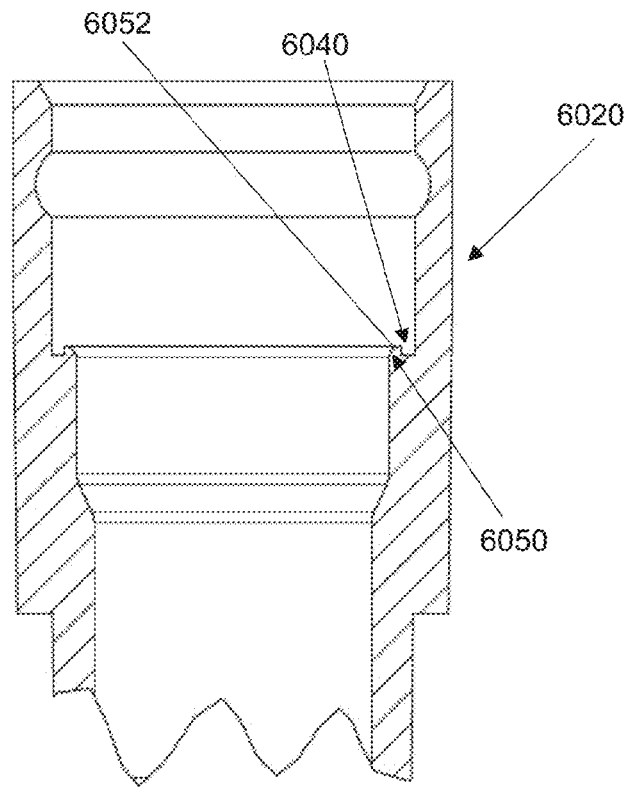
FIG. 110 is an upper fragmentary, longitudinal sectional, side elevational view detailing an upper interior of an example embodiment of the internal seal pipette tip comprising an interior axially upwardly facing shoulder seat surface having an axially upwardly facing annular groove coaxially disposed around an radially interior axially upwardly extending circumscribing rib having a continues solid circumscribing cross section.

Referring to FIGS. 109 and 110, the pipette tip 6020 is analogous in all portions to disposable pipette tip 220 (FIG. 16) with the exception of an alternative interior axially upwardly facing shoulder seat surface having an axially upwardly facing annular groove 6040 coaxially disposed around an axially upwardly extending circumscribing rib 6050 having an uppermost rib seat surface or rib apex 6052.

Figure 111:
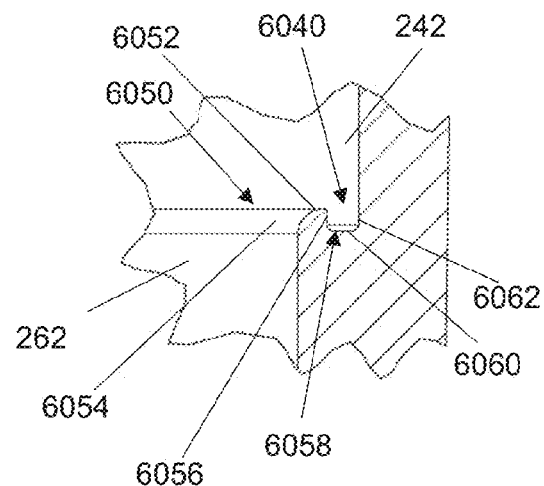
FIG. 111 is a fragmentary, longitudinal sectional, side elevational detailed view of an example embodiment of the internal seal pipette tip illustrating detail of the axially upwardly facing annular groove coaxially disposed around the radially interior axially upwardly extending circumscribing rib.

As illustrated in detail in FIG. 111, axially upwardly extending circumscribing rib 6050 comprises an uppermost rib seat surface or rib apex 6052 transitioning into an annular convex surface 6054 on the radially inner side of the rib apex 6052 and transitioning into a step side surface 6056 on the radially outer side of the rib apex 6052. Convex surface 6054 transitions into the second substantially cylindrical interior surface section 262 and step side surface 6056 forms a side wall surface of a groove surface 6058 defining the groove 6040. The groove surface 6058 further comprises a lower surface 6060 that transitions between the side surface 6056 and an axially upwardly extending side surface 6062 that transitions into the first substantially cylindrical interior surface section 242.

Figure 112:
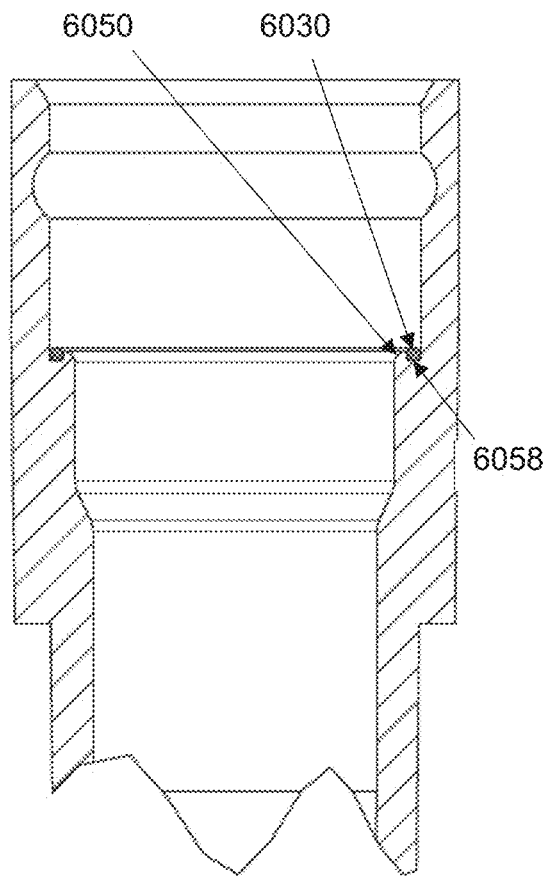
FIG. 112 is a fragmentary, longitudinal sectional, side elevational view of an example embodiment of the internal seal pipette tip assembly comprising the internal seal disposed in the axially upwardly facing annular groove.
Figure 113:
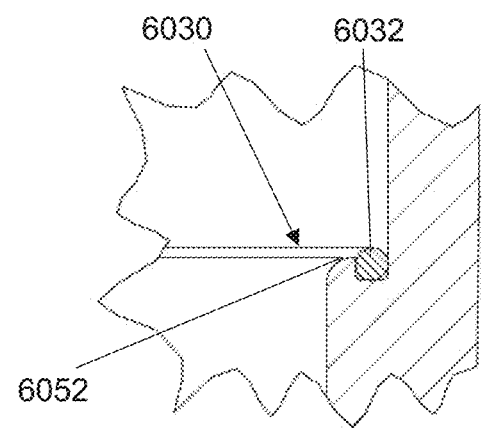
FIG. 113 is a fragmentary, longitudinal sectional, side elevational detailed view of the internal seal disposed in the axially upwardly facing annular groove.

As illustrated in FIG. 112, the internal seal 6030 is configured to be disposed for compression in the axially upwardly facing annular groove 6040 (FIG. 111) defined by groove surface 6058. Additionally, and as illustrated in FIG. 113, the internal seal 6030 is further configured to comprise in its uncompressed state an axially upwardly extending circumscribing sector portion 6032 having an axial elevation greater than the axial elevation of the circumscribing rib apex 6052 of the axially upwardly extending circumscribing rib 6050.

Figure 114:
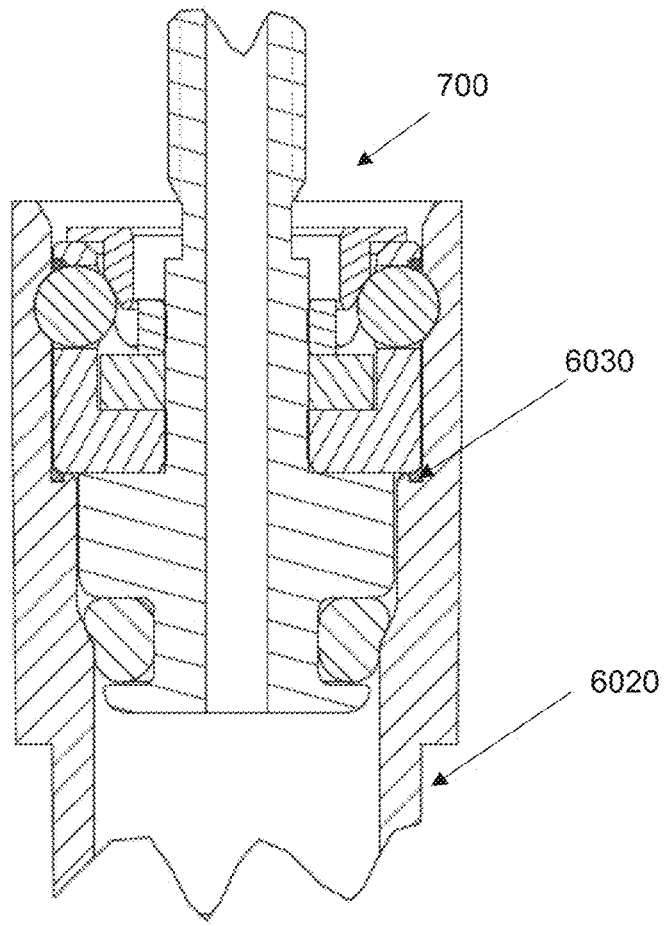
FIG. 114 is a fragmentary, longitudinal sectional, side elevational view of the third example embodiment of the pipette tip coupler device positioned in and operatively coupled to an example embodiment of the internal seal pipette tip assembly.
Figure 115:
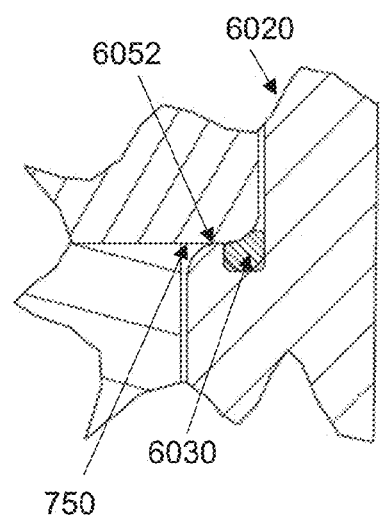
FIG. 115 is a fragmentary, longitudinal sectional, side elevational detailed view of a distally facing axial stop shoulder surface of the third example embodiment of the pipette tip compressing the internal seal disposed in the axially upwardly facing annular groove and contacting the radially interior axially upwardly extending circumscribing rib disposed coaxially within and radially adjacent to the axially upwardly facing annular groove.

The internal seal pipette tip assembly 6010 can be used with any of the pipette tip coupler devices described above such as coupling device 700 as is illustrated in FIGS. 114 and 115 wherein the pipette tip coupler device 700 is positioned in and operatively coupled to the internal seal pipette tip assembly 6010 (FIG. 109). With the pipette tip coupler device 700 operatively coupled to the internal seal pipette tip assembly 6010 as is illustrated in FIGS. 114 and 115, the distally facing axial stop shoulder surface 750 of the third example embodiment of the pipette tip coupler device 700 compresses the internal seal 6030 disposed in the axially upwardly facing annular groove 6040 to the extent of contact between the distally facing axial stop shoulder surface 750 and the rib apex 6052 of the axially upwardly extending circumscribing rib 6050 (FIG. 111). Once the tip assembly 6010 and the coupling device 700 are operatively coupled together, the internal seal 6030 provides a seal between the tip 6020 and the coupling device 700.

Accordingly, the internal seal pipette tip assembly 6010 provides a new internal seal 6030 for every use. Additionally, the internal seal 6030 provides a secondary sealing function and, in one embodiment, a replacement seal for distal seal 718. In one embodiment, the internal seal 6030 may be molded in place during the molding operation of the tip 6020. In other example embodiments, the internal seal 6030 may comprise another sealing mechanism, such as elastomeric element such as an O-ring, elastomeric washer, a thin layer of sealant, a sealant bead, an adhesive, or other sealant material or mechanism A Further Aspect In light of the above, and in a further aspect, an example embodiment of a method is provided for securing attachment of at least one pipette tip to at least one pipette tip coupler carried by a pipette device; the method comprising: (1) providing a pipette tip coupler comprising an upper body portion carrying a plurality of circumferentially disposed segments, a lower stem portion carrying an elastomeric sealing element, and a axially downwardly facing axial stop surface located axially between the plurality of circumferentially disposed segments and the elastomeric sealing element, the pipette tip coupler further comprising an interior circumscribing sidewall defining a central channel extending along a longitudinal central axis of the pipette tip coupler; (2) providing a pipette tip comprising a sidewall having an interior circumscribing surface defining a passage opening extending between an open distal end intended for immersion in a medium to be pipetted and an open proximal end opposite in an axial direction to the open distal end and the pipette tip comprising an upwardly facing axial stop surface formed by an axially stepped shoulder of the interior circumscribing surface of the sidewall of the pipette tip; (3) translating the pipette tip coupler through the open proximal end of the pipette tip leading with the lower stem portion; and (4) moving the plurality of circumferentially disposed segments between a radially retracted state and a radially translated state circumferentially for abutting an outer portion of the plurality of circumferentially disposed segments with a first interior working surface of the interior circumscribing surface of the sidewall of the pipette tip at a location axially above the upwardly facing axial stop of the pipette tip for lifting the pipette tip to abut the upwardly facing axial stop shoulder surface of the pipette tip with the distally facing axial stop shoulder surface of the upper body portion of the pipette tip coupler while concurrently compressing the elastomeric element against a second interior working surface of the interior circumscribing surface of the sidewall of the pipette tip at a location axially below the upwardly facing axial stop shoulder surface of the pipette tip.

INDUSTRIAL APPLICABILITY

The above delineation of the systems, assemblies, devices, and methods including uses and operations, demonstrate the industrial applicability of embodiment(s) of the present disclosure.

In light of the present disclosure as set forth above, it should be apparent that further numerous structural modifications and adaptations may be resorted to without departing from the scope and fair meaning of the embodiment(s) of the present disclosure as set forth hereinabove and as described hereinbelow by the claims. Hence, the spirit and scope of the appended claims should not be limited to the above delineated description of the embodiment(s) of the present disclosure. And, in the appended claims reference to an element in the singular is not intended to mean "one and only one" unless explicitly so stated, but rather "one or more." Moreover, it is not necessary for a device or method to address each and every problem sought to be solved by the present disclosure, for it to be encompassed by the present claims.

What is claimed is:

1. A pipette tip coupling device and pipette tip assembly comprising:

a pipette tip comprising a circumscribing sidewall with an open interior passage extending along a central longitudinal axis of the pipette tip between an open proximal end and an open distal end of the pipette tip;

a pipette tip coupling device comprising:

a shank having a proximal end face;

a coupler body distal to the shank, wherein a diameter of a widest portion of the coupler body is greater than a diameter of a widest portion of the shank;

a distal stem portion comprising:

a proximal neck; and a distal end plate;

an open-ended interior circumscribing surface forming an open passageway extending longitudinally from the proximal end face through the distal end plate;

a distal elastomeric element, the distal elastomeric element disposed around the proximal neck of the distal stem portion and adjacent to the distal end plate of the distal stem portion; and a pipette tip ball assembly circumscribing the shank comprising:

a plurality of spherical balls, wherein the spherical balls are circumferentially spaced apart; and a ring-shaped raceway body comprising a plurality of circumferentially spaced apart circular ball openings each capable of carrying one of the plurality of spherical balls;

wherein a portion of each of the plurality of spherical balls abuts against a first inner surface of the circumscribing sidewall of the pipette tip for securing the pipette tip to the pipette tip coupling device, and wherein the elastomeric element abuts against a second inner surface of the circumscribing sidewall of the pipette tip to form a seal between the pipette tip coupling device and the pipette tip.

2. The pipette tip coupling device and pipette tip assembly of claim 1 further comprising an annular wedge movably circumscribing the shank, the annular wedge comprising:

a proximal wedge surface;

a distal wedge surface, wherein a circumference of the proximal wedge surface is larger than a circumference of the distal wedge surface;

an exterior surface, wherein the exterior surface connects the proximal wedge surface with the distal wedge surface; and wherein the exterior surface of the annular wedge abuts against the plurality of spherical balls of the pipette tip ball assembly.

3. The pipette tip coupling device and pipette tip assembly of claim 2 wherein the proximal wedge surface of the annular wedge further comprises a radially extending annular lip.

4. The pipette tip coupling device and pipette tip assembly of claim 2 wherein the spherical balls, the annular wedge, and the pipette tip each further comprises an electrically conductive material.

5. The pipette tip coupling device and pipette tip assembly of claim 2 wherein the annular wedge further comprises a plurality of circumferentially spaced apart concave surfaces disposed in the exterior surface of the annular wedge.

6. The pipette tip coupling device and pipette tip assembly of claim 5 wherein each of the plurality of circumferentially spaced apart concave surfaces disposed in the exterior surface of the annular wedge is complemental in shape to each of the plurality of spherical balls.

7. The pipette tip coupling device and pipette tip assembly of claim 1 wherein the ring-shaped raceway body further comprises a plurality of retaining stakes for securing the plurality of spherical balls in the circular ball openings.

8. The pipette tip coupling device and pipette tip assembly of claim 1 wherein the pipette tip ball assembly is configured to allow the plurality of spherical balls to radially advance and radially retract relative to the circumferentially spaced apart circular ball openings.

9. The pipette tip coupling device and pipette tip assembly of claim 1 wherein the coupler body further comprises:
 a proximal cylindrical portion;
 a distal cylindrical portion; and
 wherein the proximal cylindrical portion has a diameter that is greater than a diameter of the distal cylindrical portion, forming a distally facing stop shoulder surface.

10. The pipette tip coupling device and pipette tip assembly of claim 9 wherein the diameter of the distal cylindrical portion of the coupler body is greater than a diameter of the distal end plate of the distal stem portion of the coupler body.

11. The pipette tip coupling device and pipette tip assembly of claim 1 wherein the pipette tip coupling device further comprises an annular spacer circumscribing the shank.

12. The pipette tip coupling device and pipette tip assembly of claim 1 wherein the pipette tip coupling device further comprises an annular magnet circumscribing the shank.

13. The pipette tip coupling device and pipette tip assembly of claim 1 wherein the pipette tip ball assembly further comprises a ball keeper retaining ring for securing the spherical balls in the circumferentially spaced apart circular ball openings.

14. The pipette tip coupling device and pipette tip assembly of claim 1 wherein the pipette tip ball assembly further comprises a snap ring received in a retaining groove circumscribing the ring-shaped raceway body for securing the plurality of spherical balls in the circumferentially spaced apart circular ball openings.

15. The pipette tip coupling device and pipette tip assembly of claim 1 wherein each of the plurality of circumferentially spaced apart circular ball openings in the ring-shaped raceway body further comprises an interior annular tapering surface for securing one of the plurality of spherical balls in the circular ball openings.

16. The pipette tip coupling device and pipette tip assembly of claim 1 wherein the ring-shaped raceway body has a diameter greater than the diameter of the widest portion of the coupler body, forming a distally facing stop shoulder surface.

17. A pipette tip coupling device and pipette tip assembly comprising:
 a pipette tip comprising:
  a circumscribing sidewall with an open interior passage extending along a central longitudinal axis of the pipette tip between an open proximal end and an open distal end of the pipette tip;
  a first section comprising a substantially cylindrical surface formed in the interior surface of the circumscribing sidewall distal to the open proximal end, the first section having a first diameter;
  a second section comprising a substantially cylindrical surface formed in the interior surface of the circumscribing sidewall distal to the first section, the second section having a second diameter smaller than the first diameter;
  a stop shoulder surface formed in the interior surface of the circumscribing sidewall at the interface of the first section and the second section;
  a third section comprising a substantially cylindrical surface formed in the interior surface of the circumscribing sidewall distal to the second section, the third section having a third diameter smaller than the second diameter;
  a sealing seat surface formed in the interior surface of the circumscribing sidewall at the interface of the second section and the third section; and
  at least one frustoconical section formed in the interior surface of the circumscribing sidewall between the third section and the distal open lower end;
 a pipette tip coupling device comprising:
  a shank having a proximal end face;
  a coupler body distal to the shank, wherein a diameter of a widest portion of the coupler body is greater than a diameter of a widest portion of the shank;
  a distal stem portion comprising:
   a proximal neck; and
   a distal end plate;
  an open-ended interior circumscribing surface forming an open passageway extending longitudinally from the proximal end face through the distal end plate;
  a distal elastomeric element, the distal elastomeric element disposed around the proximal neck of the distal stem portion and adjacent to the distal end plate of the distal stem portion; and
  a pipette tip ball assembly circumscribing the shank comprising:
   a plurality of spherical balls, wherein the spherical balls are circumferentially spaced apart; and
   a ring-shaped raceway body comprising a plurality of circumferentially spaced apart circular ball openings each capable of carrying one of the plurality of spherical balls;
 wherein a portion of each of the plurality of spherical balls abuts against the first section of the pipette tip for securing the pipette tip to the pipette tip coupling device, and wherein the elastomeric element abuts against the sealing seat surface of the pipette tip to form a seal between the pipette tip coupling device and the pipette tip.

18. The pipette tip coupling device and pipette tip assembly of claim 17 wherein the stop shoulder surface is an annular, substantially planar surface substantially perpendicular to the central longitudinal axis of the pipette tip.

19. The pipette tip coupling device and pipette tip assembly of claim 17 wherein the stop shoulder surface further comprises:
 an upwardly facing annular stop surface groove; and
 an upwardly extending circumscribing rib.

20. The pipette tip coupling device and pipette tip assembly of claim 19 wherein the stop shoulder surface further comprises an internal seal in the upwardly facing annular stop surface groove.

21. The pipette tip coupling device and pipette tip assembly of claim 17 wherein the sealing seat surface is an annular, substantially planar surface substantially perpendicular to the central longitudinal axis of the pipette tip.

22. The pipette tip coupling device and pipette tip assembly of claim 17 wherein the sealing seat surface is a frustoconical annular surface further comprising:
 an upper annular sealing seat surface edge at the intersection of the second section and the sealing seat surface; and
 a lower annular sealing seat surface edge at the interface of the sealing seat surface and the third section, wherein the upper annular sealing seat surface edge is greater in diameter than the lower annular sealing seat surface edge.

23. The pipette tip coupling device and pipette tip assembly of claim 17 further comprising an annular chamfered interior surface formed in the interior surface of the circumscribing sidewall of the pipette tip extending radially inward from the open proximal end and terminating at the proximal end of the first section.

24. The pipette tip coupling device and pipette tip assembly of claim 17 wherein the at least one frustoconical section further comprises:
   a fourth section formed in the interior surface of the circumscribing sidewall distal to the third section; and
   a fifth section formed in the interior surface of the circumscribing sidewall distal to the fourth section and proximal to the distal open end, wherein the fifth section has a greater taper than the fourth section.

25. The pipette tip coupling device and pipette tip assembly of claim 17 wherein the coupler body further comprises:
   a proximal cylindrical portion;
   a distal cylindrical portion; and
   wherein the proximal cylindrical portion has a diameter that is greater than a diameter of the distal cylindrical portion, forming a distally facing stop shoulder surface.

26. The pipette tip coupling device and pipette tip assembly of claim 25 wherein the distally facing stop shoulder surface is configured to seat against the stop shoulder surface of the pipette tip.

27. The pipette tip coupling device and pipette tip assembly of claim 17 wherein the ring-shaped raceway body has a diameter greater than the diameter of the widest portion of the coupler body, forming a distally facing stop shoulder surface.

28. The pipette tip coupling device and pipette tip assembly of claim 27 wherein the distally facing stop shoulder surface is configured to seat against the stop shoulder surface of the pipette tip.

29. A pipette tip coupling device and pipette tip assembly comprising:
   a pipette tip comprising:
      a circumscribing sidewall with an open interior passage extending along a central longitudinal axis of the pipette tip between an open proximal end and an open distal end of the pipette tip;
      a first section formed in the interior surface of the circumscribing sidewall distal to the open proximal end comprising:
         a substantially cylindrical upper first portion having a first diameter;
         a substantially cylindrical lower first portion having the first diameter; and
         an annular groove interposed between the substantially cylindrical upper first portion and the substantially cylindrical lower first portion;
      a second section comprising a substantially cylindrical surface formed in the interior surface of the circumscribing sidewall distal to the first section, the second section having a second diameter smaller than the first diameter;
      a stop shoulder surface formed in the interior surface of the circumscribing sidewall at the interface of the first section and the second section;
      a third section comprising a substantially cylindrical surface formed in the interior surface of the circumscribing sidewall distal to the second section, the third section having a third diameter smaller than the second diameter;
      a sealing seat surface formed in the interior surface of the circumscribing sidewall at the interface of the second section and the third section; and
      at least one frustoconical section formed in the interior surface of the circumscribing sidewall between the third section and the distal open lower end;
   a pipette tip coupling device comprising:
      a shank having a proximal end face;
      a coupler body distal to the shank, wherein a diameter of a widest portion of the coupler body is greater than a diameter of a widest portion of the shank;
      a distal stem portion comprising:
         a proximal neck; and
         a distal end plate;
      an open-ended interior circumscribing surface forming an open passageway extending longitudinally from the proximal end face through the distal end plate;
      a distal elastomeric element, the distal elastomeric element disposed around the proximal neck of the distal stem portion and adjacent to the distal end plate of the distal stem portion; and
      a pipette tip ball assembly circumscribing the shank comprising:
         a plurality of spherical balls, wherein the spherical balls are circumferentially spaced apart; and
         a ring-shaped raceway body comprising a plurality of circumferentially spaced apart circular ball openings each capable of carrying one of the plurality of spherical balls;
   wherein a portion of each of the plurality of spherical balls abuts against the annular groove in the first section, and wherein the elastomeric element abuts against the sealing seat surface of the pipette tip to form a seal between the pipette tip coupling device and the pipette tip.

30. The pipette tip coupling device and pipette tip assembly of claim 29 wherein the annular groove is concave.

* * * * *